US008618352B2

(12) United States Patent
Welsh et al.

(10) Patent No.: US 8,618,352 B2
(45) Date of Patent: Dec. 31, 2013

(54) TRANSGENIC PORCINE MODELS OF CYSTIC FIBROSIS

(75) Inventors: Michael J. Welsh, Riverside, IA (US); Christopher S. Rogers, North Liberty, IA (US); Randall Prather, Rocheport, MO (US); John Engelhardt, Iowa City, IA (US); Ziying Yan, Iowa City, IA (US)

(73) Assignees: University of Iowa Research Foundation, Iowa City, IA (US); The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 12/283,980

(22) Filed: Sep. 17, 2008

(65) Prior Publication Data

US 2009/0241203 A1 Sep. 24, 2009

Related U.S. Application Data

(63) Continuation-in-part of application No. 12/074,632, filed on Mar. 5, 2008, now Pat. No. 7,989,675.

(60) Provisional application No. 60/966,971, filed on Aug. 30, 2007, provisional application No. 60/908,637, filed on Mar. 28, 2007.

(51) Int. Cl.
*A01K 67/027* (2006.01)
*A01K 67/00* (2006.01)
*A01K 67/033* (2006.01)
*C12N 15/00* (2006.01)
*C12N 5/00* (2006.01)

(52) U.S. Cl.
USPC ............... 800/17; 800/9; 800/21; 435/325

(58) Field of Classification Search
USPC ................ 800/8, 9, 17, 21; 435/325
See application file for complete search history.

(56) References Cited

U.S. PATENT DOCUMENTS

| | | | |
|---|---|---|---|
| 6,215,041 | B1 | 4/2001 | Stice et al. |
| 6,271,436 | B1 | 8/2001 | Piedrahita et al. |
| 6,503,698 | B1 | 1/2003 | Dobrinsky et al. |
| 6,700,037 | B2 | 3/2004 | Damiani et al. |
| 7,291,461 | B2 | 11/2007 | Welch et al. |
| 2005/0120400 | A1 | 6/2005 | Day et al. |
| 2006/0041945 | A1 | 2/2006 | Robl et al. |
| 2009/0235368 | A1 | 9/2009 | Welsh et al. |

FOREIGN PATENT DOCUMENTS

| | | |
|---|---|---|
| WO | WO 96/07732 | 3/1996 |
| WO | WO 99/36510 | 7/1999 |
| WO | WO 01/03722 | 1/2001 |
| WO | WO 01/73107 A1 | 10/2001 |
| WO | WO 03/055302 A1 | 7/2003 |
| WO | WO 2005/0104835 | 11/2005 |
| WO | WO 2007/034649 A1 | 3/2007 |
| WO | WO 2007/053637 A2 | 5/2007 |
| WO | WO 2008/106981 A1 | 9/2008 |
| WO | WO 2008/106982 A2 | 9/2008 |
| WO | WO 2008/106984 A2 | 9/2008 |
| WO | WO 2008/0121199 | 10/2008 |

OTHER PUBLICATIONS

Colledge (Nature Genetics, Aug. 1995, vol. 10, p. 445-452).*
Thomas (Nature, 2003, vol. 424. No. 6950, p. 788-793).*
Dai (Nature Biotech., Mar. 2002, vol. 20, p. 251-255).*
O'Neal (Human Mol. Genetics, Oct. 1993, vol. 2, No. 10, p. 1561-569).*
Zeiher (J. Clin. Invest. 1995, vol. 96, No. 4, p. 2051-2065).*
Dorin (Nature, 1992, vol. 359, No. 6392, p. 211-215).*
Welsh (Transactions of the Am. Clin. and Climatological Assoc., 2009, vol. 120, p. 149-162).*
Davidson (Nature Genetics, Apr. 1995, vol. 9, p. 351-357).*
Hasty (Somat Cell Mol Genet May 1995, vol. 21, No. 3, p. 177-187).*
MGI website description of Cftrtm1Bay, 2012.*
MGI website description of Cftrtm1Kth, 2012.*
MGI website description of Cftrtm1Hgu, 2012.*
Lai (Science, 2002, vol. 295, No. 1089, p. 1089-1092).*
U.S. Appl. No. 60/908,637, filed Mar. 28, 2007, Welsh et al.
U.S. Appl. No. 60/966,971, filed Aug. 30, 2007, Welsh et al.
U.S. Appl. No. 12/074,632, filed Mar. 5, 2008, Welsh et al.
Grosse-Hovest et al., "Cloned Transgenic Farm Animals Produce a Bispecific Antibody for T Cell-Mediated Tumor Cell Killing," Proc. Natl. Acad. Sci. U.S.A. 101:6858-6863, 2004.
Harris, "Towards an Ovine Model of Cystic Fibrosis," Hum. Mol. Genet. 6:2191-2193, 1997.
Hirata et al., "Efficient PRNP Gene Targeting in Bovine Fibroblasts by Adeno-Associated Virus Vectors," Cloning Stem Cells 6:31-36, 2004.
Hao et al., "Production of Endothelial Nitric Oxide Synthase (eNOS) Over-Expressing Piglets," Transgenic Res. 15:739-750, 2006.
Inoue et al., "High-Fidelity Correction of Mutations at Multiple Chromosomal Positions by Adeno-Associated Virus Vectors," J. Virol. 73:7376-7380, 1999.
Kelley et al, "In Vivo Activation of the Cystic Fibrosis Transmembrane Conductance Regulator Mutant ΔF508 in Murine Nasal Epithelium," Proc. Natl. Acad. Sci. U.S.A. 94:2604-2608, 1997.
Lai et al., "Production of α-1,3-Galactosyltransferase Knockout Pigs by Nuclear Transfer Cloning," Science 295:1089-1092, 2002.
Lai et al., "Creating Genetically Modified Pigs by Using Nuclear Transfer," Reprod. Biol. Endocrinol. 1:1-6, 2003.

(Continued)

*Primary Examiner* — Michael C. Wilson
(74) *Attorney, Agent, or Firm* — Clark & Elbing LLP

(57) ABSTRACT

The present invention provides transgenic, large non-human animal models of diseases and conditions, as well as methods of making and using such animal models in the identification and characterization of therapies for the diseases and conditions.

11 Claims, 23 Drawing Sheets
(11 of 23 Drawing Sheet(s) Filed in Color)

(56) References Cited

OTHER PUBLICATIONS

Lai et al., "Production of Cloned Pigs by Using Somatic Cells as Donors," Cloning and Stem Cells 5:233-241, 2003.

Lai et al., "A Method for Producing Cloned Pigs by Using Somatic Cells as Donors," Methods Mol. Biol. 254:149-163, 2004.

Lai et al., "Generation of Cloned Transgenic Pigs Rich in Omega-3 Fatty Acids," Nat. Biotechnol. 24:435-436, 2006.

Li et al., "Progress Toward Generating a Ferret Model of Cystic Fibrosis by Somatic Cell Nuclear Transfer," Reprod. Biol. Endocrinol. 1:1-8, 2003.

Li et al., "Cloned Transgenic Swine Via In Vitro Production and Cryopreservation," Biol. Reprod. 75:226-230, 2006.

Liu et al., "Targeted Correction of Single-Base-Pair Mutations with Adeno-Associated Virus Vectors under Nonselective Conditions," J. Virol. 78:4165-4175, 2004.

Liu et al., "Mild Processing Defect of Porcine ΔF508-CFTR Suggests that ΔF508 Pigs May not Develop Cystic Fibrosis Disease," Biochem. Biophys. Res. Comm. 373:113-118, 2008.

Ostedgaard et al., "Processing and Function of CFTR-ΔF508 are Species-Dependent," Proc. Natl. Acad. Sci. U.S.A. 104:15370-15375, 2007.

Park et al., "Production of Nuclear Transfer-Derived Swine that Express the Enhanced Green Fluorescent Protein," Animal Biotechnol. 12:173-181, 2001.

Park et al., "Developmental Potential of Porcine Nuclear Transfer Embryos Derived from Transgenic Fetal Fibroblasts Infected with the Gene for the Green Fluorescent Protein: Comparison of Different Fusion/Activation Conditions," Biol. Reprod. 65:1681-1685, 2001.

Prather et al., "Nuclear Remodeling and Reprogramming in Transgenic Pig Production," Exp. Biol. Med. 229:1120-1126, 2004.

Reynaert et al., "Morphological Changes in the Vas Deferens and Expression of the Cystic Fibrosis Transmembrane Conductance Regulator (CFTR) in Control, ΔF508 and Knock-Out CFTR Mice During Postnatal Life," Mol. Reprod. Dev. 55:125-135, 2000.

Rogers et al., University of Iowa, College of Medicine Research Week poster, Mar. 29, 2006 (also presented in substantially similar form on Feb. 23, 2006 at University of Iowa, Department of Internal Medicine Research Day, Feb. 23, 2006, with the exception of Figure 7).

Rogers et al., University of Iowa, Gene Therapy Center Retreat presentation, Apr. 26, 2006.

Rogers et al., "Gene Targeting of Pig CFTR: Progress Toward a Large Animal Model of Cystic Fibrosis," North American Cystic Fibrosis Meeting, 2006, Ped. Pulm. 41 S29, abstract 231, 2006.

Rogers et al., "Production of CFTR-Null and CFTR-ΔF508 Heterozygous Pigs by Adeno-Associated Virus-Mediated Gene Targeting and Somatic Cell Nuclear Transfer," J. Clin. Invest. 118:1571-1577, 2008.

Rogers et al., "The Porcine Lung as a Potential Model for Cystic Fibrosis," Am. J. Physiol. Lung Cell Mol. Physiol. 295:L240-L263, 2008.

Verkman, "From the Farm to the Lab: the Pig as New Model of Cystic Fibrosis," Am. J. Physiol. Lung Cell Mol. Physiol. 295:L238-L239, 2008.

Yan et al., "Ubiquitination of Both Adeno-Associated Virus Type 2 and 5 Capsid Proteins Affects the Transduction Efficiency of Recombinant Vectors," J. Virol. 76:2043-2053, 2002.

International Search Report from International Application No. PCT/US2008/002886, dated Aug. 21, 2008 (date of completion of the search) and Sep. 15, 2008 (date of mailing of report).

Written Opinion from International Application No. PCT/US2008/002886, dated Aug. 25, 2008 (date of completion of opinion) and Sep. 15, 2009 (date of mailing of opinion).

International Preliminary Report on Patentability from International Application No. PCT/US2008/002886, dated Aug. 25, 2008 (date of completion of opinion) and Sep. 29, 2009 (date of issuance of report).

Restriction Requirement dated Dec. 1, 2009 from U.S. Appl. No. 12/074,632.

Reply to Restriction Requirement dated Dec. 1, 2009 from U.S. Appl. No. 12/074,632, filed Feb. 1, 2010.

Information Disclosure Statement and Form PTO 1449 from U.S. Appl. No. 12/074,632, filed Feb. 2, 2010.

Office Action dated Apr. 30, 2010 from U.S. Appl. No. 12/074,632.

Reply to Office Action dated Apr. 30, 2010 from U.S. Appl. No. 12/074,632, filed Aug. 23, 2010.

Meyerholz et al., "Pathology of Gastrointestinal Organs in a Porcine Model of Cystic Fibrosis," Am. J. Pathol. 176:1377-1389, 2010.

Richt et al., "Production of Cattle Lacking Prion Protein," Nat. Biotech. 25:132-139, 2007.

Sun et al., "Adeno-Associated Virus-Targeted Disruption of the CFTR Gene in Cloned Ferrets," J. Clin. Invest. 118:1578-1583, 2008.

Van Heeckeren et al., "Role of Cftr Genotype in the Response to Chronic Pseudomonas aeruginosa Lung Infection in Mice," Am. J. Physiol. Lung Cell Mol. Physiol. 287:944-952, 2004.

Welsh et al., "Development of a Porcine Model of Cystic Fibrosis," Transactions of the Am. Clin. Climatol. Assoc. 120:149-162, 2009.

Amos-Landgraf et al., "A Rat Knock Out Model of Human Familial Adenomatous Polyposis," Proc. Amer. Assoc. Cancer Res., vol. 47, No. 1137, Apr. 1, 2006. (Abstract #4844).

Amos-Landgraf et al., "The Pirc Rat, a Complementary Genetic Model for Human Colon Cancer," http://www.imgs.org/abstracts/2006abstracts/IMGC_2006_abstracts4b.pdf, retrieved Jan. 1, 2006.

Rogers et al., "Disruption of the CFTR Gene Produces a Model of Cystic Fibrosis in Newborn Pigs," Science 321:1837-1841, 2008.

Extended European Search Report from European Patent Application No. 08726424.8, Dec. 22, 2011.

Maurisse et al., "Modification of the Pig CFTR Gene Mediated by Small Fragment Homologous Replacement," Ann. N.Y. Acad. Sci. 1082:120-123, 2006.

* cited by examiner

Figure 14
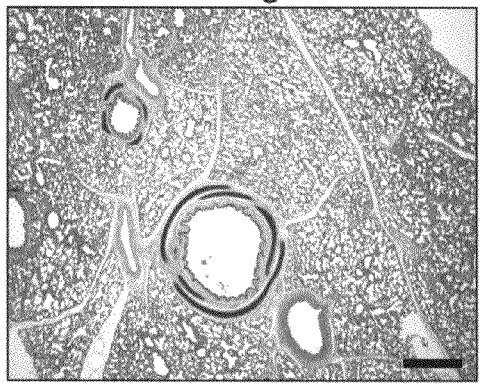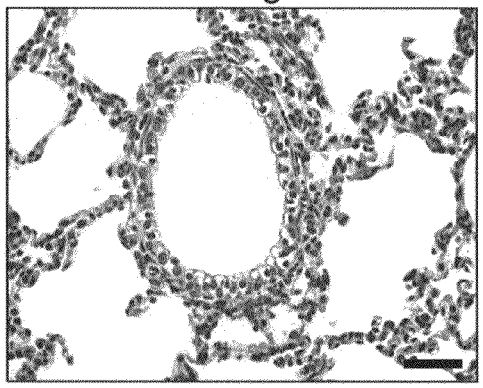
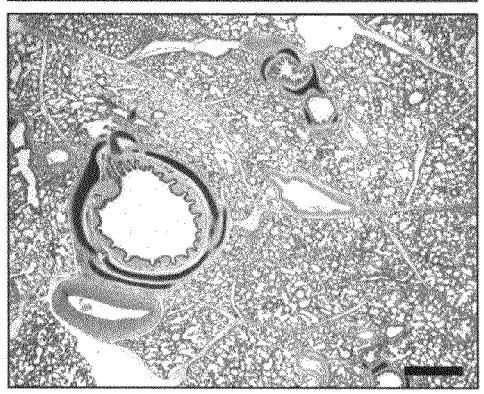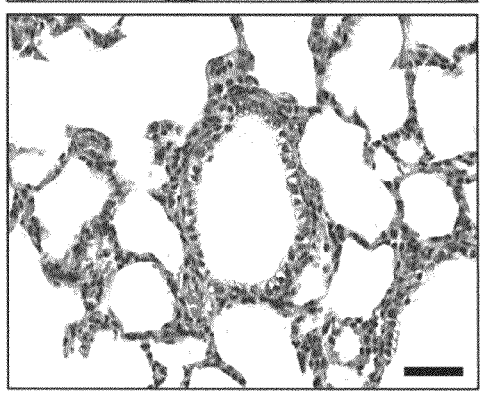
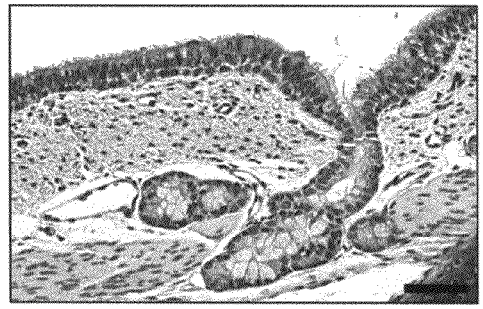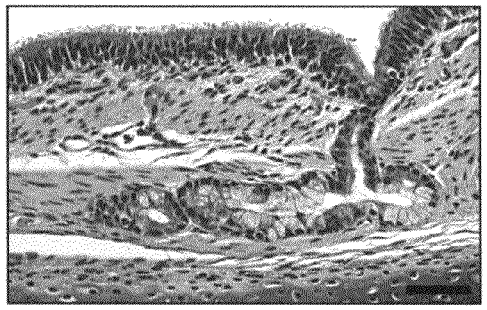

Figure 17

```
                                                                                          TM1
human     1 MQRSPLEKASVVSKLFFSWTRPILRKGYRQRLELSDIYQIPSVDSADNLSEKLEREWDRELASKKNPKLINALRRCFFWRFMFYGIFLYL
pig       1 MQRSPLEKASIFSKLFFSWTRPILRKGYRQRLELSDIYHISSSDSADNLSEKLEREWDRELASKKNPKLINALRRCFFWRFMFYGILLYI
mouse     1 MQKSPLEKASFISKLFFSWTTPILRKGYRHHLELSDIYQAPSADSADHLSEKLEREWDREQASKKNPQLIHALRRCFFWRFLFYGILLYI TM2
human    91 GEVTKAVQPLLLGRIIASYDPDNKEERSIAIYLGIGLCLLFIVRTLLIHPAIFGLHHIGMQMRIAMFSLIYKKTLKLSSRVLDKISIGQL
pig      91 GEVTKAVQPLLLGRIIASYDPDNKAERSIAIYLGVGLCLLFIVRTLLIHPAIFGLHHIGMQMRIAMFSLIYKKTLKLSSRVLDKISIGQL
mouse    91 GEVTKAVQPVLLGRIIASYDPENKVERSIAIYLGIGLCLLFIVRTLLIHPAIFGLHRIGMQMRTAMFSLIYKKTLKLSSRVLDKISIGQL TM3                       TM4
human   181 VSLLSNNLNKFDEGLALAHFVWIAPLQVALLMGLIWELLQASAFCGLGFLIVLALFQAGLGRMMMKYRDQRAGKISERLVITSEMIENIQ
pig     181 VSLLSNNLNKFDEGLALAHFVWIAPLQVTLIMGLIWELLQASAFCGLAFLVVLALFQAGLGKMMMKYRDQRAGKINERLVITSEMIENIQ
mouse   181 VSLLSNNLNKFDEGLALAHFIWIAPLQVTLIMGLIWDLLQFSAFCGLGLLIILVIFQAILGKMMVKYRDQRAAKINERLVITSEIIDNIY TM5                        TM6
human   271 SVKAYCWEEAMEKMIENLRQTELKLTRKAAYVRYFNSSAFFFSGFFVVFLSVLPYALIKGIILRKIFTTISFCIVLRMAVTRQFPWAVQT
pig     271 SVKAYCWEEAMEKMIENLRQTELKLTRKAAYVRYFNSSAFFFSGLFVVFLSVLPYALIKGIMLRKIFTTISFCIVLRMAVTRQFPWAVQT
mouse   271 SVKAYCWESAMEKMIENLREVELKMTRKAAYMRFFTSSAFFFSGFFVVFLSVLPYTVINGIVLRKIFTTISFCIVLRMSVTRQFPTAVQI NBD1
human   361 WYDSLGAINKIQDFLQKQEYKTLEYNLTTTEVVMENVTAFWEEGFGELFEKAKQNNNNRKTSNGDDSLFFSNFSLLGTPVLKDINFKIER
pig     361 WYDSLGAINKIQDFLQKQEYKTLEYNLTTTEVVMENVTAFWEEGFGKLFEKAKQNNNSRKISNGDNSLFFSNFSLLGTPVLKDISFKIER
mouse   361 WYDSFGMIRKIQDFLQKQEYKVLEYNLMTTGIIMENVTAFWEEGFGELLEKVQQSNGDRKHSSDENNVSFSHLCLVGNPVLKNINLNIEK Walker A                                        F508
human   451 GQLLAVAGSTGAGKTSLLMMIMGELEPSEGKIKHSGRISFCSQFSWIMPGTIKENIIFGVSYDEYRYRSVIKACQLEEDISKFAEKDNIV
pig     451 GQLLAVAGSTGAGKTSLLMMIMGELEPSEGKIKHSGRISFCSQFSWIMPGTIKENIIFGVSYDEYRYRSVIKACQLEEDISKFAEKDNIV
mouse   451 GEMLAITGSTGSGKTSLLMLILGELEASEGIIKHSGRVSFCSQFSWIMPGTIKENIIFGVSYDEYRYKSVVKACQLQQDITKFAEQDNTV SM                 Walker B
human   541 LGEGGITLSGGQRARISLARAVYKDADLYLLDSPFGYLDVLTEKEIFESCVCKLMANKTRILVTSKMEHLKKADKILILHEGSSYFYGTF
pig     541 LGEGGITLSGGQRARISLARAVYKDADLYLLDSPFGYLDVLTEKEIFESCVCKLMANKTRILVTSKMEHLKKADKILILHEGSSYFYGTF
mouse   541 LGEGGVTLSGGQRARISLARAVYKDADLYLLDSPFGYLDVFTEEQVFESCVCKLMANKTRILVTSKMEHLRKADKILILHQGSSYFYGTF R domain
human   631 SELQNLQPDFSSKLMGCDSFDQFSAERRNSILTETLHRFSLEGDAPVSWTETKKQSFKQTGEFGEKRKNSILNPINSIRKFSIVQKTPLQ
pig     631 SELQSQRPDFSSKLMGYDTFDQFTAERRNSIITETLRRFSLEGDASVSWNETKKQSFKQTGEFGEKRKNSILNSINSIRKFSIVQKTPLQ
mouse   631 SELQSLRPDFSSKLMGYDTFDQFTEERRSSILTETLRRFSVDDSSAPWSKPK--QSFRQTGEVGEKRKNSILNSFSSVRKISIVQKTPLQ human   721 MNGIEEDSDEPLERRLSLVPDSEQGEAILPRISVISTGPTLQARRRQSVLNLMTHS-VNQGQNIHRKTTASTRKVSLAPQANLTELDIYS
pig     721 MNGFEEDSGEPLERRLSLVPDSEHGEAILPRSNVINAGPTFQGRRRQSVLNLMTRSSVNQGQSIHRKTATSTRKMSLVPQANLTEIDIYS
mouse   719 IDGESDDLQ----EKRLSLVPDSEQGEAALPRSNMIATGPTFPGRRRQSVLDLMTFT-PNSGSSNLQRTRTSIRKISLVPQISLNEVDVYS TM7
human   810 RRLSQETGLEISEEINEEDLKECFFDDMESIPAVTTWNTYLRYITVHKSIIFVLIWCLVIFLAEVAASLVVLWLLGNTPLQDKGNSTHSR
pig     811 RRLSQDTGLEISEEINEEDLRECFSDDVESIPTVTTWNTYLRYVTVHKSILFVLIWCLVVFLAEVAACLVVLCLLKKTSPQDKGNSTKGA
mouse   805 RRLSQDSTLNITEEEINEEDLKECFIDDVIKIPPVTTWNTYLRYFTLHKGILLVLIWCVLFLVEVAASLFVWLLKNNPVNSGNNGTKIS TM8
human   900 NNSYAVIITSTSSYYVFYIYVGVADTLLAMGFFRGLPLVHTLITVSKILHHKMLHSVLQAPMSTLNTLKAGGILNRFSKDIAILDDLLPL
pig     901 NNSYAVIITSTSAYYVFYIYVGVADGLLALGLFRGLPLVHTLITVSKILHRKMLHSVLQAPMSTLNTLKAGGILNRFSKDIAVLDDLLPL
mouse   895 NSSYVIIITSTSFYYIFYIYVGVADTLLALSLFRGLPLVHTLITASKILHRKMLHSILHAPMSTISKLKAGGILNRFSKDIAILDDFLPL TM9          TM10
human   990 TIFDFIQLLLIVIGAIAVVAVLQLYIFVATVPVIVAFIMLRAYFLQTSQQLKQLESEGRSPIFTHLVTSLKGLWTLRAFGRQPYFETLFH
pig     991 TIFDFIQLLLIVIGAVAVVSVLKLYIFLATVPVIVVFILLRAYFIHTSQQLKQLESEGRSPIFTHLITSLKGLWTLRAFGRQPYFETLFH
mouse   985 TLFDFIQLVFEIVIGAIIVVSALKFYIFLATVPGLVVFILLRAYFIHTAQQLKQLESEGRSPIFTHLVTSLKGLWTLRAFRRQTYFETLFH TM11                          TM12
human  1080 KALNLHTANWFLYLSTLRWFQMRIEMIFVIFFIAVTFISILTTGEGEGRVGIILTLAMNIMSTLQWAVNSSLDVDSLMRSVSRVFKFIDM
pig    1081 KALNLHTANWFLYLSTLRWFQMRIEMIFVIFFIAVTFISILTTGEGEGTVGIILTLAMNIMSTLQWAVNSSLDVDSLMRSVSRVFKFIDM
mouse  1075 KALNLHTANWFMYLATLRWFQMRLDMIFVLFFIVVTFISILTTGEGTAGIILTLAMNIMSTLQWAVNSSIDTDSLMRSVSRVFKFIDI NBD2                                                                  Walker A
human  1170 PTEGK-PTKSTKPYKNGQLSKVMIIENSHVKKDDIWPSGGQMTVKDLTAKYTEGGNAILENISFSISPGQRVGLLGRTGSGKSTLLSAFL
pig    1171 PAEGDQPNRSFKPSKDGQLSKVMIIENQHVKKSDIWPSGGQMTVKDLTAKYVDGGNAVLENISFSISPGQRVGLLGRTGSGKSTLLAFL
mouse  1165 QTEESMYTQIIKELPREGSSDVLVIKNEHVKKSDIWPSGGEMVVKDLTVKYMDDGNAVLENISFSISPGQRVGLLGRTGSGKSTLLSAFI SM
human  1259 RLLNTEGEIQIDGVSWDSITLQQWRKAFGVIPQKVFIFSGTFRKNLDPYEQWSDQEIWKVADEVGLRSVIEQFPGKLDFVLVDGGCVLSH
pig    1261 RLLNTEGEIQVDGVSWDSITLQQWRKAFGVIPQKVFIFSGTFRKNLDPYGQWNDQEIWKVAEEVGLRSVIEQFPGKLDFVLVDGGCVLSH
mouse  1255 RMLNIKGDIEIDGVSWNSVTLQEWRKAFGVITQKVFIFSGTFRQNLDPNGKWKDEEIWKVADEVGLKSVIEQFPGQLNFTLVDGGYVLSH Walker B
human  1349 GHKQLMCLARSVLSKAKILLLDEPSAHLDPVTYQIIRRTLKQAFADCTVILCEHRIEAMLECQQFLVIEENKVRQYDSIQKLLNERSLFR
pig    1351 GHKQLMCLARSVLGKAKILLLDEPSAHLDPITYQIIRRTLKQAFADCTVILSEHRIEAMLECQRFLVIEENKVRQYDSIQRLLSEKSLFR
mouse  1345 GHKQLMCLARSVLSKAKIILLDEPSAHLDPITYQVIRRVLKQAFAGCTVILCEHRIEAMLDCQRFLVIEESNVWQYDSLQALLSEKSIFR human  1439 QAISPSDRVKLFPHRNSSKCKSKPQIAALKEETEEEVQDTRL
pig    1441 QAISPDRLKLLPHRNSSKQRSRSKIAALKEETEEEVQETRL
mouse  1435 QAISSSEKMRFFQGRHSSKHKPRTQITALKEETEEEVQETRL
```

TRANSGENIC PORCINE MODELS OF CYSTIC FIBROSIS

CROSS-REFERENCE TO RELATED APPLICATIONS

This application is a continuation-in-part of, and claims priority from, U.S. Ser. No. 12/074,632, filed Mar. 5, 2008, now U.S. Pat. No 7,989,675, which claims the benefit of the filing date of U.S. Ser. No. 60/908,637, filed Mar. 28, 2007, and U.S. Ser. No. 60/966,971, filed Aug. 30, 2007. The contents of each of the prior applications are incorporated herein by reference.

STATEMENT AS TO FEDERALLY SPONSORED RESEARCH

This invention was made with government support under grant number HL51670 awarded by the National Heart Lung and Blood Institute, and grant number DK547759 awarded by the National Institute of Diabetes and Digestive and Kidney Diseases. The government has certain rights in this invention.

FIELD OF THE INVENTION

This invention relates to transgenic, non-human animal models of disease, cells that can be used to make such animals, and methods of making and using these animals and cells.

BACKGROUND OF THE INVENTION

Many human diseases and conditions are caused by gene mutations. Substantial effort has been directed towards the creation of transgenic animal models of such diseases and conditions, to facilitate the testing of approaches to treatment, as well as to gain a better understanding of disease pathology. Early transgenic animal technology focused on the mouse, while more recent efforts, which have been bolstered by the development of somatic cell nuclear transfer, have included larger animals, including pigs, cows, and goats. This technology has resulted in the production of, for example, pigs in which the gene encoding α-1,3-galactosyltransferase has been knocked out, in efforts to generate organs that can be used in xenotransplantation (see, e.g., Lai et al., Science 295:1089-1092, 2002). Additional applications of this technology include the production of large quantities of human proteins (e.g., therapeutic antibodies; see, e.g., Grosse-Hovest et al., Proc. Natl. Acad. Sci. U.S.A. 101(18):6858-6863, 2004). Substantial benefits may be obtained by the use of somatic cell nuclear transfer technology in the production of large animal models of human disease.

An example of a disease caused by gene mutations is cystic fibrosis (CF), which is an inherited disease that affects many organs of the body, including the lungs, pancreas, sweat glands, liver, and organs of the reproductive tract. The disease is characterized by abnormalities in fluid secretion, which can lead to diverse physiological problems. For example, in the lungs of CF patients, secreted mucus is unusually heavy and sticky, and thus tends to clog small air passages, making it difficult for patients to breath and leading to bacterial infection and inflammation. Repeated lung infections and blockages in CF patients can cause severe, permanent lung damage. Other features of CF arise from the clogging of ducts leading from the pancreas to the small intestine, which blocks the transport of critical digestive enzymes such as amylase, protease, and lipase. This can lead to problems including incomplete digestion, diarrhea, bowel blockage, and weight loss. Digestive complications of CF can also be caused by blockage of liver bile ducts. Due to these and other features of the disease, CF causes progressive disability in patients and ultimately leads to early death.

CF is caused by the presence of a mutation in the gene encoding the cystic fibrosis transmembrane conductance regulator (CFTR) protein, which is a chloride channel found in the membranes of epithelial cells lining passageways of the lungs, liver, pancreas, intestines, and digestive tract, and in the skin. The disease is autosomal recessive, and thus CF patients have mutations in both CFTR alleles, while asymptomatic CF carriers have mutations in only one allele. There are more than 1,200 different known mutations of the CFTR gene that can lead to cystic fibrosis in humans, with some mutations causing milder symptoms than others. However, about 70% of people with CF have the disease due to a particular gene mutation, a deletion of three nucleotides, leading to the loss of a phenylalanine that is normally present at position 508 of the CFTR protein. This form of the disease, often referred to as ΔF508 (CFTR-ΔF508, also called F508del-CFTR), is both the most common and the most severe form of the disease. The loss of phenylalanine at position 508 results in improper CFTR protein folding, which causes retention of the mutant protein in the ER and targets it for degradation before it even reaches the cell membrane. Additionally, this deletion alters channel gating, reducing the rate of channel opening.

There is no cure for CF. Current approaches to treatment include the use of mucous thinning drugs, digestive enzyme supplementation, bronchodilators, respiratory therapy, antibiotics, and lung transplantation. Even given the availability of these approaches to treatment, as the disease progresses, patients typically suffer from an increasingly poor quality of life. New approaches to treating diseases such as CF, which may be identified, for example, by the use of large animal models, are therefore needed for this and other devastating diseases.

SUMMARY OF THE INVENTION

The invention provides large, non-human animal models of human diseases or conditions, in which one or more genes associated with the diseases or conditions include one or more targeted mutations or are inactivated. The animals of the invention can be, for example, ungulates such as, e.g., pigs, cows, sheep, and goats. In one example, the disease or condition is cystic fibrosis and the gene including one or more mutations is a cystic fibrosis membrane transporter gene (CFTR).

The animal models of the invention can include the mutation(s) in one or both alleles of the gene in the genome of the transgenic animal, and the mutation(s) can result in full or partial inactivation of the gene(s). In one example, the mutation includes an insertion of an exogenous nucleic acid molecule and/or a transcription termination sequence. In another example, the mutation substantially eliminates expression of a functional gene product of the targeted gene in cells in which such expression normally takes place, absent the mutation. In the case of an animal with a mutation or mutations in both alleles of a gene, the mutation or mutations in each allele can be identical to one another or can be different.

The animal models of the invention may optionally include a homologous transgenic copy of a wild-type or mutated gene from a different animal. The animal models may thus include, for example, in addition to a mutation/inactivation of an endogenous gene, an inserted copy of a corresponding gene from another species. Thus, for example, an animal (such as a pig) in which an endogenous CFTR gene is mutated or inactivated may be modified to include a CFTR gene from another animal (such as a human), which may be wild-type or may include a mutation (e.g., CFTR-Δ508). The invention therefore provides transgenic, large non-human animal models of human diseases and conditions (e.g., pigs), in which one or more endogenous genes associated with the diseases or conditions are knocked-out (i.e., genetically altered in such way as to inhibit the production or function of the product of the gene) and replaced with a homologous wild-type or mutated gene derived from a different animal (e.g., a human). In one example, a pig with its endogenous porcine CFTR knocked-out expresses a human transgene encoding a CFTR gene, such as the CFTR-Δ508 gene.

Examples of CFTR mutations that can be included in the animals (and cells) of the invention include (i) class I mutations, which result in little or no mRNA production, and thus little or no protein production (e.g., nonsense mutation (e.g., G542X), a frameshift mutation (e.g., 394delTT), a splice junction mutation (e.g., 1717-1 GtoA)), (ii) class II mutations, which result in a protein trafficking defect where CFTR is made, but fails to traffic to the cell membrane (e.g., F508del), (iii) class III mutations, which result in CFTR trafficking to the cell membrane, but failing to be properly regulated or responding to cAMP stimulation (e.g., G551D, which fails to respond to cAMP stimulation), (iv) class IV mutations, which result in a CFTR channel function defect (e.g., R117H), and (v) class V mutations, which cause CFTR synthesis defects, resulting in reduced synthesis or defective processing of normal CFTR (e.g., missense mutation (e.g., A455E), or a mutation introduced by alternative splicing (e.g., 3849+10 kbC→T). Additional mutations include 621+1→T, W1282X, R347P, S549I,N,R(A→C), R553X, and N1303K.

In the case of animals having CFTR mutations, the animals may be characterized by one or more (e.g., 2, 3, 4, 5, or 6) phenotypic characteristics, such as the phenotypic characteristics of the CFTR−/− pigs described below. Thus, for example, the animals may be characterized by one or more phenotypic characteristics selected from the group consisting of: (i) an electrophysiological phenotype similar to that of human cystic fibrosis, (ii) meconium ileus, (iii) exocrine pancreatic insufficiency or abnormalities, (iv) hepatic abnormalities, (v) gall bladder and/or bile duct abnormalities, and (vi) lack of abnormalities in vas deferens or lungs at birth.

The invention also provides isolated cells of transgenic, large non-human animal models of human diseases or conditions, in which one or more genes associated with the diseases or conditions include one or more targeted mutations. The animals can be, for example, ungulates, such as, e.g., pigs, cows, sheep, and goats. In one example, the disease or condition is cystic fibrosis and the gene including one or more mutations is a cystic fibrosis membrane transporter gene.

The cells of the invention can include the mutation(s) in one or both alleles of the genes in the genomes of the cells, and the mutation(s) can results in full or partial inactivation of the gene(s). In one example, the mutation includes an insertion of an exogenous nucleic acid molecule and/or a transcription termination sequence. In another example, the mutation substantially eliminates expression of a functional gene product of the targeted gene in cells in which such expression normally takes place, absent the mutation. In the case of a cell with a mutation or mutations in both alleles of a gene, the mutation or mutations in each allele can be identical to one another or can be different. In one example, the cells are fetal cells, such as fetal fibroblasts. The cells may include a homologous transgenic copy of a wild-type or mutated gene from a different animal, such as a human, as described above. Additional examples of cell types included in the invention are provided below.

The invention further provides methods of making transgenic, large non-human animal models of diseases or conditions, as described above and elsewhere herein. The methods can include the steps of: (i) introducing one or more mutations into an allele of one or more genes associated with a disease or condition in a cell (e.g., a fetal fibroblast) to generate a donor cell; (ii) introducing the nucleus of the donor cell into a recipient cell (e.g., an enucleated oocyte) to generate an embryo; and (iii) transferring the embryo into a surrogate female to generate the transgenic, large non-human animal model. The animals can be, for example, ungulates, such as, e.g., pigs, cows, sheep, and goats. In one example, the disease or condition is cystic fibrosis and the gene including one or more mutations is a cystic fibrosis membrane transporter gene. In a variation of these methods, the donor cell includes one or more mutations in one allele of a gene, and the method is carried out to introduce one or more mutations into the other allele. In another example, the donor cell includes a homologous transgenic copy of a wild-type or mutated gene from a different animal (e.g., a human), as described above. In a further example, the methods further involve breeding an animal that is born from the surrogate female to obtain a homozygous mutant.

The invention also includes methods of identifying therapeutic agents that can be used in the treatment of diseases or conditions (e.g., cystic fibrosis). These methods involve administering one or more candidate therapeutic agents to a transgenic animal, as described above, and monitoring the animal for one or more symptoms of the disease or condition (e.g., one or more phenotypic characteristics of CF models of the invention, as described herein). Detection of improvement in a symptom of the disease or condition indicates the identification of a compound that can be used in the treatment of the disease or condition.

The invention further provides methods of targeting the introduction of mutations into pig cells. These methods involve the steps of providing pig cells (e.g., fetal fibroblasts), using an adeno-associated viral vector to deliver a gene targeting construct to the isolated pig cells, in the absence of cell detachment and reattachment, and selecting gene-targeted clones. The cells are in culture for 30 days or less (e.g., 20 days or less; see below) during the targeting construct delivery and selection steps. These methods can be used, for example, for the introduction of a mutation into a cystic fibrosis transmembrane conductance regulator gene (e.g., the ΔF508 mutation) in the pig cell. Information concerning other examples of mutations that can be used in the invention, as well as the use of the present methods to inactivate or replace genes (e.g., to replace pig genes with human genes), is provided below.

By "donor cell" is meant a cell from which a nucleus or chromatin material is derived, for use in nuclear transfer. As is discussed elsewhere herein, nuclear transfer can involve transfer of a nucleus or chromatin only, as isolated from a donor cell, or transfer of an entire donor cell including such a nucleus or chromatin material.

By "genetic modification," "mutation," or "disruption" of a gene (e.g., a CFTR gene) is meant one or more alterations in gene sequences (including coding sequences and non-coding sequences, such as introns, promoter sequences, and 5' and 3'-untranslated sequences) that alter the expression or activity of this gene by, for example, insertion (of, e.g., heterologous sequences, such as selectable markers, and/or termination signals), deletion, frame shift mutation, silent mutation, nonsense mutation, missense mutation, point mutation, or combinations thereof. In one example, the amino acid sequence encoded by the nucleic acid sequence has at least one amino acid altered as compared to a naturally-occurring sequence. Examples of mutations include the insertion of a polynucleotide into a gene, the deletion of one or more nucleotides from a gene, and the introduction of one or more base substitutions into a gene. Preferred modifications of CFTR sequences are those that lead to one or more features of CF in transgenic animals including a mutation in, or disruption of, both CFTR alleles. As is discussed elsewhere herein, the modifications in the two CFTR alleles of such animals can be identical or different. Further, the modifications can result in a complete lack of functional CFTR production (as in the human ΔF508 mutation), or can result in diminished functional CFTR production, as may be characteristic of less severe forms of the disease.

Examples of such mutations include but are not limited to: i) class I mutations, which result in little or no mRNA production, and thus little or no protein production (e.g., nonsense mutations, G542X; frameshift mutations, 394delTT; and splice junction mutations, 1717-1 GtoA), ii) class II mutations, which result in a protein trafficking defect where CFTR is made, but fails to traffic to the cell membrane (e.g., F508del), iii) class III mutations, which are those in which CFTR traffics to the cell membrane, but fails to be properly regulated (e.g., G55 ID, which fails to respond to cAMP stimulation), iv) class IV mutations, which result in a CFTR channel function defect (e.g., R117H), and v) class V mutations, which cause CFTR synthesis defects, resulting in reduced synthesis or defective processing of normal CFTR (e.g., missense mutations, A455E; alternative splicing, 3849+ 10 kbC to T).

In one example, a mutation is introduced by the insertion of a polynucleotide (e.g., a positive selection marker, such as an antibiotic resistance gene (e.g., a neomycin resistance gene)) into an endogenous gene. Optionally, a mutation that is introduced into such an endogenous gene reduces the expression of the gene. If desired, the polynucleotide may also contain recombinase sites flanking the positive selection marker, such as loxP sites, so that the positive selection marker may be removed by a recombinase (e.g., cre recombinase).

By "homologous" genes is meant a pair of genes from two animal species that encode proteins having similar functional and physical properties. The proteins encoded by homologous genes are often very similar in structure and function (although not always), and typically have a common evolutionary origin. The sequence identity is typically equal to or greater than 80% between two gene homologs. One example of a homologous gene pair is the porcine CFTR and human CFTR gene locus.

By "homozygous knock-out non-human mammal" is meant a mammal other than a human in which the two alleles of an endogenous gene (such as the CFTR gene) have been genetically targeted, resulting in a marked reduction or elimination of expression of a functional gene product, which is achieved by gene deletion or disruption. According to this invention, the genetic targeting event at both alleles may or may not be the same. Thus, a non-human mammal, in which the two alleles of an endogenous gene (such as a CFTR gene) have been genetically targeted by two different targeting vectors resulting in the null expression of the gene, would be considered as being a homozygous knock-out non-human mammal. An example of a "knock-in mutation" is one resulting in the insertion of a mutation into an endogenous gene, for example, introducing the ΔF508 or another CF mutation into a CFTR gene.

By animal "knock-out" is meant an animal (e.g., a pig or mouse; also see other animals described herein) having a genome in which the function of a gene has been disrupted, or "knocked-out." A common method of producing disabled genes using recombinant DNA technology involves inserting an antibiotic resistance gene into the normal DNA sequence of a clone of the gene of interest by homologous recombination. This disrupts the action of the gene, thereby preventing it from leading to the production of an active protein product. A cell (or cell nucleus) in which this transfer is successful can be injected into a recipient cell (e.g., an enucleated oocyte) to generate a transgenic animal by nuclear transfer. In another approach, the cell is injected into an animal embryo, producing a chimeric animal. These animals are bred to yield a strain in which all of the cells contain the knocked-out gene.

By "recipient cell" is meant a cell into which a donor cell, a donor cell nucleus, or donor cell chromatin is introduced. Preferably, recipient cells are enucleated prior to nuclear transfer. Examples of recipient cells include oocytes, fertilized zygotes, and two-cell embryos.

By "transgenic, large non-human animal" is meant any non-human animal that includes a genetic modification, as defined herein. Examples of such animals include animals other than mice such as, for example, ungulates. Examples of ungulates that can be used in the invention include members of the orders Perissodactyla and Artiodactyla, such as any members of the family Suidae, and in particular any member of the genus *Sus*, such as *Sus scrofa*, which is also known as the domestic pig or a subspecies thereof (*Sus scrofa domestica*). In addition to porcine ungulates, additional ungulates that can be used in the invention include bovine, ovine, and caprine ungulates. Thus, for example, the invention can include the use of cows (e.g., *Bos taurus* or *Bos indicus*), sheep, goats, buffalos, antelopes, oxen, horses, donkeys, mule, deer, elk, caribou, water buffalo, camels, llama, alpaca, and elephants.

The invention provides several advantages, as it provides large, non-human animal models that can be used in the identification and characterization of therapies for genetic diseases. One example of such a disease is cystic fibrosis which, as discussed above, is a devastating disease, leading to increased levels of disability and, eventually, early death. Despite progress in understanding and treating CF, the pathogenesis of the disease is not well understood and therapies remain inadequate. A major impediment to answering questions is the lack of an animal model that shows disease similar to that in humans. Availability of a CF pig will allow investigators to address key problems that have persisted unresolved for years. As a result, it will be possible to develop new treatments, therapies, and preventions.

Further, given the close physiological relationship between humans and large animals, such as pigs, there is an increased likelihood that results obtained using the animal models of the invention can be applied to humans, relative to other animal models (e.g., mice, which do not develop the airway and pancreatic disease typical of human CF). Specifically with respect to pigs, it is noted that pigs and humans have anatomical, histological, biochemical, and physiologic similarities. Further, pigs and humans possess similar abundance of submucosal glands and glycoprotein synthesis/secretion. In addition, pigs and humans have similar respiratory immune systems and pulmonary inflammatory responses, making the pig be a particularly good model for CF disease of humans. Further, the use of human sequences in large animals such as pigs, as in some examples of the invention, provides additional benefits of providing a system that is very similar to that of humans. Indeed, the data described below show the close similarities between human CF and the pig CFTR−/− model of the invention. The invention thus can be used to provide substantial benefits in the treatment of diseases and conditions caused by or associated with gene mutations, such as cystic fibrosis.

Other features and advantages of the invention will be apparent from the drawings, the detailed description, the experimental examples, and the claims.

BRIEF DESCRIPTION OF THE DRAWINGS

The application file contains drawings executed in color (FIGS. 2, 7, 10, 12-17, 20, and 22). Copies of this patent or patent application with color drawings will be provided by the Office upon request and payment of the necessary fee

FIG. 14 shows that the lungs of newborn CFTR−/− and CFTR+/+ piglets appear normal. A) Microscopic appearance of lung from piglets <12 hours old. H&E staining. Bars, 1 mm (left) and 50 µm (right). B) Bronchial epithelia and submucosal glands. H&E staining. Bars, 50 µm. Images are representative of lack of lesions in 15 of 15 CFTR−/−.

FIG. 17 is an amino acid sequence alignment of human, pig, and mouse CFTR. Transmembrane domains (TM), nucleotide-binding domains (NBD), and the R domain are boxed and labeled. Walker A and B motifs, signature motifs (SM), and F508 are shaded. The alignment was generated using ClustalW. The NBD boundaries are based on the NBD1 crystal with the NBD2 boundaries based on amino acids counting up from Walker A and down from Walker B.

DETAILED DESCRIPTION OF THE INVENTION

Figure 1:
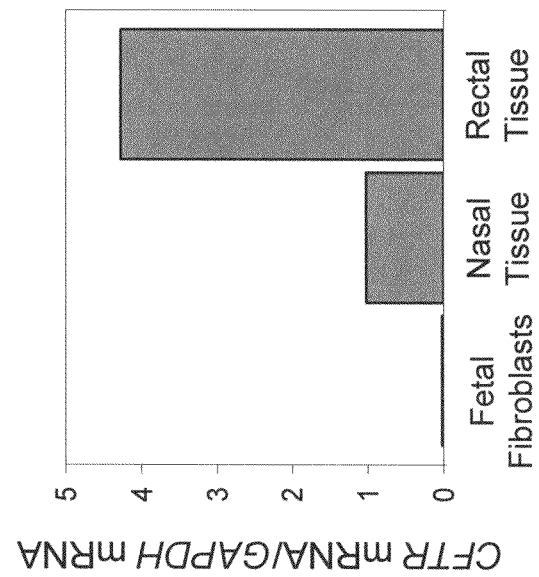
FIG. 1 is a graph showing CFTR expression in pig fetal fibroblasts. Data are quantitative RT-PCR of pig CFTR mRNA relative to GAPDH in primary pig fetal fibroblasts, nasal epithelia, and rectal epithelia. Similar results were obtained on two other occasions.

The invention provides animal models of human diseases (e.g., cystic fibrosis (CF)) and conditions, which can be used in methods including the identification and characterization of approaches for treating the diseases and conditions. As is discussed further below, the animal models of the invention are large, non-human animals, such as pigs, which have been genetically modified to include one or more mutations in a gene associated with a particular disease or condition (e.g., the cystic fibrosis transmembrane regulator (CFTR) gene in CF). The genetic modifications can result in the animals having one or more symptoms characteristic of the disease or condition. Animals exhibiting such symptoms are particularly advantageous in the development of therapeutic approaches, as candidate drugs and other approaches to treatment can be evaluated for effects on the symptoms in such animals. Thus, in addition to the animal models themselves, the invention also provides methods of using the animals for identifying and characterizing treatments. Further, the invention includes methods of making transgenic, large non-human animal models and cells that can be used in these methods. The animal models systems, methods, and cells of the invention are described further, below.

In addition to animals including knock-outs or mutations in endogenous genes, the invention also includes transgenic, large non-human animal models of human diseases and conditions (e.g., pigs), in which one or more endogenous genes associated with the diseases or conditions are knocked-out (i.e., genetically altered in such way as to inhibit the production or function of the products of these genes) and replaced with a comparable wild-type or mutated gene derived from a different animal (e.g., a human). In one example, a pig with its endogenous porcine CFTR knocked-out expresses a human transgene encoding a mutated CFTR protein, such as the CFTR-Δ508 gene (i.e., a CFTR−/−, hCFTR-ΔF508 pig). Alternatively, the human transgene may encode a normal, wild-type copy of a gene of interest (e.g., CFTR). These embodiments of the invention are especially useful for the generation of non-human animal models of human diseases and conditions that can be used to test existing and potential therapeutics that may only (or may preferentially) modulate or treat the disease when contacting, or being in the presence of, human copies of the disease gene or protein in question.

The invention is described herein in reference to animal models of CF, which are generated by mutation, deletion, or replacement of the CFTR gene. However, the methods of the invention are also applicable to the development of animal models of additional diseases and conditions, examples of which are provided below.

The transgenic animals of the invention can be made using the following general strategy. Briefly, the genome of a cell (e.g., a fetal fibroblast) from an animal of interest, such as a pig, is genetically modified or replaced by, for example, gene targeting by homologous recombination, to create a "donor cell." According to the methods of the invention, the genetic modification results in at least partial inactivation of an endogenous gene associated with a particular disease or condition (e.g., a CFTR gene in CF), as will be described in further detail below. The nucleus of such a genetically modified donor cell (or the entire donor cell, including the nucleus) is then transferred into a so-called "recipient cell," such as an enucleated oocyte. After activation and, typically, a brief period of in vitro culture, the resulting embryo is implanted into a surrogate female in which development of the embryo proceeds. Typically, the donor cell, oocyte, and surrogate female are of the same species, but the sources can be different species, as is known in the art.

Details of methods for making large genetically modified animals, such as pigs, according to the invention, are provided below. Additional information concerning methods for making genetically modified pigs and other large animals is known in the art and can also be adapted for use in the present invention (see, e.g., US 2005/0120400 A1; U.S. Pat. No. 5,995,577; WO 95/16670; WO 96/07732; WO 97/00669; WO 97 00668; WO 2005/104835; Lai et al., Reproductive Biology and Endocrinology 1:82, 2003; Hao et al., Transgenic Res. 15:739-750, 2006; Li et al., Biology of Reproduction 75:226-230, 2006; Lai et al., Nature Biotechnology 24(4): 435-436, 2006; Lai et al., Methods in Molecular Biology 254(2):149-163, 2004; Lai et al., Cloning and Stem Cells 5(4):233-241, 2003; Park et al., Animal Biotechnology 12(2): 173-181, 2001; Lai et al., Science 295:1089-1092, 2002; Park et al., Biology of Reproduction 65:1681-1685, 2001; the contents of each of which are incorporated herein by reference).

The transgenic animals of the invention can be any non-human mammals, including, for example, ungulates. Examples of ungulates that can be used in the invention include members of the orders Perissodactyla and Artiodactyla, such as any members of the family Suidae, and in particular any member of the genus *Sus*, such as *Sus scrofa*, which is also known as the domestic pig or a subspecies thereof (*Sus scrofa domestica*). In one specific example, the animal is a miniature swine that is a descendent from the miniature swine described by Sachs et al., Transplantation 22:559, 1976. In addition to porcine ungulates, additional ungulates that can be used in the invention include bovine, ovine, and caprine ungulates. Thus, for example, the invention can include the use of cows (e.g., *Bos taurus* or *Bos indicus*), sheep, goats, buffalos, antelopes, oxen, horses, donkeys, mule, deer, elk, caribou, water buffalo, camels, llama, alpaca, and elephants.

The invention includes animals in which only one allele of a targeted gene (e.g., CFTR) is disrupted, mutated, or replaced with the other allele remaining unaffected. These animals, which are referred to herein as "heterozygous" or "hemizygous" animals, can be used, for example, in breeding approaches to generate homozygous mutants, if desired, for example, in the case of diseases caused by homozygous recessive mutations. These animals can also be used as animal models themselves, in the case of diseases caused by autosomal dominant mutations.

Also included in the invention are homozygous mutant animals, in which both alleles of a target gene (e.g., CFTR) are disrupted or mutated, by the same or different mutations (or replaced with the same or different gene(s), optionally with the same or different mutations). In addition to being obtainable by breeding approaches involving hemizygous animals, homozygous mutant animals can also be obtained using an approach in which a cell (e.g., a fetal fibroblast) including a mutation in one allele, such as a cell obtained from an animal produced using the method summarized above, is subjected to gene targeting by homologous recombination to achieve modification of the remaining allele. The resulting donor cell can then be used as a source of a modified nucleus for nuclear transfer into a recipient cell, such as an enucleated oocyte, leading to the formation of a homozygous mutant embryo which, when implanted into a surrogate female, develops into a homozygous mutant animal.

A target gene (e.g., a CFTR gene) can be subject to genetic modification in any appropriate cell type of a species for which it is desired to create an animal model of a disease associated with mutation of the gene, according to the invention. As is understood in the art, it is necessary to be able to culture and carry out homologous recombination in a cell that is to be used as a donor cell. A particular example of such a cell, which is described in more detail below in connection with pigs, in the experimental examples, is the fetal fibroblast. These cells can be obtained using, for example, the approach described in U.S. Patent Application Publication 2005/0120400 and other references cited herein.

The invention also includes the use of other cell types that may be present in the cell preparations obtained using the method described in U.S. Patent Application Publication 2005/0120400. Additional examples of cells that can be used as donor cells in making the transgenic animals of the invention include other fetal cells, placental cells, or adult cells. Specific examples of such cells for gene targeting include differentiated cells such as fibroblasts, epithelial cells, neural cells, epidermal cells, keratinocytes, hematopoietic cells, melanocytes, chondrocytes, B-lymphocytes, T-lymphocytes, erythrocytes, macrophages, monocytes, placental, and muscle cells.

If a cell to be genetically altered is derived from an embryo or a fetus, the cell (e.g., a fetal cell or placental cell) can be isolated at any time during the gestation period until the birth of the animal, which may or may not be itself genetically altered. In the case of a pig, such cells can be obtained, for example, between 20 to 90 days of gestation, between 25 to 60 days of gestation, between 30 to 45 days of gestation, or between 35 to 40 (e.g., at 35 days) of gestation. The time periods for obtaining cells from other animals is known in the art (see, e.g., WO 2005/104835).

Gene targeting carried out to make the cells and animals of the invention can result in gene inactivation by disruption, removal, modification, or replacement of target gene sequences. For example, inactivation can take place by the insertion of a heterologous sequence and/or a stop codon into a target gene. A specific example of this type of inactivation, in the context of a CFTR gene, is described in the experimental examples, below. As is known in the art, inserted sequences can replace previously existing sequences in a gene or can be added to such sequences, depending on the design of the targeting construct. Also as is known in the art, the design of targeting constructs can be altered, depending upon whether it is desired to completely knock out the function of a gene or to maintain some level of reduced function. In the case of CFTR, for example, complete knock out of function is consistent with the most common form of CF (ΔF508; see above), but other, less dramatic changes may be desirable for the generation of models of disease maintaining some CFTR function. Such changes may be achieved by, for example, replacement with sequences that are identical to wild-type sequences, except for the presence of specific mutations giving rise to features of the target disease. In other approaches, coding sequences are not altered or are minimally altered and, rather, sequences impacting expression of a target gene, such as promoter sequences, are targeted. In any case, selectable marker insertion is often desirable to facilitate identification of cells in which targeting has occurred. If desired, such markers or other inserted sequences can later be removed by, e.g., cre-lox or similar systems.

A CFTR−/− (i.e., knock-out), hCFTR-ΔF508 pig can be made numerous ways, including, but not limited to: i) introducing a human CFTR-ΔF508 cDNA, partial human CFTR-ΔF508 gene, or entire human CFTR-ΔF508 gene into pig CFTR−/− cells, selecting for human CFTR-ΔF508 expression, and using these cells as nuclear donors in somatic cell nuclear transfer, and ii) introducing a human CFTR-ΔF508 cDNA, partial human CFTR-ΔF508 gene, or entire human CFTR-ΔF508 gene into pig CFTR−/− into matured oocytes, fertilizing, then transferring to a recipient female. The human CFTR sequence is described, for example, by Riordan et al., Science 245(4922):1066-1073, 1989 (erratum in Science 245 (4925):1437, 1989)). Human, pig, and mouse CFTR sequences are also provided in SEQ ID NOs: 1-6.

As is known in the art, targeted gene modification requires the use of nucleic acid molecule constructs having regions of homology with a targeted gene (or flanking regions), such that integration of the construct into the genome alters expression of the gene, either by changing the sequence of the gene and/or the levels of expression of the gene. Thus, to alter a gene, a targeting construct is generally designed to contain three main regions: (i) a first region that is homologous to the locus to be targeted (e.g., the CFTR gene or a flanking sequence), (ii) a second region that is a heterologous polynucleotide sequence (e.g., encoding a selectable marker, such as an antibiotic resistance protein) that is to specifically replace a portion of the targeted locus or is inserted into the targeted locus, and (iii) a third region that, like the first region, is homologous to the targeted locus, but typically is not contiguous with the first region of the genome. Homologous recombination between the targeting construct and the targeted wild-type locus results in deletion of any locus sequences between the two regions of homology represented in the targeting vector and replacement of that sequence with, or insertion into that sequence of, a heterologous sequence that, for example, encodes a selectable marker. In the case of targeting transcriptionally inactive genes, such as, for example, the CFTR gene in fibroblasts, or a gene having only very low levels of transcription, the constructs of the invention can include a promoter, such as a PGK promoter, which drives expression of the selectable marker (e.g., Neo). Use of such promoters may not be required in cases in which transcriptionally active genes are targeted, if the design of the construct results in the marker being transcribed as directed by an endogenous promoter. Exemplary constructs and vectors for carrying out such targeted modification are described herein. However, other vectors that can be used in such approaches are known in the art and can readily be adapted for use in the invention.

In order to facilitate homologous recombination, the first and third regions of the targeting vectors (see above) include sequences that exhibit substantial identity to the genes to be targeted (or flanking regions). By "substantially identical" is meant having a sequence that is at least 80%, 90%, 95%, 98%, or 100% identical to that of another sequence. Sequence identity is typically measured using BLAST® (Basic Local Alignment Search Tool) or BLAST® 2 with the default parameters specified therein (see, Altschul et al., J. Mol. Biol. 215:403-410, 1990; Tatiana et al., FEMS Microbiol. Lett. 174:247-250, 1999). These software programs match similar sequences by assigning degrees of homology to various substitutions, deletions, and other modifications. Thus, sequences having at least 80%, 90%, 98%, 99%, or even 100% sequence identity with the targeted gene loci can be used in the invention to facilitate homologous recombination.

The total size of the two regions of homology (i.e., the first and third regions noted above) can be, for example, approximately 2-25 kilobases (e.g., 4-20, 5-15, or 6-10 kilobases), and the size of the second region that replaces a portion of the targeted locus can be, for example, approximately 0.5-5 kilobases (e.g., 1-4 or 3-4 kilobases). A specific example of such a construct is described below, in the experimental examples.

The targeting constructs can be included within any appropriate vectors, such as plasmid or viral vectors (e.g., adenovirus or adeno-associated virus vectors), which can be introduced into cells using standard methods including, for example, viral transduction, electroporation, or microinjection. One example employs an adeno-associated viral vector (AAV) (e.g., rAAV2, which can be made by standard methods using a pAV2 plasmid (ATCC 37216), rAAV1, and rAAV5).

The use of AAV to deliver the targeting construct offers many benefits. First, AAV1 (and other AAV serotypes) infects pig fetal fibroblasts with 95-100% efficiency. Second, AAV infection of pig fetal fibroblasts results in little or no cell toxicity. Third, AAV infection results in the delivery of a single-stranded gene targeting construct directly to the nucleus. Single-stranded gene targeting vectors are thought to yield more efficient gene targeting and result in a more favorable homologous recombination to non-homologous recombination ratio (Hendrie and Russell, Molecular Therapy 12(1):9-17, 2005).

The methods of the invention, employing AAV vectors, resulted in high levels of gene targeting efficiency in these somatic cells, as compared to prior methods. Central to the methods of the invention is the fact that the entire procedure was performed in a time-sensitive manner, because excessive cell culture time (more than 30 days) negatively impacts nuclear transfer efficiency (Lai et al., Cloning and Stem Cells 5(4):233-241, 2003). In one example, following fibroblast harvest from day 35 fetuses, the fetal fibroblast cells were frozen within 48 hours. The use of an AAV vector to deliver the gene targeting construct allowed targeting to begin 24 hours after thawing cells and required no cell detachment and re-attachment, which is required in other methods. Multiple cell detachment and re-attachment events (trypsinization) are thought to decrease the ability of a cell to serve as a nuclear donor in nuclear transfer. Further, G418 selection in 48 96-well plates prevents the need for the more conventional, time-consuming isolation of resistant clones with cloning rings. The screen for gene-targeted clones was designed such that all positive clones could be identified and frozen within a 3-5 day period. All clones were frozen by day 18, therefore the cells have been in culture approximately 20 days since being harvested from the fetus. This is an important aspect of the invention, because reduction of the time in culture increases the likelihood that cells used as nuclear donors are viable, normal, and euploid.

Accordingly, the invention provides a method of gene-targeting cells, such as pig cells (e.g., pig fetal fibroblasts), in which the number of days in culture (during which targeting and selection takes place) is less than 30 days, e.g., 25-29, 20-24, 19, 18, 17, 16, 15, or fewer days. To facilitate this method, the selection can take place in multi-well plates, as described further below. Further, the cells may be frozen shortly after harvest (e.g., within 24, 48, or 96 hours). After cell thawing (or after harvest, if the cells are not previously frozen), gene targeting with an AAV vector can be carried out within, for example, 12, 24, 36, or 48 hours, without the use of multiple detachment/re-attachment events, and selection can proceed in an expedited manner, such as by use of multi-well plates (e.g., 96-well plates), prior to freezing.

Other types of vectors, or more specifically other types of targeting construct delivery methods, are available, and were used during initial attempts to disrupt the pig CFTR gene. Cell transfection methods, including calcium phosphate, lipofection, electroporation, and nuclear injection can be used to deliver the targeting construct, though the disadvantages of inefficient transfection efficiency, cell toxicity, requirement of a pure (clean) targeting construct DNA sample, and poor ratio of homologous recombination to non-homologous recombination far outweigh the benefit of ease. If the gene is transcriptionally active in the cell being used, then a promoterless selectable marker strategy can be employed, so that antibiotic resistance will only be found in cell that have had a recombination event within a transcribed unit.

Genetically targeted cells are typically identified using a selectable marker, such as neomycin. If a cell already contains a selectable marker, however, a new targeting construct containing a different selectable marker can be used. Alternatively, if the same selectable marker is employed, cells can be selected in the second targeting round by raising the drug concentration (for example, by doubling the drug concentration), as is known in the art. As is noted above, targeting constructs can include selectable markers flanked by sites facilitating excision of the marker sequences. In one example, constructs can include loxP sites to facilitate the efficient deletion of the marker using the cre/lox system. Use of such systems is well known in the art, and a specific example of use of this system is provided below, in the experimental examples.

Upon obtaining cells in which a target gene (e.g., a CFTR gene) has been targeted (one or both alleles, as described above), nuclear transfer can be carried out. Optionally, the genetically modified nuclear donor cells can be frozen prior to nuclear transfer. Recipient cells that can be used in the invention are typically oocytes, fertilized zygotes, or two-cell embryos, all of which may or may not have been enucleated. Typically, the donor and the recipient cells are derived from the same species. However, it is possible to obtain development from embryos reconstructed using donor and recipient cells from different species.

Recipient oocytes can be obtained using methods that are known in the art or can be purchased from commercial sources (e.g., BoMed. Inc., Madison, Wis.). As is known in the art, the donor nucleus or the donor cell itself can be injected into the recipient cell or injected into the perivitelline space, adjacent to the oocyte membrane. The nuclear transfer complex formed in this manner can be activated by standard methods, which may involve electrical fusion/activation or electrical fusion/chemical activation, as is described further below. Further processing of the nuclear transfer complex, including implantation of the complexes into surrogate mothers, is described further below.

The transgenic animals of the invention can be used in the identification and characterization of drug and other treatment methods for the disease or condition associated with mutation of the gene targeted according to the invention. In these methods, for example, a candidate therapeutic agent can be administered to an animal and the impact of the agent on a feature of the disease exhibited by the animal can be monitored. Optionally, the methods can also involve exposure of the animals to environmental or other conditions known to contribute to or exacerbate the disease or condition. For example, in the case of CF animal models having impaired respiratory function, the effect of the drug on such function can be assessed by measurement of standard respiratory parameters. In another example, in the case of animals exhibiting impaired digestion, due to blockage of pancreatic and/or liver ducts, the effect of a treatment on digestion can be determined.

With the porcine model of the invention, it is possible to test hypotheses that lead to new treatments and to evaluate potential therapies for CF lung disease. The porcine model also makes it possible to assess electrolyte transport by porcine airway epithelia in vitro and in vivo, the volume of airway surface liquid in vitro and in vivo, the ion composition of airway surface liquid in vitro and in vivo, the airway surface liquid pH in the airway, and electrolyte transport in the small airways. It is also possible to measure respiratory mucociliary transport in vitro and in vivo. For assessing inflammation, several tests and assays can be carried out, including (but not limited to) assays of key markers of inflammation in amniotic fluid, fetal lung liquid, and bronchoalveolar lavage by using lung tissue histochemistry, large-scale gene expression profiling of pulmonary tissues, cytokine and cell assays, and proteomics. It is also possible to raise CF and non-CF piglets in isolators under completely germ free conditions and to test for the development of pulmonary inflammation, and then selectively expose the piglets to inflammatory stimuli including bacteria and viruses. In addition, investigators can test how loss of CFTR function in airway epithelia results in altered NFKB signaling, the function of secreted epithelial antimicrobials/host defense proteins, and the consequences of loss of CFTR function in macrophages or neutrophils. The availability of the porcine CF model allows tests of the early manifestations of the CF, an important question that remains unanswered. The natural history of pulmonary infections in CF pigs can also be monitored, leading to a determination of whether the airway epithelia of CF pigs can be colonized by CF or porcine pathogens and/or non-pathogenic opportunistic organisms.

Although lung disease is the current main cause of mortality, patients suffer from CF disease in many other organs. Availability of a CF model allows new investigations and tests of therapeutics in the pancreas, intestine, sweat gland, liver, vas deferens, kidney, and other organs affected primarily or secondarily by CF. The screening methods of the invention can be carried out to test the efficacy of new compounds, combinations of new and old compounds, non-pharmaceutical treatments, and combinations of pharmaceutical and non-pharmaceutical treatments.

As described further below, CFTR−/− pigs of the invention have been generated and extensively characterized with respect to genotype of phenotypic characteristics. The CFTR−/− pigs have been found to share phenotypic characteristics with human CF, many of which are not also shared by murine CF models. These differences highlight the importance of the animal models of the invention in the development of therapeutics for human CF. Animal models of the invention thus include large non-human animals, such as pigs, having any one or more of the following clinical, electrophysiological, or pathological characteristics, relative to corresponding wild-type animals:

(i) electrophysiological features similar to CF humans including, e.g., any one or more of (a) hyperpolarized baseline Vt, (b) reduction of Vt by amiloride, and (c) no CFTR or other Cl⁻ channel activity (as measured by, e.g., perfusion of apical surface with Cl⁻-free solution and addition of isoproterenol; perfusion with ATP to activate P2Y2 receptors and $Ca^{2+}$-activated Cl⁻ channels; and perfusion with the CFTR inhibitor GlyH-101);

(ii) meconium ileus, as characterized by, e.g., one or more of (a) obstruction in the small intestine and/or colon (e.g., near the ileocecal junction), (b) the appearance of microcolon distal to the obstruction, (c) intestinal perforation and/or peritonitis, (d) failure to pass feces or gain weight, (e) failure to eat, (f) abdominal distension, (g) bile-stained emesis, (h) proximal dilation of the small intestine, (i) meconium distension of the intestine, (j) degenerated and atrophied villi adjacent to the meconium, (k) reduced luminal diameter distal to the meconium, (l) mucinous hyperplasia (including mucoid luminal plugs) distal to the meconium, and (o) distal intestinal obstruction syndrome (DIOS);

(iii) exocrine pancreatic insufficiency or abnormalities, as characterized by, e.g., one or more of (a) decreased size, (b) degenerative lobules with, e.g., increased loose adipose and myxomatous tissue, and scattered to moderate cellular inflammation, (c) diminished eosinophilic zymogen granules in residual acini, (d) variable dilation and obstruction of centroacinar spaces, ductules, and ducts with eosinophilic material plus infrequent neutrophils and macrophages mixed with cellular debris, (e) foci of mucinous metaplasia in ducts and ductules, and (f) increased redness;

(iv) hepatic abnormalities consistent with focal biliary cirrhosis, as characterized by, e.g., any one or more of (a) mild to moderate hepatic lesions, (b) chronic cellular inflammation, (c) ductular hyperplasia, and (d) mild fibrosis;

(v) gall bladder and/or bile duct abnormalities, as characterized by, e.g., any one or more of (a) gallstones, (b) reduced size, (c) congealed bile and mucus, and (d) epithelia with diffuse mucinous changes with folds extending into the lumen; and (vi) lack of abnormalities in vas deferens and lungs at birth. It is expected that CFTR−/− pigs will develop abnormalities in these features as they age, consistent with what is found in humans, in which case a comparison of these features in older animals can also be made.

The invention has been described above in reference to mutation of the CFTR gene to generate non-human animal models of cystic fibrosis. As is stated above, the invention can also be used in the generation of transgenic, non-human animal models of other diseases and conditions associated with gene mutations. There are innumerable examples of such diseases and conditions known in the art, which can be included in this invention. Some specific examples are listed in Table 1.

TABLE 1

| Disease | Gene | Reference |
| --- | --- | --- |
| Hypercholesterolemia and atherosclerosis | LDLR and APOE | Lusis et al., Annu. Rev. Genomics Hum. Genet. 5: 189-218, 2004 |
| Cancer | p53, BRCA1 and 2 | Levine-A J, Cell, 88: 323-331, 1997 Gudmundsdottir and Ashworth, Oncogene. 25(43): 5864-5874, 2006 |
| Huntington's disease | huntingtin | Walker, Lancet 369(9557): 218-28, 2007 |
| Duchenne muscular dystrophy | dystrophin | Deconinck and Dan. Pediatr Neurol. (1): 1-7, 2007 |
| Polycystic kidney disease | PKD1 and 2 | Gattone V., Current Opinion in Pharmacology 5: 535-542, 2005 |
| Sickle-cell disease | alpha/beta-globin | Steinberg M H, Trends Pharmacol. Sci. 27(4): 204-10, 2006 |
| Hemophilia A | Factor VIII | Bolton-Maggs and Pasi, Lancet 24; 361(9371): 1801-9, 2003 |
| Ataxia-telangiectasia | ATM | Concannon and Gatti, Hum. Mutat. 10(2): 100-7, 1997 |
| Retinoblastoma | RB1 | Lohmann, Hum. Mutat. 14(4): 283-8, 1999 |

Possible mutations to these disease genes include knock-outs (by, e.g., insertion of a selection cassette), knock-ins (e.g., by point mutations that correspond to human disease mutations), and, in the case of Huntington's disease (and any other trinucleotide repeat expansion disorder family members), an expansion of the trinucleotide repeat to pathogenic sizes.

The following Examples are meant to illustrate the invention and are not meant to limit the scope of the invention in any way.

EXPERIMENTAL EXAMPLES

Pigs with two different alterations in their CFTR gene, a null allele and the ΔF508 mutation will provide useful animal models for the study of CF. A null allele would lack any CFTR function and should therefore provide a valuable model for assessing the porcine CF phenotype, for comparing the consequences of other CF-associated mutations, for exploring pathogenesis, and for evaluating many therapeutic strategies. The ΔF508 mutation deletes Phe508 and is the most common CF-associated mutation, accounting for ~70% of CF alleles (Zielenski et al., Annu. Rev. Genet. 29:777-807, 1995). In humans, this mutation disrupts processing of the protein, so that nearly all CFTR-ΔF508 is retained in the endoplasmic reticulum (ER) and degraded, preventing maturation to the plasma membrane. In addition, this deletion reduces the activity of single CFTR channels and shortens their lifetime on the cell surface (Dalemans et al., Nature 354:526-528, 1991; Teem et al., Receptors Channels 4:63-72, 1996; Skach, Kidney Int. 57:825-831, 2000). Earlier work showed that reducing the incubation temperature and other interventions allowed some of the mutant protein to escape the ER and traffic to the cell surface, where it retained significant activity (Denning et al., Nature 358:761-764, 1992). These findings and the prevalence of the ΔF508 mutation have driven efforts to correct the CFTR-ΔF508 defects (Lukacs et al., N. Engl. J. Med. 349:1401-1404, 2003; Verkman et al., Curr. Pharm. Des. 12:2235-2247, 2006). We have found that porcine CFTR-ΔF508 showed at least partial processing in vitro (Ostedgaard et al., Proc. Natl. Acad. Sci. U.S.A. 104:15370-15375, 2007; also see-below). A pig with the ΔF508 mutation could be of value for understanding the mechanisms responsible for the CFTR-ΔF508 biosynthetic defects in vivo and for developing pharmacological agents to correct the CFTR-ΔF508 biosynthetic defects. To begin developing these porcine models of CF, we combined gene targeting and SCNT.

The following experimental examples describe the generation of cystic fibrosis pig models (CFTR-null and CFTR-ΔF508 alleles), an interspecies analysis of the ΔF508 mutation, and approaches to making pigs expressing human CFTR sequences (e.g., human ΔF508 CFTR).

I. Cystic Fibrosis Pig—Generation of CFTR−/+Heterozygote Results

Fetal Pig Fibroblasts Express Little CFTR

We worked with fetal fibroblasts from domestic pigs (*Sus scrofa*) since they have been used successfully for transgenic SCNT (Park et al., Animal Biotechnology 12(2):173-181, 2001). Because a promoter-trap strategy was previously used in porcine fibroblasts (Lai et al., Science 295:1089-1092, 2002), we asked if CFTR is expressed in fetal fibroblasts. We used quantitative RT-PCR and compared the results to transcript levels in nasal and rectal epithelia, which are known to express CFTR at low levels (Trapnell et al., Proc. Natl. Acad. Sci. U.S.A. 88:6565-6569, 1991). FIG. 1 shows that the primary fibroblasts produced very little CFTR mRNA. This result prevented the use of a promoter-trap strategy as was done for the only other gene targeted in pigs (Lai et al., Science 295:1089-1092, 2002; Dai et al., Nat. Biotechnol. 20:251-255, 2002).

Developing Vectors to Target the Pig CFTR Gene

Figure 2:
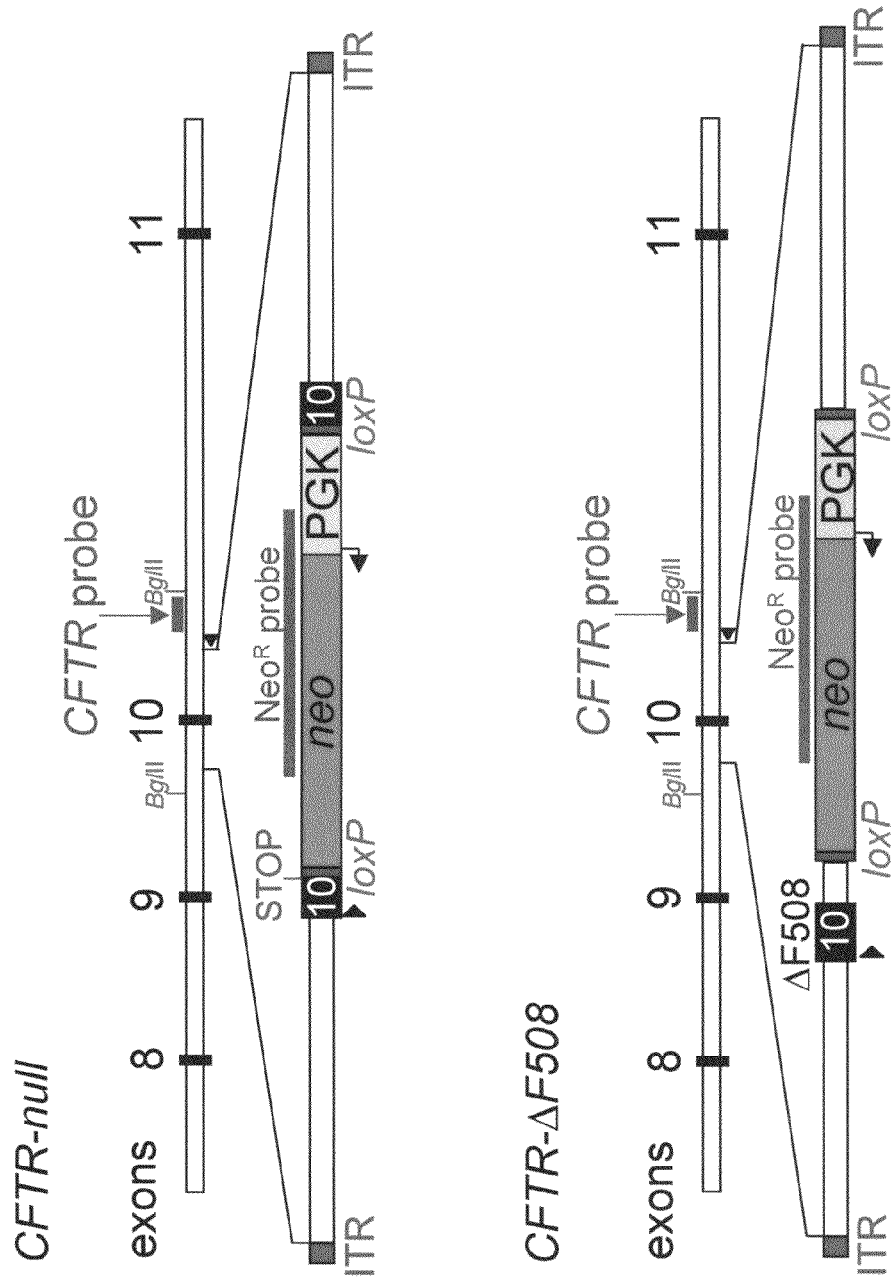
FIG. 2 is a schematic representation of targeting constructs for homologous recombination for CFTR-null and CFTR-ΔF508. Exons 8-11 of pig CFTR are depicted in black boxes. $Neo^R$ contains a neomycin resistance cDNA driven by the PGK promoter and flanked by loxP sites. The engineered stop codon is indicated in the CFTR-null targeting vector. The positions of probes for $Neo^R$ and CFTR Southern blots are indicated. PCR screen primers are depicted as arrowheads.

We designed a "null" targeting construct to disrupt CFTR exon 10 with a neomycin resistance cassette ($Neo^R$) (FIG. 2). Because CFTR can exhibit some alternative splicing, we chose to disrupt exon 10, which encodes a portion of nucleotide binding domain 1; this exon is required for CFTR function. We also included an engineered stop codon at position 508. Therefore, F508X would be expected to trigger nonsense-mediated mRNA decay as well as prematurely interrupt any translation of CFTR. The ΔF508 targeting vector was designed to delete residue Phe508 (FIG. 2). We also inserted a $Neo^R$ in the intron downstream of exon 10 as a positive selection marker. In this vector, $Neo^R$ was flanked by loxP sites so that it could be removed at a later time if it was found to markedly reduce the level of the CFTR-ΔF508 mRNA, a situation encountered in some attempts to make a CFTR-ΔF508 mouse (Colledge et al., Nat. Genet. 10:445-452, 1995; Zeiher et al., J. Clin. Invest. 96:2051-5064, 1995).

We initially used nuclear microinjection and then electroporation to deliver the null targeting vector to fetal fibroblasts. However, we recovered no clones with homologous recombination. We then investigated AAV-mediated gene targeting, which has been used to deliver targeting vectors to cell lines and primary cells (Inoue et al., J. Virol. 73:7376-7380, 1999; Hirata et al., Nat. Biotechnol. 20:735-738, 2002; Porteus et al., Mol. Cell. Biol. 23:3558-3565, 2003; Russell et al., Nat. Genet. 18:325-330, 1998). Using an AAV vector has the advantage that it delivers single-stranded DNA to the nucleus, the amount of DNA per cell is small, and it can infect many cell types (Hendrie et al., Mol. Ther. 12:9-17, 2005). To first determine which AAV serotypes can infect pig fetal fibroblasts, we infected them with eGFP-expressing AAV1, 2, and 5 (each with AAV2 ITRs). Each AAV infected the cells with at least 50-80% efficiency, however, AAV 1 appeared to infect nearly 100% of cells. Because of rAAV genome size constraints, the total length of the targeting vectors was limited to ~4.5 kb. $Neo^R$ was centrally located in both vectors (FIG. 2).

AAV Vectors Introduced the CFTR-Null and CFTR-ΔF508 Alleles

We obtained fetal fibroblasts from males so that all of our clones would be male, which would allow us to more rapidly expand the number of animals. Primary cultures of pig fetal fibroblasts were infected with AAV1 carrying the null targeting vector. After 24 hours, cells were transferred to a series of 96-well plates. Approximately two weeks later, cells in each well of the 96-well plates were "replicated" by splitting among three plates: 96-well culture plates for cell expansion, 96-well culture plates for potential cryopreservation, and 96-well PCR plates for cell lysis.

Figure 3:
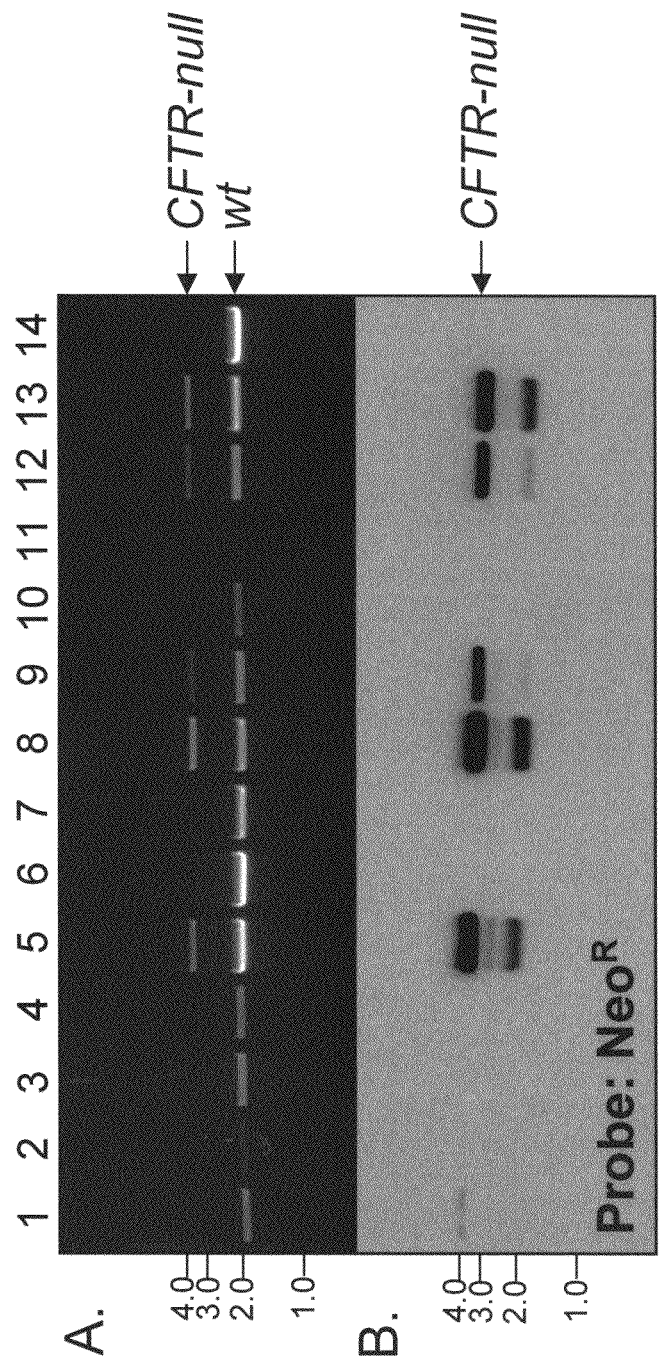
FIG. 3 shows screening results from CFTR-null targeted pig fetal fibroblasts. A) Example of PCR results. Primers amplified a 2.0 kb product from the wild-type allele and 3.7 kb product from the CFTR-null allele. Lanes 5, 8, 9, 12, and 13 are examples of PCR-positive clones. B) Southern blot of the PCR gel using a $Neo^R$-specific biotin-labeled oligonucleotide. This assay confirms that the 3.7 kb product contains the $Neo^R$ sequence. The weaker hybridization signal at 2.0 kb appears to be an artifact, with some of the targeted band co-migrating with the wild-type product. Note the differences in intensity of the two bands in panel A relative to panel B.
Figure 4:
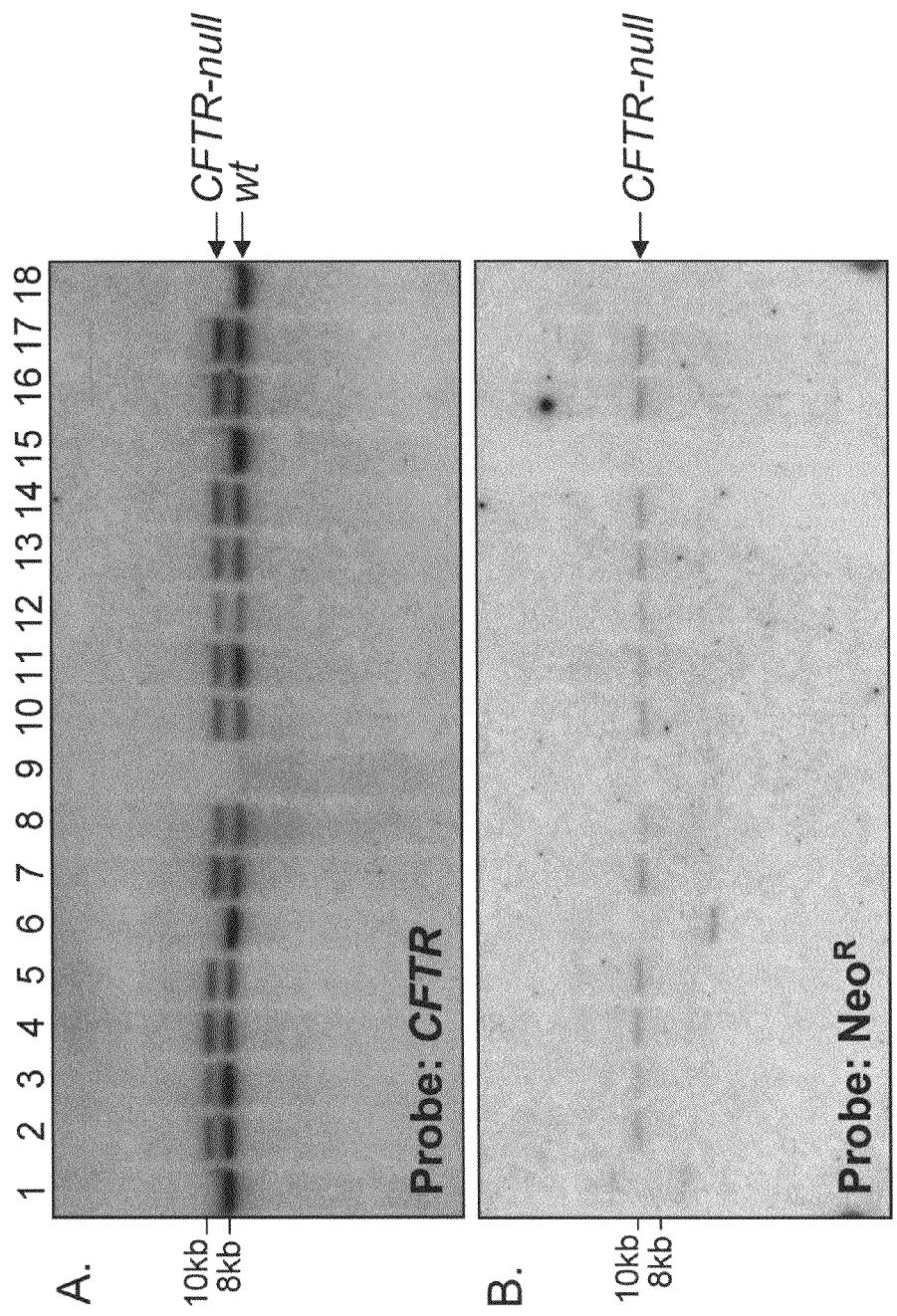
FIG. 4 is a genomic Southern blot of DNA from CFTR-null targeted pig fetal fibroblasts. A) BglII-digested genomic DNA was hybridized with a probe that detects pig CFTR downstream of the targeting vector boundary. CFTR-null-targeted allele yields a ~9.7 kb band and wild-type is ~7.9 kb. These blots also allowed us to identify wells containing monoclonal colonies and those containing more than one type of $G418^R$ colony. For example, wells 3 and 11 appeared to have more intense signals in the wild-type band than the targeted band, indicating that those wells likely contained one targeted clone and one or more random integration events. B) The same digested DNAs were hybridized with a $Neo^R$-specific probe. The CFTR-null-targeted band is at ~9.7 kb. Note that the band in lane 6 likely represents a random integration event, and lane 1 may have two random integration events. Wells 4, 5, 7, 8, 10, 12-14, 16, and 17 are examples of cells that may be ideal nuclear donors for generating a heterozygote animal

We screened cell lysates by PCR to identify wells containing gene-targeted clones (FIG. 3A) and then hybridized with a $Neo^R$-specific probe to test for inclusion of this marker (FIG. 3B). We then froze positive clones; by that time, cells had been in culture 15-17 days. We also passaged positive clones from the "cell expansion" plates to generate DNA for genotype determination. Southern blots with CFTR- and $Neo^R$ specific probes identified clones with a targeted CFTR allele that were free of random integration (FIG. 4). On average, 75% of PCR-positive clones were also positive by Southern blot and were clonal.

Figure 5:
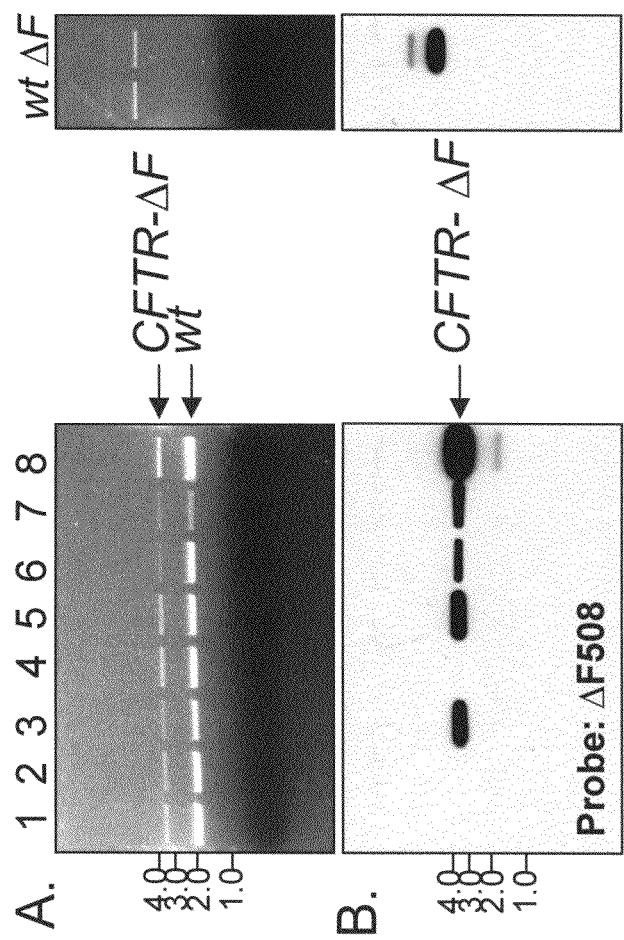
FIG. 5 shows screening results from CFTR-ΔF508 targeted pig fetal fibroblasts. A) Example of PCR results. Primers amplified a 2.0 kb product from the wild-type allele and a 3.7 kb product from the CFTR-ΔF508 allele. B) Southern blot of the PCR gel using a ΔF508 allele-specific biotin-labeled oligonucleotide. This assay confirms some of the 3.7 kb products contained the ΔF508 mutation. Note that lanes 1, 2, and 4 contain clones that underwent homologous recombination but failed to carry the ΔF508 mutation. On the right, wells contained either wild-type CFTR or CFTR-ΔF508 plasmid DNA. This control is included to ensure that the assay Southern blot is specific to ΔF508.
Figure 6:
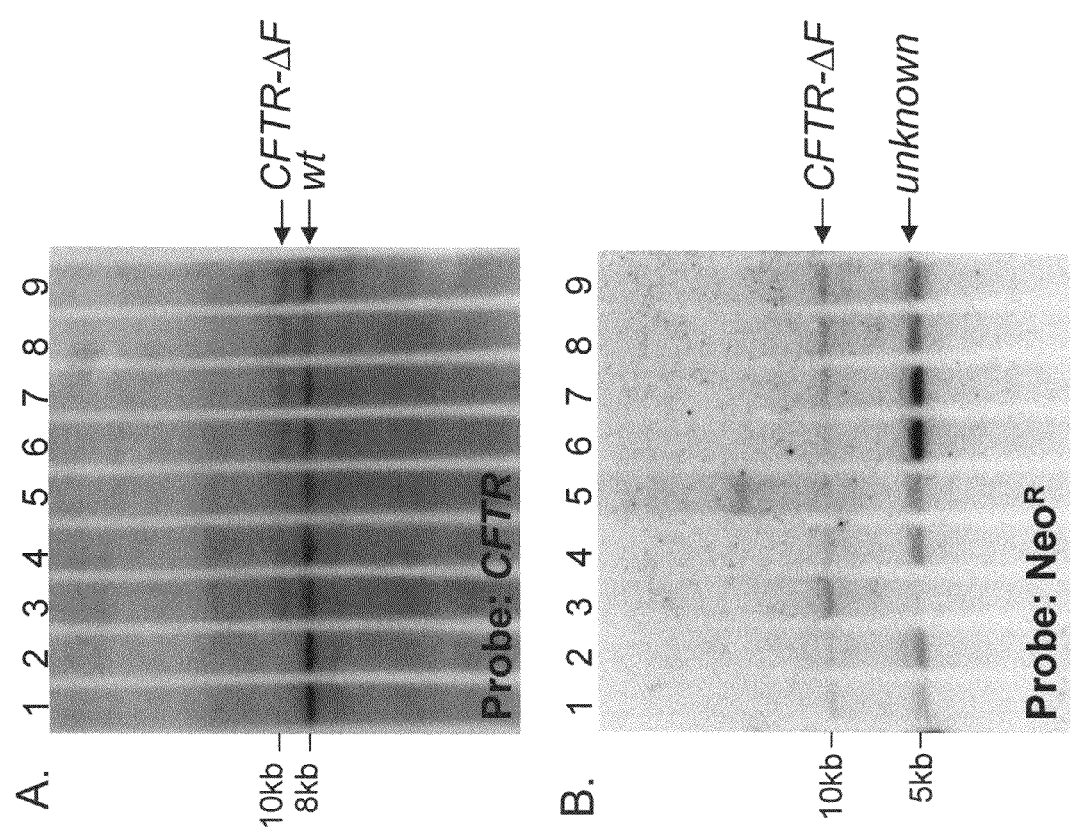
FIG. 6 is a Southern blot of amplified genomic DNA from CFTR-ΔF508 targeted pig fetal fibroblasts. In contrast to our experience with the CFTR-null targeting, the CFTR-ΔF508 targeted cells failed to proliferate after transfer to larger dishes. As a result, we were unable to obtain sufficient quantities of genomic DNA for a genomic Southern blot. Therefore, we used the relatively small amount of DNA for whole genome amplification. A) BglII-digested amplified genomic DNA was hybridized with a probe that detects pig CFTR downstream of the targeting vector boundary. The CFTR-ΔF508-targeted allele yields a ~9.7 kb band and the wild-type is ~7.9 kb. B) Digested DNAs from similar clones were hybridized with a $Neo^R$-specific probe. The CFTR-ΔF508-targeted band is at ~9.7 kb. Note that all lanes in this Southern blot contain an intense band at ~5 kb. This band was also present in non-infected fibroblast control DNA wells. This probe is possibly hybridizing to the endogenous PGK promoter sequence, because the probe includes some PGK promoter sequence. Consistent with this, the $Neo^R$-probed blot in FIG. 4A also contains a faint band at 5 kb in all samples if markedly overexposed.

We used identical procedures to introduce the CFTR-ΔF508 construct and screen for homologous recombinants. We identified numerous PCR-positive clones (FIG. 5A), that were confirmed by Southern blotting with a ΔF508 allele-specific probe (FIG. 5B). Eighteen of 25 (72%) PCR-positive clones contained the F508 deletion. The other 28% failed to contain ΔF508, suggesting that gene targeting had occurred, but crossing over was downstream of F508. Subsequent Southern blots revealed CFTR-ΔF508 targeted clones (FIGS. 6A and 6B).

Variability in Homologous Recombination Depended on the Donor

Over the course of these studies, we targeted the CFTR gene in fibroblasts derived from several fetuses. The fetuses were all siblings harvested from the same uterus at the same time. Yet, surprisingly, we saw a striking fetus-to-fetus variability in targeting frequency (Table 2, below). Even when fibroblasts from different fetuses were infected and screened at the same time, with the same reagents, and by the same people, pronounced differences occurred; an example is fetus 5 vs. fetus 7 in Table 2. These results suggest the difference was not due to experimental process.

TABLE 2

| Donor | G418-resistant (%) | Targeted/G418-resistant (%) |
|---|---|---|
| 9 | 0.13 | 0.03 |
| 5 | 0.09 | 10.93 |
| 7 | 0.09 | 0.07 |
| 2 | 0.17 | 7.29 |
| 3 | 0.18 | 7.22 |
| 4 | 0.15 | 0.027 |

CFTR targeting data from donor cells derived from multiple fetuses. "Donor" refers to the number of the donor for the fibroblasts. The percentage of G418-resistant cells was determined by dividing the number of G418-resistant clones by the number of AAV-infected cells * 100. Targeted clones are those that were PCR-positive for homologous recombination.

SCNT Produced Gene-Targeted Piglets

Figure 7:
FIG. 7 is a photograph of the first CFTR+/− piglet taken at one day of age.
Figure 8:
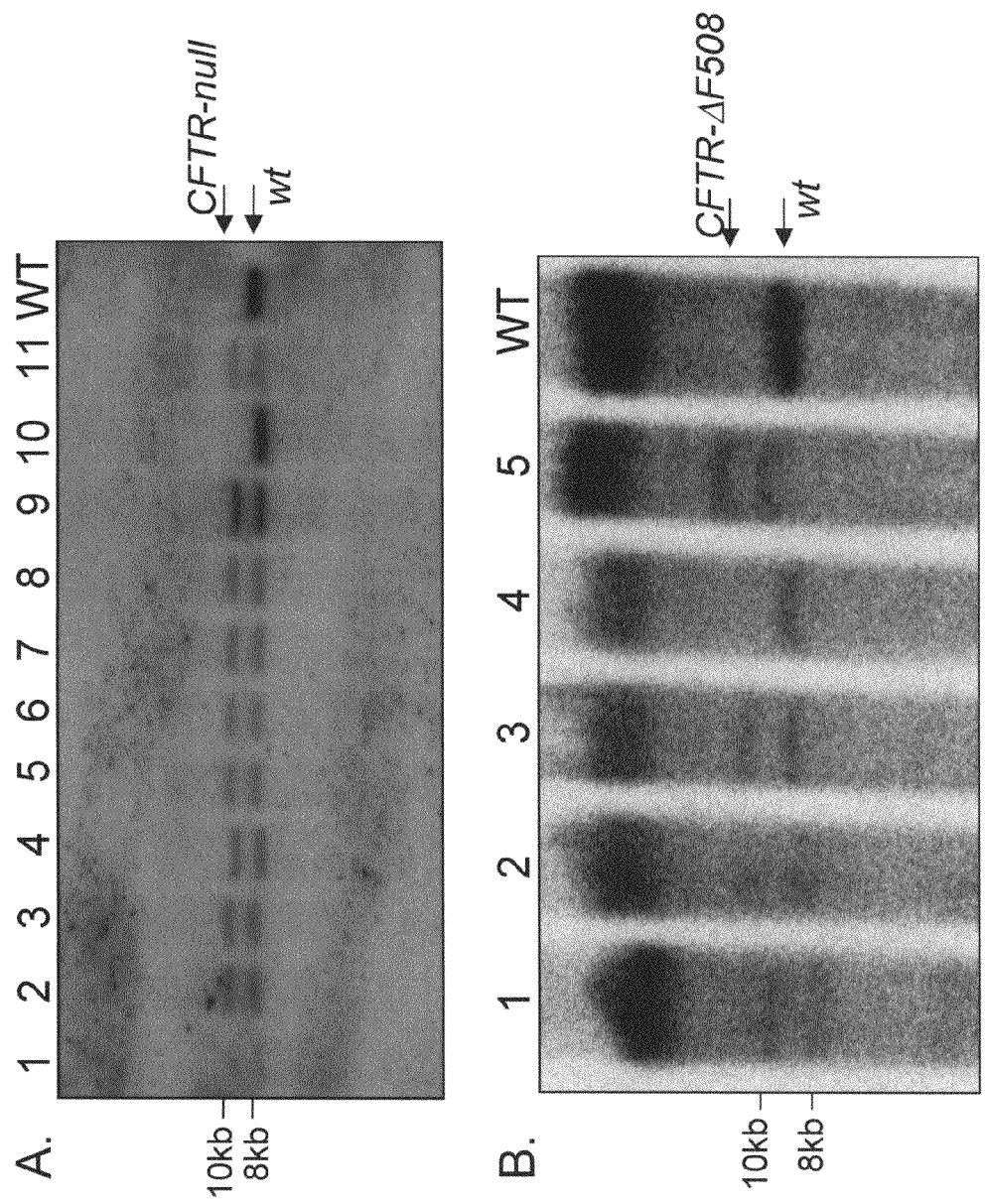
FIG. 8 is a Southern blot of genomic DNA from CFTR-targeted pigs. BglII-digested genomic DNA was hybridized with a probe that detects pig CFTR downstream of the targeting vector boundary, shown in FIG. 2. CFTR-null and CFTR-ΔF508-targeted alleles produced a ~9.7 kb band, and wild-type is ~7.9 kb. A) CFTR-null. Lanes 1-11 contain DNA from individual cloned pigs. Note that pig 10 was wild-type. WT well contains DNA from a wild-type control. B) CFTR-ΔF508. Lanes 1-5 contain DNA from individual cloned pigs. Note that pig 4 was wild-type. WT well contains DNA from a wild-type control.

To produce heterozygote pigs, we used the CFTR-null targeted fetal fibroblasts as nuclear donors for transfer to enucleated oocytes. Then to each of eight surrogate females, we transferred between 94 and 144 SCNT embryos. At 117-118 days of gestation (full term), we delivered piglets by Cesarean section. Five surrogates produced ten males; three surrogates did not produce offspring. FIG. 7 shows the first CFTR+/− piglet. Southern blots revealed that nine of the ten offspring were CFTR-null heterozygotes, and one was wild-type (FIG. 8). The CFTR+/− males reached sexual maturity, and they sired numerous litters of heterozygote offspring, both males and females.

In addition, each of four surrogates received 103-185 CFTR-ΔF508 SCNT embryos. Five males were recovered from three surrogates on days 116-117. Southern blots revealed that four were CFTR-ΔF508 heterozygotes and one was a wild-type. The CFTR-ΔF508 males have not yet reached sexual maturity. All of the CFTR+/− and CFTR+/ΔF508 were phenotypically normal.

The ΔF508 Allele, but not the Null Allele, Generated mRNA

Figure 9:
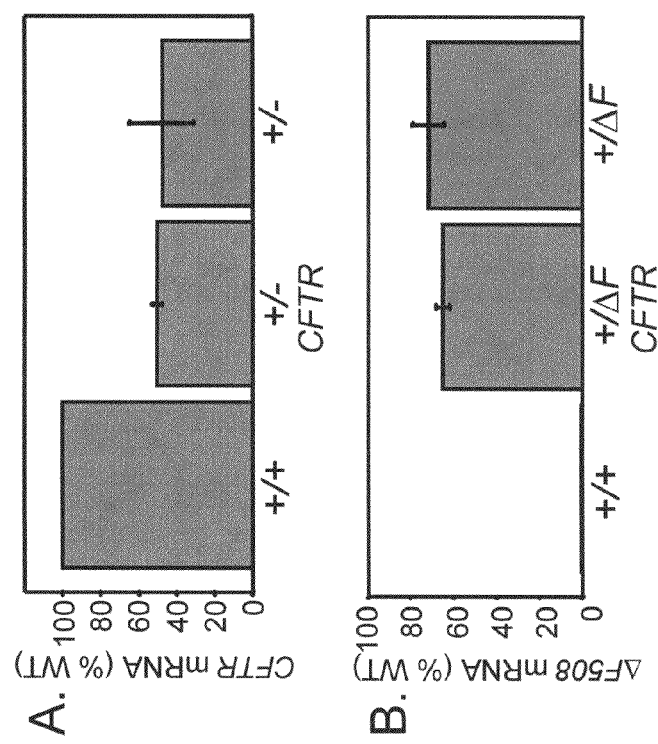
FIG. 9 shows CFTR mRNA expression in CFTR+/− and CFTR+/ΔF508 pigs. A) Quantitative RT-PCR was used to measure wild-type CFTR mRNA levels in rectal epithelial samples from CFTR+/− and wild-type pigs. B) Quantitative RT-PCR was used to measure ΔF508-CFTR mRNA relative to wild-type mRNA levels in CFTR+/ΔF508 and wild-type pigs. Error bars represent S.D.

We asked whether the targeted alleles were transcriptionally active in an epithelium where CFTR is normally expressed. We biopsied rectal epithelia and measured CFTR mRNA using quantitative RT-PCR. In CFTR+/− animals, mRNA was present at ~50% of wild-type levels (FIG. 9A). We cannot be certain that the remaining mRNA arose from the non-targeted allele, however the result is consistent with disruption of one CFTR allele and nonsense-mediated mRNA decay.

To assess the influence of the Neo$^R$ cassette that resides in the intron downstream of exon 10, we used probes specific for wild-type CFTR and CFTR-ΔF508. CFTR-ΔF508 mRNA was present at 65-70% of wild-type levels (FIG. 9B). This expression level suggests that the retained Neo$^R$ cassette has only minimal effects on transcription. Moreover, this amount of transcript is likely sufficient to produce relatively normal amounts of CFTR-ΔF508 protein.

Materials of Methods

Fetal Fibroblasts

Fetal fibroblasts were isolated from day 35 fetuses as previously described (Lai et al., Cloning Stem Cells 5:233-241, 2003). Cells were grown at 39° C. in F10 media (Invitrogen) containing 20% FCS and 30 μg/ml gentamicin. Fetus gender was determined by PCR amplification of the Y-chromosome-specific Sry gene (Pomp et al., J. Anim. Sci. 73:1408-1415, 1995).

Targeting Vector Construction

Genomic clone: Genomic DNA was isolated (Puregene, Gentra) from pig fetal fibroblasts. A 5683 bp PCR product including CFTR exon 10 and flanking intronic sequence was amplified from pig fetal fibroblast genomic DNA using primers GC1F and GC8R (for primer sequences see Table 3, below) and a high fidelity polymerase (PfuUltra, Stratagene). Primers were designed based on the domestic pig genomic sequence from the NIH Intramural Sequencing Center (NISC) Comparative Vertebrate Sequencing Project (Genbank: AC092478 and AC092497). This PCR product was subcloned into pCR-Blunt II-TOPO (Invitrogen), verified by sequencing (using primers GC1F-GC8R), and served as the template for PCR amplification of 5' and 3' targeting arms. This plasmid is referred to as pG16.

CFTR-KO construction: Using PCR, the 5' and 3' homologous recombination arms were amplified from pG16 and sequentially subcloned upstream and downstream of the Neo$^R$ cassette in pPGK-Neo-I (a generous gift from Tim Ley, Washington University; Genbank Accession Number AF335419) such that the Neo$^R$ cassette is in the opposite orientation to the CFTR sequence. Primers: 5' arm: G16-Neo5'F and G16-Neo5'R; 3' arm: G16-Neo3'F and G16-Neo3'$^R$. The Neo$^R$ cassette consists of a Neo$^R$ cDNA driven by the PGK promoter and is flanked by loxP sites. In the resulting construct, the Neo$^R$ cassette disrupts CFTR exon 10 immediately after an in-frame stop codon that was introduced to follow isoleucine 507. Thymidine 1531 is effectively deleted, becoming the first nucleotide of the stop codon. This targeting construct is referred to as pG16-Neo.

CFTR-ΔF508 construction: The CFTR-ΔF508 targeting vector was constructed in a similar way using the following primers: 5' arm: dF-Neo 5'F-XhoI and dF-Neo 5'R-EcoRV; 3' arm: dF-Neo 3'F-BamHI and dF-Neo 3'R-HindIII. The nucleotides encoding F508 were subsequently deleted from exon 10 using PCR mutagenesis. This targeting construct is referred to as pdF-Neo.

TABLE 3

| Primers Name | Sequence (5'-3') | |
|---|---|---|
| GC1F | TTTCTCTTCTGCCTATTTCCC | (SEQ ID NO: 7) |
| GC1R | AGAAAACACTGAAGGATGCCT | (SEQ ID NO: 8) |
| GC2F | GTTTCAAATAGTTACTCAGTTTGA | (SEQ ID NO: 9) |
| GC2R | CCTCCAACTGACACTAATCTTCTCA | (SEQ ID NO: 10) |
| GC3F | GTAGAGCTGTCAGAGAAGTAA | (SEQ ID NO: 11) |
| GC3R | AAGCCACAGAAGCATATGCAT | (SEQ ID NO: 12) |
| GC4F | AATCACTCTCAGGATGCACAT | (SEQ ID NO: 13) |
| GC5F | ATACTCAGAACAGGAAGTGCT | (SEQ ID NO: 14) |
| GC5R | ATAGCATAAGCTTCACTGTGC | (SEQ ID NO: 15) |
| GC6F | TGTCAGTAGAGAATTAGAGATTA | (SEQ ID NO: 16) |
| GC6R | GCACTACTCACCTACATCCA | (SEQ ID NO: 17) |
| GC7F | ACCTGGAAGTTGGAACACTCA | (SEQ ID NO: 18) |

TABLE 3-continued

| Primers Name | Sequence (5'-3') | |
|---|---|---|
| GC7R | GAAGACCCTTTACCTTTCTTCTA | (SEQ ID NO: 19) |
| GC8F | CATCCAGCTGCAAACAACATT | (SEQ ID NO: 20) |
| GC8R | AATTATGCCAAACTCCATCTTAT | (SEQ ID NO: 21) |
| Ex10a5F | AGAATTTCATTCTGCTCTCAGT | (SEQ ID NO: 22) |

Quantitative RT-PCR Primers and Probes

```
Pig CFTR and GAPDH expression in fetal fibro-
blasts, nasal and rectal tissue (FIG. 1)
and CFTR expression in CFTR +/- pigs (FIG. 9A)
CFTR primers and probe
pCFTR-1819F (anneals within exon 18)
AGTGGGCTGTAAACTCCAGTATAGA        (SEQ ID NO: 23)

pCFTR-1819R (anneals withinin exon 19)
CCTTCTGCCGGCATATCAATAAACT        (SEQ ID NO: 24)

pCFTR-1819 probe (spans exon 18/19 junction)
FAM-ATCGCATCAAGCTATCC-NFQ        (SEQ ID NO: 25)

GAPDH primers and probe
pGAPDH-TM-F
AAGCTCATTTCCTCGTACGACAAT         (SEQ ID NO: 26)

pGAPDH-TM-R
GGAGGCCATGTGGACCAT               (SEQ ID NO: 27)

pGAPDH-TM probe
FAM-TCCACCACCCTGTTGCT-NFQ        (SEQ ID NO: 28)

Pig CFTR and /F508-CFTR expression in CFTR +/ΔF508
pigs (FIG. 9B). Primers are the same for both,
probes are allele specific.
CFTR primers and probe
pCFTR-TM-F
TCATGCCGGGCACCATTAAA             (SEQ ID NO: 29)

pCFTR-TM-R
CGCTTTGATGACACTCCTGTATCTA        (SEQ ID NO: 30)

pCFTR-TM probe
FAM-ACACCAAAGATGATGTTTTC-NFQ     (SEQ ID NO: 31)

ΔF508 primers and probe
delF-TM-Forward
TCATGCCGGGCACCATTAAA             (SEQ ID NO: 32)

delF-TM-Reverse
CGCTTTGATGACACTCCTGTATCTA        (SEQ ID NO: 33)

delF-TM-Probe
FAM-GAAACACCAATGATGTTTTC-NFQ     (SEQ ID NO: 34)

PCR Primers and Probes. All DNA sequences are 5'-
3'. FAM: 6-carboxyfluorescein; NFQ: Non
Fluorescent Quencher
```

AAV Production

The targeting vector sequences were amplified from pG16-Neo and pdF-Neo by PCR to include flanking SbfI sites and were subcloned into the rAAV2 proviral plasmid, pAV2 (ATCC 37216). Because of AAV genome size constraints, the total length of the targeting vectors is ~4.5 kb with the NeoR cassettes centrally located (G16-Neo: 5' targeting arm=1510 bp; 3' targeting arm=1274 bp; NeoR cassette=1706 bp. dF-Neo: 5' targeting arm=1475 bp; 3' targeting arm=1296 bp; NeoR cassette=1706 bp). pAV2-G16-Neo was grown in SURE2 cells (Stratagene) and purified via a $CsCl_2$ method (Sambrook, Fritz, and Maniatis, Molecular Cloning: A Laboratory Manual, 2$^{nd}$ edition, Cold Spring Harbor Laboratory Press, Plainview, N.Y., 1989). rAAV1 (with AAV2 ITRs) was prepared as previously described (Yan et al., J. Virol. 76:2043-2053, 2002). Helper-free virus stocks were treated with nuclease and purified by high-performance liquid chromatography. Physical titers of rAAV were determined by slot blot hybridization. These viruses are referred to as AAV-G16-Neo and AAV-dF-Neo.

Infection and Selection $1.5 \times 10^6$ fetal fibroblasts were thawed and plated on a 100 mm collagen-coated culture dish. 24 hours later, cells were infected with AAV-G16-Neo or AAV-dF-Neo (200 µl, $2.5 \times 10^{12}$ particles/ml). 24 hours later, cells were trypsinized and transferred to 48 96-well, collagen-coated plates (BD Biosciences). 48 hours later, G418 (100 µg/ml) was added to the cell media. 10 days later, each well was trypsinized (60 µl trypsin, 0.5% EDTA) and split among 3 different vessels. For cell freezing, ⅓ of the cells were transferred to 96-well collagen-coated culture dishes and returned to the incubator for growth. For cell propagation, ⅓ of the cells were transferred to 96-well collagen-coated culture dishes and returned to the incubator for growth. For PCR screening, ⅓ of the cells were transferred to 96-well PCR plates.

PCR Screen and PCR Southern Blot

Cells in the 96-well PCR plates were spun down and resuspended in lysis buffer (50 mM KCl, 1.5 mM $MgCl_2$, 10 mM Tris-Cl, pH 8.5, 0.5% Nonidet P40, 0.5% Tween, 400 µg/ml Proteinase K) (McCreath et al., Nature 405:1066-1069, 2000). Most wells (~70%) contained only dead cell debris following selection, but all wells were processed to minimize human error. The cells were lysed for 30 min at 65° C., followed by 10 min at 95° C. 1 µl of lysate was used in a 50 µl PCR reaction. PCR conditions: 2 min at 95° C., 30 cycles of 95° C. for 20 sec, 56° C. for 20 sec, and 68° C. for 4 min, then 68° C. for 5 min. Primers Ex10a5F and GC7R are expected to amplify a 2.0 kb product from wild-type alleles and a 3.7 kb product from G16-Neo targeted alleles. PCR products were electrophoresed on 1.0% E-Gel 96 gels (Invitrogen). Positive PCR reactions were also electrophoresed on standard 1.0% agarose gels and transferred to a nylon membrane. The membranes were probed with biotin-labeled Neo-specific or ΔF508-allele-specific oligonucleotides and detected by chemiluminescence (North2South, Pierce).

Processing Screen-Positive Cells

Following identification of PCR-positive clones, the corresponding cells from the "freezing" plate were grown to confluence (~10,000 cells). Cells were detached with 60 µl trypsin and 20 µl of detached cells were placed into each of 3 cryovials. Three hundred µl freezing media was added to each cryovial and the vials were transferred to an isopropanol cryofreezing container at −70° C. After 24 hours, the vials were transferred to liquid nitrogen. The corresponding cells from the propagation plate were transferred to 24-well plates, and subsequently to 6-well and 100 mm culture dishes. The sequential transfer to increasingly larger culture dishes was carried out to achieve consistent cell growth and viability.

Southern Blotting

For CFTR-KO targeting, genomic DNA was isolated from 100 mm dishes (Gentra) and 10 µg was digested with BglII overnight. For CFTR-ΔF508 targeting, genomic DNA was isolated from 24-well dishes. Ten ng was used for whole genome amplification (Repli-G, Qiagen) and 25 µg amplified DNA was digested with BglII overnight. Genomic digests were electrophoresed on a 0.7% agarose gel and transferred to a positively charged nylon membrane (Roche) by using an alkaline transfer procedure. Blots were pre-hybridized for 15 min at 65° C. in Rapid-hyb buffer (Amersham). The blot was then hybridized in Rapid-hyb buffer with a $^{32}$P labeled probe specific for a region of CFTR that is outside of the targeting vector boundaries. For Neo-specific probing, blots were either stripped, or, in most cases, the BglII digest and Southern blot procedure was repeated using a $^{32}$P-labeled Neo-specific probe.

Preparation of Donor Cells for SCNT

Frozen aliquots of CFTR-targeted cells were thawed at 37° C. and pre-warmed in F-10 medium (Invitrogen) with 20% fetal calf serum (FCS). The cells were washed twice by centrifugation and cultured (F-10, Invitrogen; 20% FCS, Hyclone; gentamicin, 2.5 ng/ml FGF and G418, Invitrogen) for 1-2 days in 24-well collagen-coated plates (35-4408, Biocoat cellware). Confluent cells were dispersed with 0.05% trypsin/EDTA for 3-5 min at 38.5° C. and 500 µL F-10 with 20% FBS, followed by centrifugation twice at 3000 rpm for 5 min. The supernatant was removed, and the cells were resuspended in micromanipulation medium (25 mM HEPES, TCM199, Gibco; 0.3% BSA).

Oocyte Maturation and SCNT

Oocytes were received from BoMed, Inc (Madison, Wis.) ~24 hours after placing them into maturation medium, and were then transferred to a 4-well dish and cultured for a total maturation of 42-44 hours at 38.5° C. in a humidified atmosphere of 5% $CO_2$ in air. After 42-44 h of in vitro maturation, oocytes were stripped of their cumulus cells by gentle vortexing in 0.5 mg/mL hyaluronidase. After removal of the cumulus cells, oocytes with good morphology and a visible polar body (metaphase II) were selected and kept in micromanipulation medium at 38.5° C. until SCNT.

SCNT was performed essentially as previously described (Lai et al., Science 295:1089-1092, 2002; Lai et al., Nat. Biotechnol. 24:435-436, 2006) in micromanipulation medium supplemented with 7.5 µg/mL cytochalasin B. The metaphase II chromosomes and the polar body were aspirated by inserting a micropipette through the zona pellucida and aspirating the polar body and the adjacent cytoplasm into the pipette. Next a donor cell was aspirated into the same pipette, the pipette was inserted into the previously made hole in the zona pellucida, and the cell deposited under the zona pellucida. The nuclear transfer complex was fused in a medium with a low $Ca^{2+}$ concentration (0.3 M mannitol, 0.1 mM $CaCl_2.2H_2O$, 0.1 mM $MgCl_2.6H2O$ and 0.5 mM HEPES), activated with 200 µM thimerosal for 10 min in the dark, and then rinsed and treated with 8 mM dithiothreitol (DTT) for 30 min. Finally the oocytes were rinsed to remove any traces of DTT (Lai et al., Nat. Biotechnol. 24:435-436, 2006). Following fusion/activation, oocytes were washed three times with PZM3 as previously described for 30 min (Im et al., Theriogenology 61:1125-1135, 2004). Those that had fused were cultured for 15-21 hours until surgical embryo transfer to a surrogate.

Surrogate Preparation and Embryo Transfer

The embryonic cleavage rate was examined before transferring the reconstructed embryos into recipients. The recipients were synchronized by administering 18-20 mg Regumate and hCG as previously described (Lai et al., Cloning Stem Cells 5:233-241, 2003). Twelve surrogates on the first day of estrus (designated day 0) or the first day after standing estrus were used. Embryo transfer was performed surgically as previously described (Lai et al., Cloning Stem Cells 5:233-241, 2003) and 94 to 185 embryos were inserted into one oviduct through the ovarian fimbria. Surrogates were checked for pregnancy by abdominal ultrasound examination after day 21 and then checked weekly throughout gestation, and were allowed to go to term. A cesarean section was performed to recover the piglets on day 116-118. After delivery the piglets were provided medical care, fed colostrums, and initially raised on a commercial pig milk replacer until mature enough to be placed on standard pig diets.

Rectal Biopsy

Pigs were lightly anesthetized with ketamine (20 mg/kg) and acepromazine (0.2 mg/kg). A 10 cm anoscope was partially inserted in the rectum and rectal tissue was collected using gastrointestinal biopsy forceps (2.2 mm). Tissue samples were immediately placed in RNAlater (Ambion). Recovery from anesthesia was monitored continuously until the pigs returned to normal activity (2-4 hours).

Quantitative RT-PCR

Quantitative RT-PCR using TaqMan chemistry and an ABI 7500 Fast Real-time PCR System was used to measure pig CFTR mRNA. Briefly, total RNA was isolated from fibroblasts or nasal and rectal biopsy tissue (RNeasy, Qiagen). First-strand cDNA was synthesized with random primers (SuperScript III, Invitrogen). Sequence-specific primers and probes for pig CFTR and GAPDH were designed and ordered using Assays-by-design (Applied Biosystems). For measuring total CFTR mRNA primer/probe sets spanning exons 18 and 19 of CFTR and GAPDH were used in separate reactions. For measuring ΔF508 mRNA levels, one primer set and two probes (F508 and ΔF508) were used in separate reactions. Primer and probe sequences are included in Table 2. TaqMan Fast Universal PCR Master Mix was used for all reactions. The reaction volume was 20 µl (10 µl of 2× Master Mix without UNG, 1 µl of 20× target primer and probe, 8 µl of Nuclease-free water, and 1 µl of cDNA sample). The reaction plates were covered with optical film and centrifuged briefly. The thermocycler conditions were as follows: 20 seconds at 95° C., 40 cycles of 95° C. for 3 seconds and 60° C. for 30 seconds. All experiments were run in triplicate. Because the efficiencies of CFTR and GAPDH amplification were not equal, the relative quantification of transcript levels was performed using the standard curve method.

II. Cystic Fibrosis Pig-Generation of CFTR−/− Homozygote

To develop a new CF model, we chose pigs because compared to mice their anatomy, biochemistry, physiology, size, lifespan, and genetics are more similar to those of humans (Ibrahim et al., Xenotransplantation 13:488, 2006; Rogers et al., Am. J. Physiol. Lung Cell Mol. Physiol. 295(2):L240-63, 2008). We used homologous recombination in fibroblasts of outbred domestic pigs to disrupt the CFTR gene and somatic cell nuclear transfer to generate CFTR+/− pigs (see above and Rogers et al., J. Clin. Invest. 118(4):1571, 2008).

Figure 10:
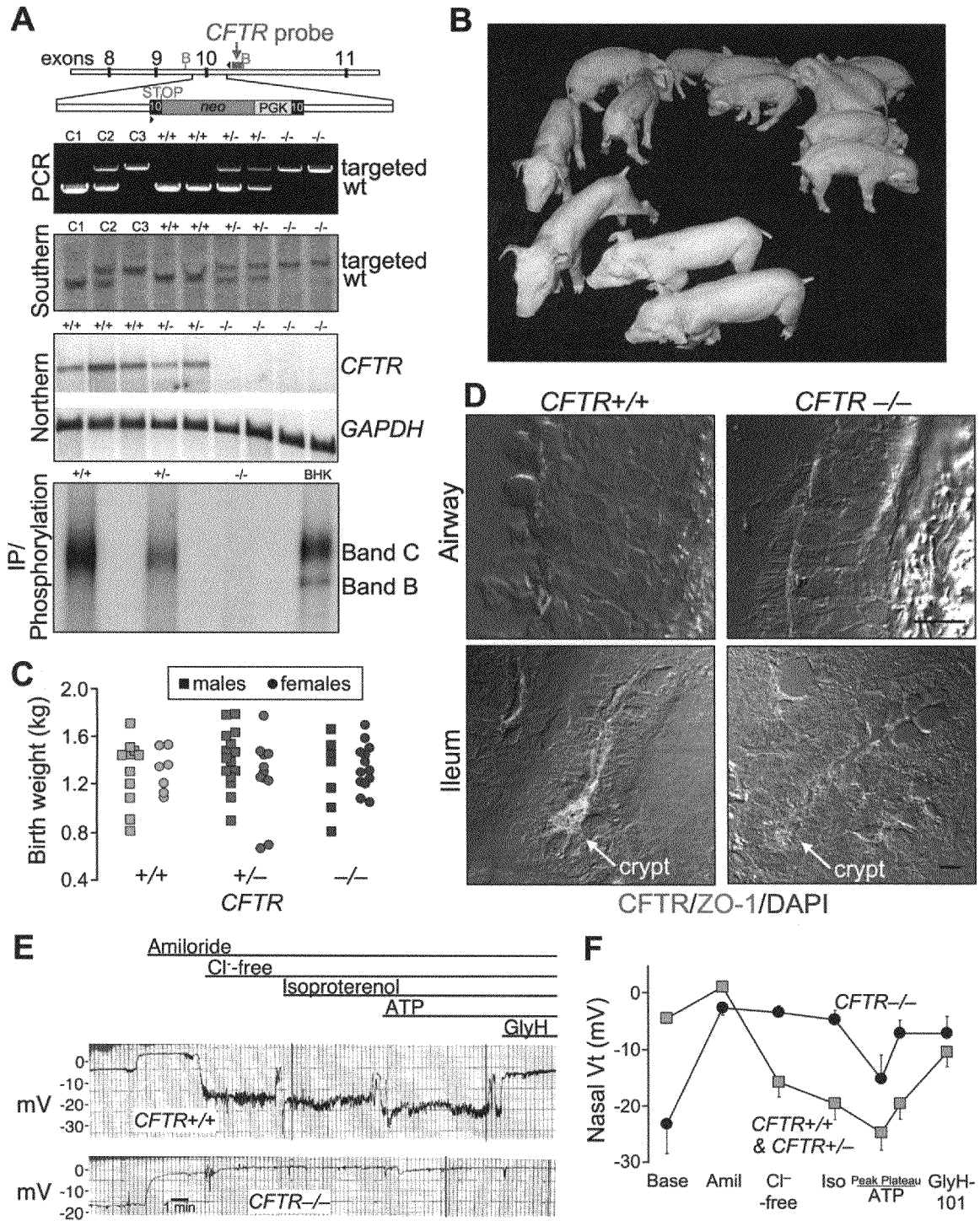
FIG. 10 shows that CFTR−/− piglets appear normal at birth. A) Upper panel depicts insertion into porcine CFTR exon 10 of a PGK promoter (yellow) driving a neomycin resistance cDNA (orange), and an engineered stop codon. Position of probe (green), PCR primers (arrowheads) and BglII sites (B) are indicated. Second and third panels show genotyping by PCR and Southern blot of genomic DNA. Lanes C1, C2, and C3 contain controls of CFTR+/+, +/− and −/− DNA. Fourth panel shows northern blot of ileal CFTR and GAPDH mRNA. Consistent with the northern blot, quantitative RT-PCR of exon 10, the targeted site, detected <0.1% of CFTR transcripts in CFTR−/− ileum relative to CFTR+/+ (n=6 and 4). Fifth panel shows immunoprecipitation and phosphorylation of CFTR plus recombinant CFTR in BHK cells. B) First litter containing piglets of all three genotypes. C) Birth weights. Mean±SD of weights: 1.31±0.24 kg for CFTR+/+, 1.35±0.28 kg CFTR+/−, and 1.31±0.23 kg CFTR−/−. D) Immunocytochemistry of CFTR in airway epithelia (top) and ileum (bottom). Figures are differential interference contrast with staining for ZO-1 (a component of tight junctions, red), CFTR (green), and nuclei (DAPI, blue). See also FIG. 11. Bars, 10 µm. E) Tracings of in vivo nasal voltage (Vt) measured in newborn piglets. After baseline measurements, the following agents/solutions were sequentially added to the epithelial perfusate: amiloride (100 µM), Cl⁻-free solution, isoproterenol (10 µM), ATP (100 µM), and GlyH-101 (100 µM). F) Average nasal Vt measurements as indicated in panel E. Data from 4 CFTR+/+ and 4 CFTR+/− piglets were not statistically different and were combined and compared to data from 5 CFTR−/− piglets. Values of baseline nasal Vt for CFTR−/− piglets differed from the controls, as did the changes in Vt induced by adding amiloride, a Cl⁻-free solution, and GlyH-101 (all $P<0.05$). Data are mean±SEM.

At sexual maturity (~6-7 months), female CFTR+/− pigs were bred to CFTR+/− males. Six litters produced 64 piglets. Genotyping (FIG. 10A) revealed 18 CFTR+/+, 26 CFTR+/−, and 20 CFTR−/− animals, a ratio not significantly different from the expected 1:2:1 (see below). FIG. 10B shows the first litter. Birth weights varied, but did not segregate by genotype (FIG. 10C). Piglets looked normal at birth, and genotype could not be discerned by appearance. A normal appearance is consistent with findings in humans.

Figure 11:
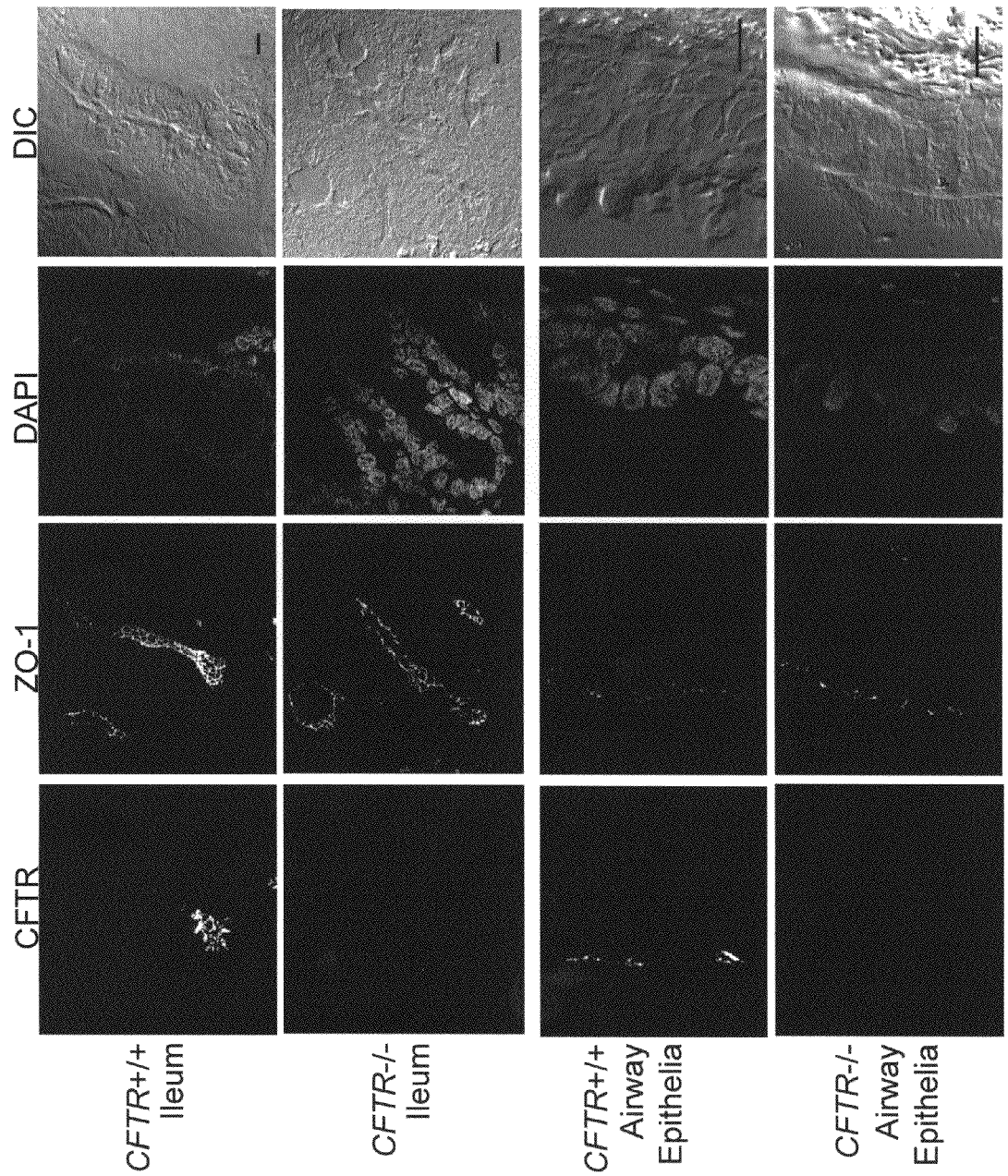
FIG. 11 is images showing staining for CFTR, ZO-1, and DAPI, plus differential interference contrast. Bars, 10 um.

Northern blot and quantitative RT-PCR did not detect normal CFTR transcripts (FIG. 10A). Immunoprecipitation detected no normal CFTR protein. Like human CFTR (Crawford et al., Proc. Natl. Acad. Sci. U S.A. 88:9262, 1991; Denning et al., J. Clin. Invest. 89:339, 1992), the porcine protein localized apically in airway epithelia and ileal crypts (FIG. 10D). Staining for CFTR, ZO-1, DAPI, and differential interference contrast, are shown in FIG. 11.

As in humans, we assessed CFTR function in vivo by measuring transepithelial voltage (Vt) across nasal epithelia (Standaert et al., Pediatr. Pulmonol. 37:385, 2004) (FIG. 10E, F). Like humans with CF, baseline Vt was hyperpolarized in CFTR−/− piglets. Amiloride, which inhibits ENaC Na$^+$ channels, reduced Vt in all genotypes. To test for CFTR channel activity, we perfused the apical surface with a Cl$^-$-free solution and added isoproterenol to increase cellular levels of cAMP; these interventions hyperpolarized nasal Vt in wild-type and heterozygous, but not CFTR−/− animals. Perfusion with ATP to activate P2Y2 receptors and Ca$^{2+}$-activated Cl$^-$ channels (Standaert et al., Pediatr. Pulmonol. 37:385, 2004) further hyperpolarized Vt, and the response did not differ significantly between genotypes. Perfusion with the CFTR inhibitor GlyH-101 (Muanprasat et al., J. Gen. Physiol. 124: 125, 2004) depolarized Vt in controls, but not CFTR−/− piglets. These data reveal loss of CFTR Cl$^-$ channel activity in newborn CFTR−/− pigs. While lack of data from newborn humans precludes direct comparison, the data qualitatively match those from adults and children with CF (Standaert et al., Pediatr. Pulmonol. 37:385, 2004).

Figure 12:
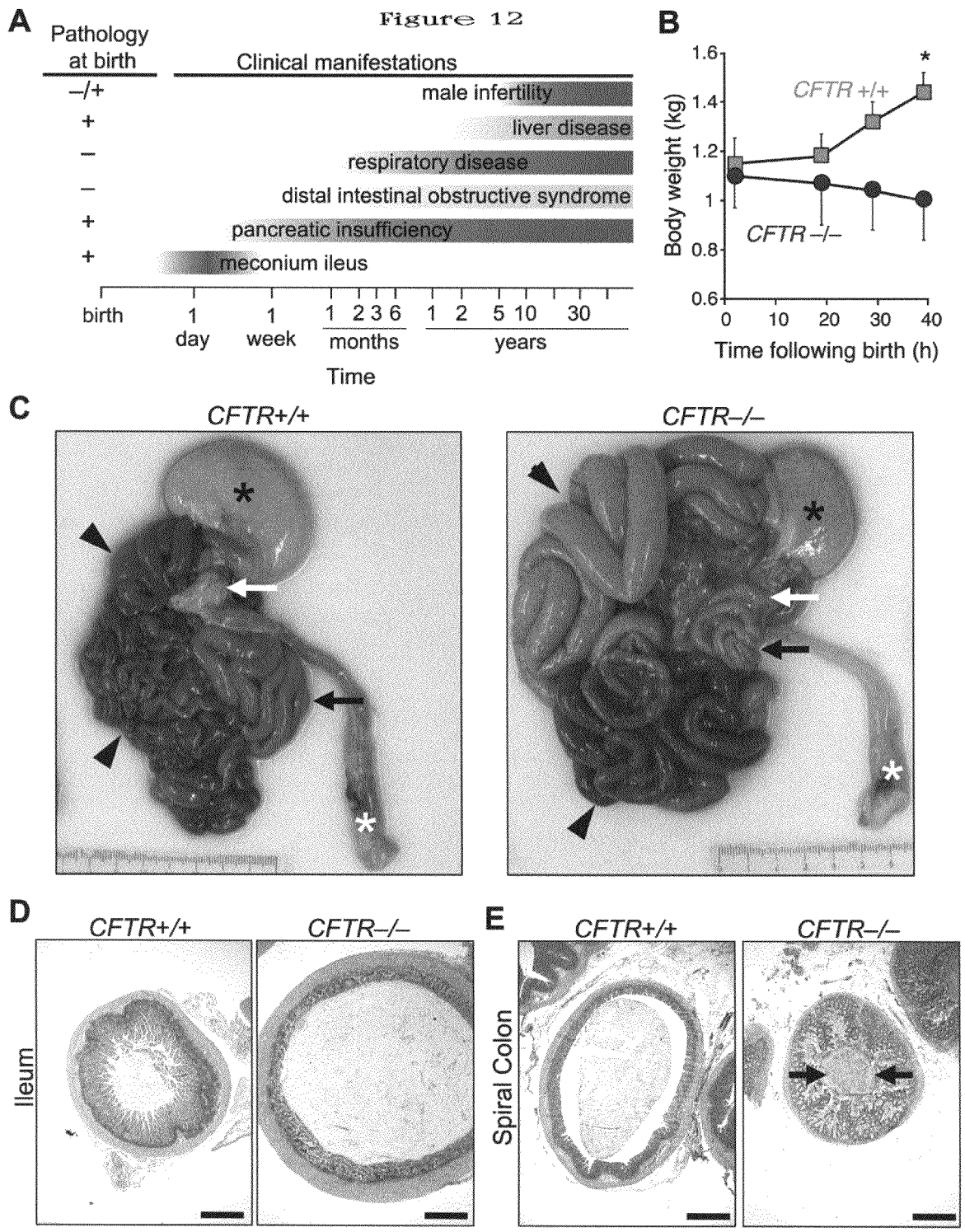
FIG. 12 shows that CFTR−/− piglets develop meconium ileus. A) Schematic shows some clinical and histopathological CF manifestations. Note that pathological abnormalities are present before clinical disease becomes apparent. B) Weight following birth. Animals were fed colostrum and milk-replacer. n=7 CFTR+/+ and 4 CFTR−/−. Data are mean±SEM. *$P<0.05$. C) Gross appearance of gastrointestinal tract. Piglets were fed colostrum and milk-replacer for 30-40 h and then euthanized. Stomach (black *), small intestine (arrowheads), pancreas (white arrow), rectum (white *), and spiral colon (black arrow). Of 16 CFTR−/− piglets, the obstruction occurred in small intestine in 7 and spiral colon in 9. D, E) Microscopic appearance of the ileum (D) and colon (E). H&E stain. Bars, 1 mm. Images are representative of severe meconium ileus occurring in 16 of 16 CFTR−/− piglets.

What phenotypes would be expected if newborn CFTR−/− piglets model human disease? FIG. 12A shows some human CF phenotypes and the time range when they become clinically apparent (Welsh et al., in *The Metabolic and Molecular Basis of Inherited Disease*, C. R. Scriver et al., Eds. (McGraw-Hill, New York, 2001) pp. 5121-5189; Oppenheimer et al., Perspect. Pediatr. Pathol. 2:241, 1975). The earliest manifestation (hours to 2 days) is meconium ileus, an intestinal obstruction occurring in ~15% of CF infants (Quinton, Physiol. Rev. 79: S3, 1999; Welsh et al., in *The Metabolic and Molecular Basis of Inherited Disease*, C. R. Scriver et al., Eds. (McGraw-Hill, New York, 2001) pp. 5121-5189; Oppenheimer et al., Perspect. Pediatr. Pathol. 2:241, 1975; Wilschanski et al., J. R. Soc. Med. 91 Suppl 34:40, 1998). Obstruction can occur throughout the small intestine or colon, but most often occurs near the ileocecal junction. Distal to the obstruction, the bowel is small and atretic (microcolon). Intestinal perforation in utero or postnatally occurs in some infants.

Following birth, CFTR−/− piglets failed to pass feces or gain weight (FIG. 12B). By 24-40 hours, they stopped eating, developed abdominal distension, and had bile-stained emesis. These are clinical signs of intestinal obstruction. We examined histopathology between birth and 12 hours in piglets that had not eaten and between 24 and 40 hours in pigs fed colostrum and milk replacer. Except as noted, the pathologic changes refer to the early time period. After 30-40 hours, CFTR−/− piglets had stomachs containing small amounts of green, bile-stained milk (FIG. 12C). The proximal small intestine was dilated by small amounts of milk and abundant gas. The site of obstruction ranged from mid-distal small intestine to proximal spiral colon, the anatomical equivalent of the human ascending colon. Perforation and peritonitis occurred in some piglets. Dark green meconium distended the CFTR−/− intestine and adjacent villi showed degeneration and atrophy, whereas CFTR+/+ ileum had long villi (FIG. 12D). Distal to the meconium, luminal diameter was reduced with mild to severe mucinous hyperplasia including mucoid luminal "plugs" (FIG. 12E). These changes replicate those in humans with CF (Welsh et al., in *The Metabolic and Molecular Basis of Inherited Disease*, C. R. Scriver et al., Eds. (McGraw-Hill, New York, 2001) pp. 5121-5189; Oppenheimer et al., Perspect. Pediatr. Pathol. 2:241, 1975).

The penetrance of meconium ileus was greater in newborn CFTR−/− piglets (100%) than in newborn humans with CF (~15%). There are several potential explanations for this difference. First, although our pigs were not inbred, they have a more uniform genetic background than humans with CF and hence may show less variability (Blackman et al., Gastroenterology 131:1030, 2006). Second, patients with two CFTR null mutations are very rare, and it is possible that a tiny amount of residual function from CFTR with common CF-associated mutations is sufficient to prevent a greater frequency of meconium ileus in humans. Third, the greater frequency in piglets might be due to anatomical or physiological differences between the species that increase susceptibility to obstruction.

CF mice also develop intestinal abnormalities, although their phenotype differs from the meconium ileus in newborn humans. Some mice die with intestinal disease a few days after birth, and others die around the time of weaning (Clark et al., Lab Anim. Sci. 46:612, 1996; Guilbault et al., Am. J. Respir. Cell Mol. Biol. 36:1, 2007; Grubb et al., Physiol. Rev. 79:S193, 1999). When the intestine was examined before the onset of weight loss, it could appear similar in CFTR+/+ and CFTR−/− mice (Snouwaert et al., Science 257:1083, 1992). In CF mice that developed an obstruction, the intestinal crypts were dilated, villi were atrophic and sometimes necrotic, and there was increased mucus. Thus, in humans, pigs and mice, the intestine is susceptible to loss of CFTR, although the manifestations can differ.

Figure 13:
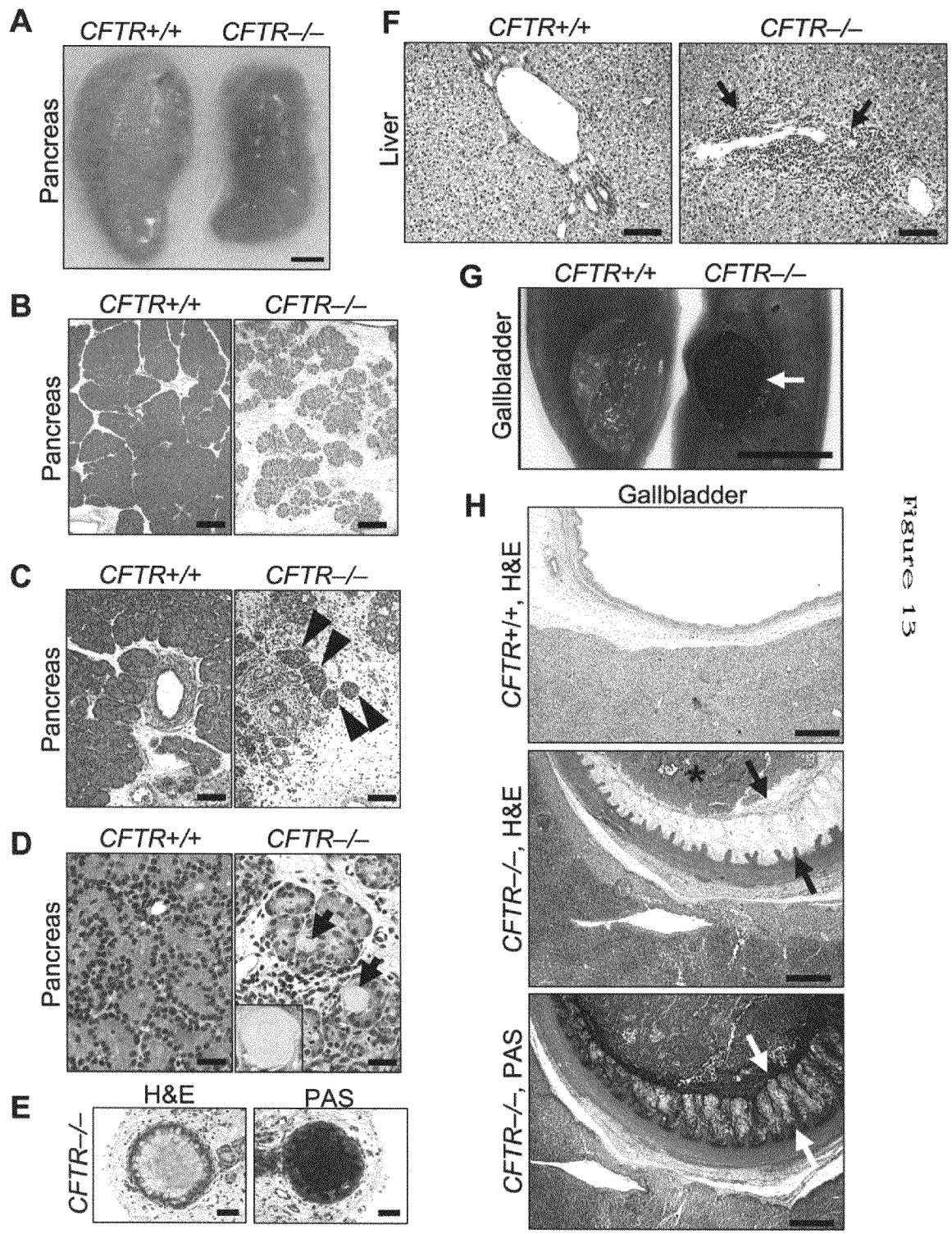
FIG. 13 shows that CFTR−/− piglets have exocrine pancreatic destruction and liver and gallbladder abnormalities. A) Gross appearance of pancreas. Bar, 0.5 cm. B) Loss of parenchyma in the CFTR−/− pancreas. H&E stain. Bars, 500 µm. C) Pancreatic ducts and islets of Langerhans (arrowheads). Bars, 100 µm. D) CFTR−/− ductules and acini dilated by eosinophilic inspissated material that formed concentrically lamellar concretions (arrows and insert). H&E stain. Bars, 33 µm. E) Ducts within the CFTR−/− pancreas. H&E stain, left; PAS stain, right. Bars, 50 µm. F) Microscopic appearance of liver. H&E stain. Arrows indicate focal expansion of portal areas by chronic cellular inflammation. Bars, 100 µm. G) Gross appearance of gallbladder. When the CFTR+/+gallbladder was sectioned, bile drained away rapidly with collapse of the mucosal wall. CFTR−/− bile was congealed (arrow) and retained in the lumen of a smaller gallbladder. Bar, 0.5 cm. H) Microscopic appearance of gallbladder. CFTR−/− gallbladders had congealed, inspissated bile with variable mucus production (arrows, H&E stain) highlighted as a magenta color in periodic acid-Schiff (PAS) stained tissue. Bars, 500 µm. Images are representative of severe pancreatic lesions (15/15 CFTR−/− piglets), mild to moderate liver lesions (3/15), and mild to severe gall bladder/duct lesions (15/15).

Exocrine pancreatic insufficiency afflicts 90-95% of patients with CF (Andersen, Am. J. Dis. Child. 56:344, 1938; Quinton, Physiol. Rev. 79:S3, 1999; Welsh et al., in *The Metabolic and Molecular Basis of Inherited Disease*, C. R. Scriver et al., Eds. (McGraw-Hill, New York, 2001) pp. 5121-5189; Rowe et al., N. Engl. J. Med. 352:1992, 2005; Oppenheimer et al., Perspect. Pediatr. Pathol. 2:241, 1975; Imrie et al., Am. J. Pathol. 95:697, 1979; Blackman et al., Gastroenterology 131:1030, 2006). The porcine CFTR−/− pancreas was small (FIG. 13A). Microscopic examination revealed small, degenerative lobules with increased loose adipose and myxomatous tissue and scattered to moderate cellular inflammation (FIG. 13B,C). Residual acini had diminished amounts of eosinophilic zymogen granules (FIG. 13D). Centroacinar spaces, ductules, and ducts were variably dilated and obstructed by eosinophilic material plus infrequent neutrophils and macrophages mixed with cellular debris (FIG. 13E). Ducts and ductules had foci of mucinous metaplasia. Pancreatic endocrine tissue was spared (FIG. 13C). These changes reflect those originally described by Anderson and others (Andersen, Am. J. Dis. Child. 56:344, 1938; Oppenheimer et al., Perspect. Pediatr. Pathol. 2:241, 1975; Imrie et al., Am. J. Pathol. 95:697, 1979).

In humans with meconium ileus, surgery is often required to relieve intestinal obstruction (Welsh et al., in *The Metabolic and Molecular Basis of Inherited Disease*, C. R. Scriver et al., Eds. (McGraw-Hill, New York, 2001) pp. 5121-5189). Therefore, three CFTR−/− piglets had a laparotomy to remove the obstructing meconium and to place an ileostomy for drainage. We performed an identical procedure in one CFTR+/+ piglet. Two CFTR−/− and the one wild-type piglet were euthanized during the post-operative period because of technical problems in supportive care. One CFTR−/− piglet recovered. We fed him colostrum followed by milk replacer and then standard pig chow. He also received supplemental pancreatic enzymes and fat-soluble vitamins, but not the polyethylene glycol used to treat the intestinal disease in CF mice (Clark et al., Lab Anim. Sci. 46:612, 1996; Guilbault et al., Am. J. Respir. Cell Mol. Biol. 36:1, 2007). The ileostomy closed spontaneously, and he has grown well for eleven weeks. This is the same pattern observed in humans with CF, who once they recover from meconium ileus develop a pattern of disease like patients without meconium ileus (Welsh et al., in *The Metabolic and Molecular Basis of Inherited Disease*, C. R. Scriver et al., Eds. (McGraw-Hill, New York, 2001) pp. 5121-5189).

When we discontinued pancreatic enzymes for three days, the CFTR−/− piglet's well-formed feces became soft, greasy and yellow like steatorrhea in humans with CF, and then reverted to a normal appearance with reinitiation of pancreatic enzymes. This result is consistent with the pancreatic histopathology and clinical pancreatic insufficiency. After ten weeks, he suddenly stopped eating, failed to pass feces, had an episode of vomiting, and the abdomen became distended. These signs resemble the "distal intestinal obstruction syndrome (DIOS)" observed in humans (Welsh et al., in *The Metabolic and Molecular Basis of Inherited Disease*, C. R. Scriver et al., Eds. (McGraw-Hill, New York, 2001) pp. 5121-5189; Dray et al., Clin. Gastroenterol. Hepatol. 2:498, 2004). Therefore, as is done in humans, we treated him with oral polyethylene glycol and performed a Gastrografin enema that revealed the obstruction and relieved it. He then resumed eating and normal behavior. These observations are remarkably similar to meconium ileus, pancreatic insufficiency, and DIOS in humans with CF.

Although these observations came from a single animal, the meconium ileus had a penetrance of 100%, and therefore the successful treatment with surgery is significant. The pig's subsequent course, which has been identical to what we see in humans, further indicates that this CF pig may prove valuable for those interested in CF. It also suggests that it will be possible for the CFTR−/− animals to survive for additional studies focused on CF.

Focal biliary cirrhosis is the second most common cause of CF mortality (Welsh et al., in *The Metabolic and Molecular Basis of Inherited Disease*, C. R. Scriver et al., Eds. (McGraw-Hill, New York, 2001) pp. 5121-5189; Wilschanski et al., J. R. Soc. Med. 91 Suppl 34:40, 1998; Oppenheimer et al., J. Pediatr. 86:683, 1975). The porcine CFTR−/− liver revealed infrequent, mild to moderate hepatic lesions (FIG. 13F). Chronic cellular inflammation, ductular hyperplasia, and mild fibrosis were typical of focal biliary cirrhosis. Gallbladder abnormalities, including gallstones, occur in 15-30% of patients, and a small gallbladder is a common autopsy finding (Welsh et al., in *The Metabolic and Molecular Basis of Inherited Disease*, C. R. Scriver et al., Eds. (McGraw-Hill, New York, 2001) pp. 5121-5189). Similarly, porcine CFTR−/− gallbladders were small and often filled with congealed bile and mucus (FIG. 13G,H). Epithelia showed diffuse mucinous changes with folds extending into the lumen.

Approximately 97% of males with CF are infertile (Welsh et al., in *The Metabolic and Molecular Basis of Inherited Disease*, C. R. Scriver et al., Eds. (McGraw-Hill, New York, 2001) pp. 5121-5189); the vas deferens is often normal at birth, and obstruction is thought to cause progressive deterioration. Although patients are commonly said to have a "congenital" absence of the vas deferens, the incidence of abnormal vas deferens is low in fetuses and young children, and mucinous obstruction is proposed to cause progressive degeneration (Oppenheimer et al., Perspect. Pediatr. Pathol. 2:241, 1975; Gaillard et al., J. Urol. 158:1549, 1997; Oppenheimer et al., J. Pediatr. 75:806, 1969).

In all piglets the vas deferens appeared intact. Paranasal sinus abnormalities occur in most children and adults with CF (Welsh et al., in *The Metabolic and Molecular Basis of Inherited Disease*, C. R. Scriver et al., Eds. (McGraw-Hill, New York, 2001) pp. 5121-5189). Although CFTR−/− porcine paranasal sinuses showed no abnormalities, this negative result is difficult to interpret because it is unclear when sinus disease develops in humans. Salivary glands, nasal cavity, esophageal glands, kidney, heart, striated muscle, spleen, adrenals, eyes, brain, skin, and a few eccrine sweat glands on the snout revealed no abnormalities in CFTR−/− piglets. In all tissues, we observed no differences between wild-type and CFTR+/− animals.

Figure 15:
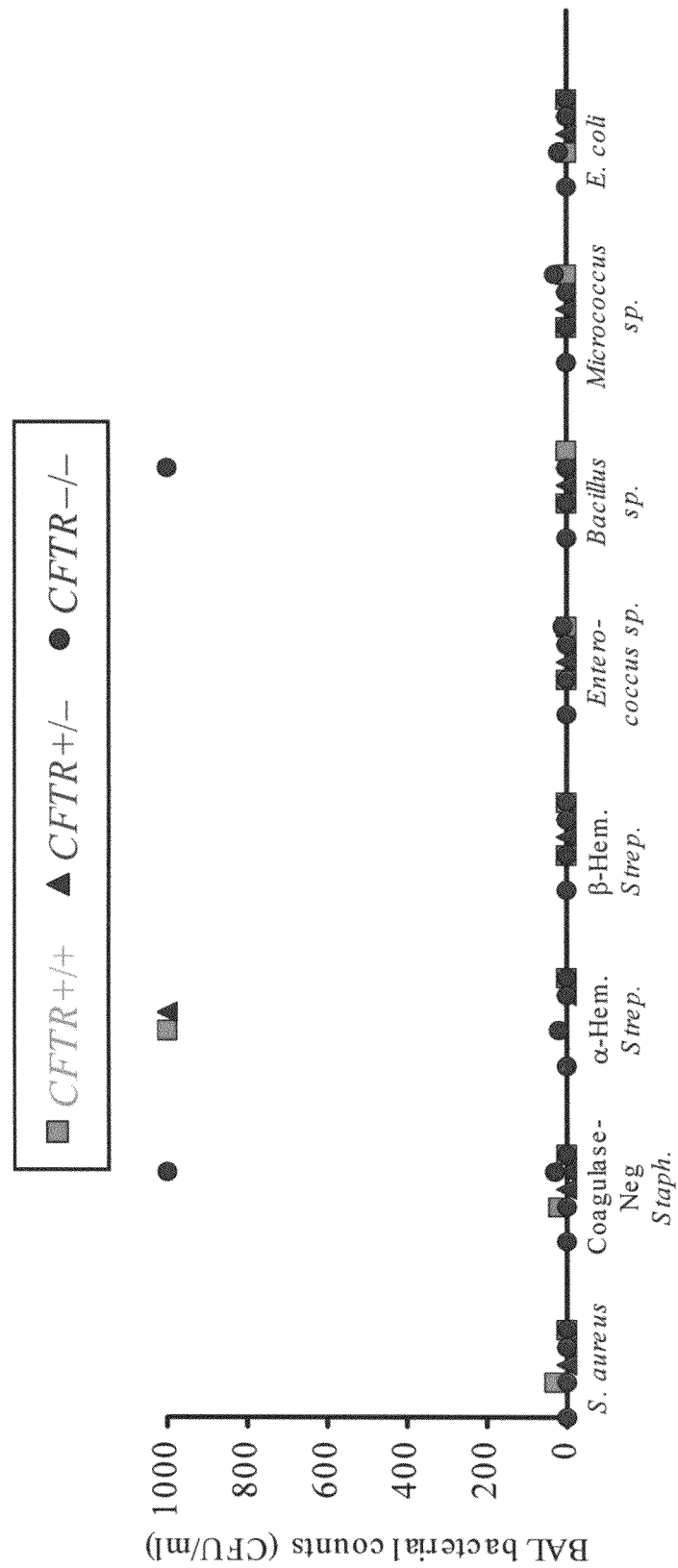
FIG. 15 shows results from bacterial culture of bronchoalveolar lavage fluid obtained from piglets between 6 and 12 hours after birth.
Figure 16:
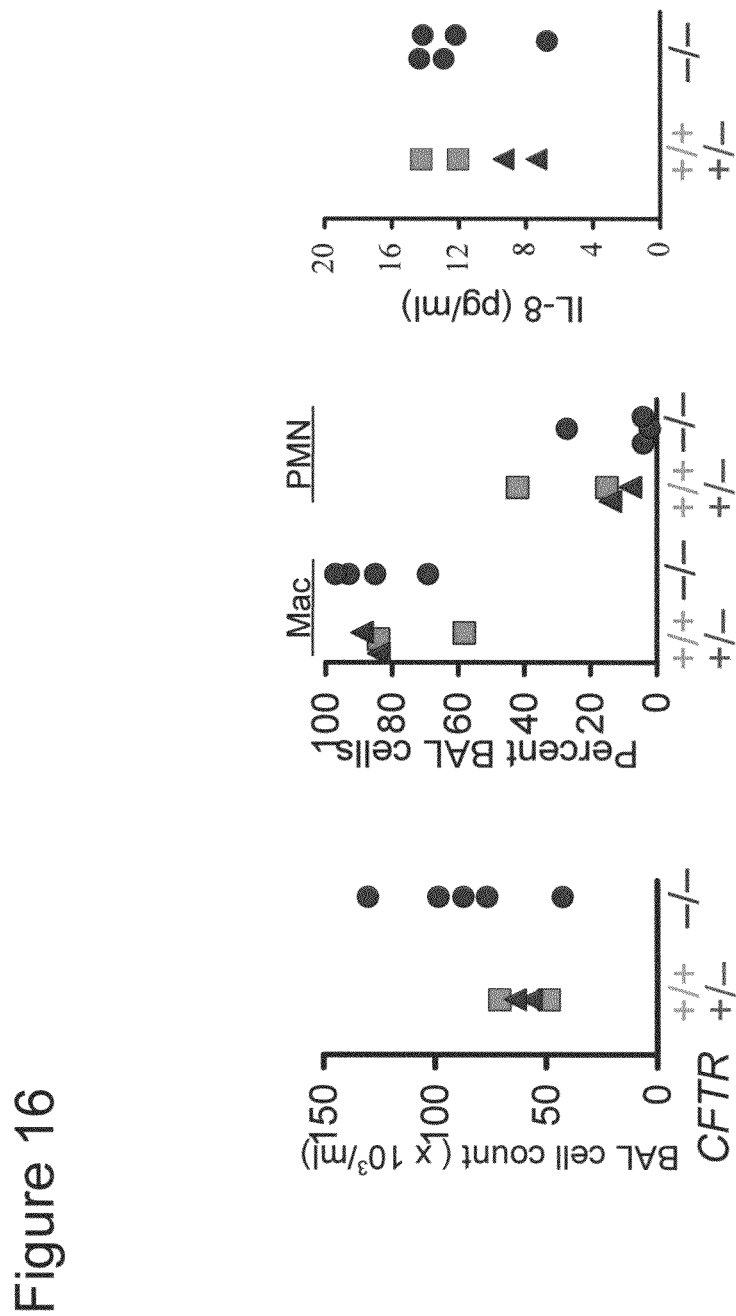
FIG. 16 shows results from bronchoalveolar lavage (BAL) on unfed piglets <12 hours old. Data are total numbers of cells in the lavage, percentages of macrophages and neutrophils, and levels of IL-8. Data are from 2 CFTR+/+, 2 CFTR+/−, and 5 CFTR−/− piglets. Values were not statistically different, $P>0.1$.

Lung disease is currently the major cause of CF morbidity and mortality (Quinton, Physiol. Rev. 79:S3, 1999; Welsh et al., in *The Metabolic and Molecular Basis of Inherited Disease*, C. R. Scriver et al., Eds. (McGraw-Hill, New York, 2001) pp. 5121-5189; Rowe et al., N. Engl. J. Med. 352:1992, 2005). The onset of clinical respiratory manifestations varies with some patients developing symptoms a few months after birth and others after several years. Eventually, most patients develop chronic airway infection and inflammation that destroy the lung. The lungs of neonatal CFTR−/− piglets appeared the same as their littermates. CFTR−/− lungs lacked evidence of cellular inflammation in airways or parenchyma (FIG. 14A). Airway epithelia and submucosal glands appeared similar in all three genotypes, and we found no evidence of dilated or plugged submucosal gland ducts (FIG. 14B). Bronchoalveolar lavage 6-12 hours after birth showed no evidence of infection, and there were no significant differences between cell counts or levels of IL-8 across genotypes (FIGS. 15 and 16).

In neonates with CF, the lung parenchyma and airways appear histologically normal at birth. However, the submucosal glands have sometimes been reported to be abnormal in neonates with CF. A report from Oppenheimer (Hum. Pathol. 12:36, 1981) studied samples from 90 infants and young children with CF and 90 age matched controls. She concluded that there was no difference in tracheobronchial submucosal glands. Two studies have investigated this issue quantitatively. Chow et al. (Eur. J. Ped. 139:240, 1982) examined autopsy material from 21 patients who died within the first 3 weeks of life from meconium ileus. They quantitatively measured submucosal gland size and acinar diameter, and found no difference between CF and non-CF glands. Sturgess and Imrie (Am. J. Pathol. 106:303, 1982) quantitatively examined submucosal glands from patients who had died between birth and 4 months of age. They found no difference between non-CF and CF in multiple measures of submucosal gland size and acinar diameter. However in CF, they reported an increase in the lumen fraction (lumen volume/[acinar cell volume+lumen volume]), an index of dilatation of acini. This increase could be attributed to patients who had lung infection. If only patients who had meconium ileus without obvious pulmonary infection were considered, then there was no difference between the groups. Thus, the evidence suggests a lack of difference between CF and non-CF lungs, including submucosal glands, at the time of birth.

The "chicken and egg" conundrum about whether CF airway inflammation occurs before infection or whether infection precedes inflammation remains a persistent question. Studies of bronchoalveolar lavage in infants and young children have both supported and argued against the presence of inflammation (increased IL-8 and neutrophilia) without infection (Khan et al., Am. J. Respir. Crit. Care Med. 151: 1075, 1995; Armstrong et al., Pediatr. Pulmonol. 40:500, 2005). In vitro airway epithelial models have also given conflicting results (Stecenko et al., Inflammation 25:145, 2001; Aldallal et al., Am. J. Respir. Crit. Care Med. 166, 1248, 2002). Studies of human fetal trachea transplanted into mice suggested inflammation might occur in developing CF airways (Tirouvanziam et al., Am. J. Respir. Cell Mol. Biol. 23, 121, 2000). While our data do not resolve this controversy, we had the advantage of studying lungs between birth and 12 hours, and we found no evidence of abnormal infection or inflammation. Tracking the lungs as CFTR−/− piglets are exposed to additional environmental challenges should inform understanding of how respiratory disease develops during childhood and in young adults.

The clinical, electrophysiological, and pathological findings in newborn CFTR−/− pigs were remarkably similar to those in human neonates with CF (Table 4). Abdominal lesions dominate the initial presentation in both, with identical appearance of meconium ileus and exocrine pancreatic destruction. In addition, both have hepatic changes consistent with early focal biliary cirrhosis and abnormalities of the gallbladder and bile ducts. The lack of abnormalities in vas deferens and lungs at birth is another similarity. Finding that the phenotype of newborn CFTR−/− piglets copies that of human newborns with CF suggests this model should provide investigators with new opportunities to understand the disease and develop novel prevention and treatment strategies. In addition, there are many other human diseases in which knock-out and knock-in mice fail to reproduce typical human phenotypes and fail to predict responses to therapeutics. This development of a gene-targeted, mammalian disease model, other than a mouse, also suggests strategies to circumvent research bottlenecks presented by limitations of mice.

and were not fed. The other group was fed colostrum and milk replacer and studied between 24 and 40 hours.

Genotyping

Genotyping was performed using genomic DNA isolated from fresh umbilical cord. Tissue was lysed for 15 min at 55° C. in lysis buffer (50 mM KCl, 1.5 mM $MgCl_2$, 10 mM Tris-Cl, pH 8.5, 0.5% Nonidet P40, 0.5% Tween, 400 μg/ml Proteinase K) (McCreath et al., Nature 405:1066, 2000). Two μl of lysate were used in each PCR (Platinum Taq HF, Invitrogen). PCR conditions: 2 minutes at 95° C., 30 cycles of 95° C. for 20 seconds, 56° C. for 20 seconds, and 68° C. for 4 minutes, then 68° C. for 5 minutes. Primers Ex10a5F (AGAATTTCATTCTGCTCTCAGT; SEQ ID NO:35) and GC7R (GAAGACCCTTTACCTTCTTCTA; SEQ ID NO:36) amplify a 2.0 kb product from wild-type CFTR alleles and a 3.7 kb product from gene-targeted CFTR alleles. PCR products were electrophoresed on a 1.0% agarose gel. For Southern blotting, 10 μg of genomic DNA was digested with BglII overnight. Genomic digests were electrophoresed

TABLE 4

Pathological changes in newborn CFTR−/− piglets and human neonates with CF.

| Organ | Tissue | Lesions in newborn CFTR−/− piglets | Detectable in human neonates with CF |
|---|---|---|---|
| Pancreas | Parenchyma | Reduced amounts of exocrine tissue with increased adipose and connective tissue filling the void | Yes |
| | Ducts/ductules | PAS+ eosinophilic inspissated material and mucus filling lumen; ductular hyperplasia | Yes |
| | Acini | Eosinophilic material with rare mucus; atrophic and degenerated acinar cells; reduced zymogen granules | Yes |
| | Inflammation | None to moderate lymphoid and eosinophilic infiltrate; scattered neutrophils and macrophages in dilated acini and ducts | Yes |
| Intestine | Duodenum | Brunner glands dilated by inspissated mucus | Yes |
| | Distal small intestine to proximal colon | Meconium ileus/obstruction | Yes |
| | Proximal to obstruction | Dilated intestine filled with sticky, viscous meconium | Yes |
| | Distal to obstruction | Small intestine/colon small, stenotic; variably filled with mucus | Yes |
| | Complications | In utero perforation, chronic peritonitis, atresia | Yes |
| Liver | Portal regions | Focal biliary cirrhosis; variable ductular hyperplasia, fibrosis, and inflammation | Yes |
| | Biliary duct/ductules | Eosinophilic material/mucus in lumen; scattered Neutrophils | Yes, rare |
| Gallbladder | Lumen | Small and variably filled with inspissated bile and mucus | Yes |
| | Cystic duct | Obstructed by mucus and eosinophilic material | Yes |
| Vas deferens | Duct | None | ± |
| Lung | Parenchyma | None; no inflammation or infection | No |
| | Airways | None; no inflammation or infection | No |

For references to histopathological changes in humans see Standaert et al., Pediatr. Pulmonol. 37: 385, 2004; Blackman et al., Gastroenterology 131: 1030, 2006; Clark et al., Lab Anim. Sci. 46: 612, 1996; Oppenheimer et al., Perspect. Pediatr. Pathol. 2: 241, 1975; Gaillard et al., J. Urol. 158: 1549, 1997; Oppenheimer et al., J. Pediatr. 75: 806, 1969; Oppenheimer et al., Hum. Pathol. 12: 36, 1981; Chow et al., Eur. J. Ped. 139: 240, 1982; Sturgess et al., Am. J. Pathol. 106: 303, 1982; Wilschanski et al., J. R. Soc. Med. 91 Suppl 34: 40, 1998; Imrie et al., Am. J. Pathol. 95: 697, 1979; Oppenheimer et al., J. Pediatr. 86: 683, 1975.

Materials and Methods

Animals

We previously reported production of CFTR+/− male and female pigs (Rogers et al., J. Clin. Invest. 1118(4):1571, 2008). For this study, they were crossed and the progeny studied.

Standard procedures for animal husbandry were used throughout. The Institutional Animal Care and Use Committees of the University of Iowa and the University of Missouri approved all animal experiments. We studied two groups of animals. One group was studied between birth and 12 hours on a 0.7% agarose gel and transferred to a positively charged nylon membrane (Roche) using an alkaline transfer procedure. Blots were pre-hybridized for 15 min at 65° C. in Rapid-hyb buffer (Amersham). The blot was then hybridized in Rapid-hyb buffer with a $^{32}$P-labeled probe specific for a region of CFTR that is outside of the targeting vector boundaries. The blot was washed once in 2×SSC/0.1% SDS for 20 minutes at room temperature followed by two washes in 0.1×SSC/0.1% SDS for 15 minutes at 65° C. Signal was detected using a phosphorimager. The CFTR probe hybridizes at 7.9 kb for wild-type CFTR alleles and 9.7 kb for gene-targeted CFTR alleles.

Northern Blot

Northern blot was performed using total RNA isolated from ileum (RNeasy, Qiagen). Total RNA was electrophoresed on a denaturing gel and transferred to a positively-charged membrane (NorthenMax, Ambion). The membrane was hybridized with $^{32}$P-labelled DNA probes corresponding to nucleotides 1-1000 of the porcine CFTR cDNA or 1-1002 of porcine GAPDH cDNA. Signal was detected using a Fuji FLA7000 phosphorimager. Porcine CFTR mRNA was detected at ~6.5 kb and GAPDH mRNA at 1.5 kb.

Quantitative RT-PCR

Quantitative RT-PCR using TaqMan chemistry and an ABI 7500 Fast Real-time PCR System was used to measure porcine CFTR mRNA. Briefly, total RNA was isolated from ileum (RNeasy, Qiagen). First-strand cDNA was synthesized with oligo-dT primers (SuperScript II, Invitrogen). Sequence-specific primers and probes for porcine CFTR and GAPDH were designed and ordered using Assays-by-design (Applied Biosystems). For measuring CFTR mRNA, primer/probe sets annealing to exon 10 of CFTR and GAPDH were used in separate reactions (CFTR, Forward: TCATGCCGGGCACCATTAAA; SEQ ID NO:37, Reverse: CGCTTTGATGACACTCCTGTATCTA; SEQ ID NO:38, Probe FAM-ACACCAAAGATGATGTTTTC; SEQ ID NO:39; GAPDH, Forward: AAGCTCATTTCCTCGTAC-GACAAT; SEQ ID NO:40, Reverse: GGAGGCCATGTG-GACCAT; SEQ ID NO:41, Probe: FAM-TCCACCACCCT-GTTGCT; SEQ ID NO:42). TaqMan Fast Universal PCR Master Mix was used for all reactions. The reaction volume was 20 μl (10 μl of 2× Master Mix without UNG, 1 μl of 20× target primer and probe, 8 μl of Nuclease-free water, and 1 μl of cDNA sample). The reaction plates were covered with optical film and centrifuged briefly. The thermocycler conditions were as follows: 20 seconds at 95° C., 40 cycles of 95° C. for 3 seconds and 60° C. for 30 seconds. All experiments were run in triplicate. Because the efficiencies of CFTR and GAPDH amplification were not equal, the relative quantification of transcript levels was performed using the standard curve method.

Immunoprecipitation and Phosphorylation

We used lysis buffer with 1% NP-40 and centrifugation as previously described (Ostedgaard et al., Proc. Natl. Acad. Sci. U.S.A. 104:15370, 2007) to prepare soluble protein from cultured airway epithelial cells. Equal amounts (750 μg) of soluble protein were immunoprecipitated with M3A7 antibody (Upstate Technology) and then in vitro phosphorylated as described previously (Ostedgaard et al., Proc. Natl. Acad. Sci. U.S.A. 104:15370, 2007). Immunoprecipitated, phosphorylated proteins were electrophoresed on 6% PAGE, the gels dried and then exposed to phosphorscreen before scanning on Fuji FLA7000 (Fuji Corp.). BHK cells stably expressing wild-type CFTR (a gift from Dr. Gergely Lukacs) were used as controls (7.5 μg) and were treated similarly.

Histopathology

Tissues were collected at necropsy and immediately placed in a bath of 10% neutral buffered formalin and gently agitated for a minimum of 72 hours. Tissues were then processed, paraffin-embedded, sectioned (4-5 μm) and stained with hematoxylin and eosin (H&E) or periodic acid-Schiff (PAS). Histopathological examination was performed by a veterinary pathologist blinded to pig genotype. This allowed for unbiased pathological assessment of tissues ranging from mild/moderate multifocal lesions (e.g., liver parenchyma) to severe lesions with 100% penetrance (e.g., pancreas).

Measurement of Nasal Vt

The transepithelial voltage (Vt) across the nasal epithelium was measured using previously described methods (Zabner et al., J. Clin. Invest. 97:1504, 1996; Standaert et al., Pediatr. Pulmonol. 37:385, 2004) under propofol anesthesia with the animal spontaneously breathing. The reference electrode was a small Ringer's solution-filled catheter inserted into the leg muscle (25 g needle). The exploring electrode was a 6 french foley catheter filled with Ringer's solution (148 mM NaCl, 2.4 mM $KH_2PO_4$, 0.4 mM $K_2PO_4$, 2.25 mM $CaCl_2$, 1.2 mM $MgCl_2$) inserted 4 cm into the nasal cavity, and the nasal mucosa was perfused at a rate of 5 ml/min using Ringer's solution to obtain baseline Vt. Subsequent perfusion solutions included: Ringer's solution containing 100 μM amiloride; $Cl^-$-free Ringer's solution containing gluconate substituted for $Cl^-$ plus amiloride; $Cl^-$-free Ringer's solution containing amiloride plus 10 μM isoproterenol; $Cl^-$-free Ringer's solution containing amiloride, isoproterenol, plus 100 μM ATP; $Cl^-$-free Ringer's solution containing amiloride, isoproterenol, ATP, plus 100 μM GlyH-101. Voltage was measured with a voltmeter connected to a strip chart recorder. Each solution was perfused for 3-5 minutes. Following completion of the measurements, the epithelium was disrupted by brushing and Vt measured again to determine the zero value of Vt.

Immunocytochemistry

Ileal and tracheal tissues were excised from newborn piglets, immediately placed in ice-cold 30% sucrose, and quick frozen in OCT. Tissues were cryosectioned at 7 μm thick onto polylysine-coated microscope slides, fixed in 100% MeOH at −20° C. for 15 min, permeabilized in 0.2% TX-100 (Thermo Scientific) in PBS, and blocked in Super-Block (Thermo Scientific) with 5% normal goat serum (Jackson ImmunoResearch). Tissue sections were incubated overnight at 4° C. in anti-CFTR antibodies MM13-4, M3A7 (Chemicon), and 24-1 (R&D Systems) and polyclonal antibody to ZO-1 (Zymed) (all at 1:100 dilution), followed by secondary antibodies (goat-anti-mouse A488 and goat anti-rabbit A568 (Molecular Probes) (1:1000 dilution). Sections were mounted with Vectashield containing DAPI (Vector Labs) to visualize nuclei. Images were acquired on an Olympus Fluoview FV1000 confocal microscope with a UPLSAPO 60X oil lens, 1.35 NA. Images were scanned sequentially at 2 μsec/pixel. Images were processed identically using Fluoview FV10-ASW-1.6 confocal software. RGB images were converted to white images for green and red channels and overlayed on a single Z-section of DIC with DAPI for merged image.

Bronchoalveolar Lavage (BAL) Fluid Collection and Analysis

Animals were studied between 6 and 12 hours after birth. BAL was performed immediately following euthanasia. We instilled 5 ml of normal saline through an intratracheal catheter three times. The total number of recovered cells was quantified with a hemacytometer and morphologic differentiation of cells was performed on cytospin preparations that were stained with Diff-Quick Stain-kit (Baxter). BAL levels of IL-8 were determined on recovered supernatant after centrifugation (1600×g for 10 min). IL-8 levels were measured by antibody capture assay (Thermo Scientific). Standard quantitative microbiologic techniques were used to identify and quantitate the bacteria in BAL.

Statistical Analysis

Data are presented as either mean±standard error of the mean (SEM) or individual data points. Statistically significant differences between genotype groups were determined using either the Student's t-test or one-way ANOVA and the Student-Newman-Keuls test to determine group differences. Differences were considered statistically significant for $P<0.05$.

III. The ΔF508 Mutation—an Interspecies Analysis

The ΔF508 mutation confers at least three defects on human CFTR: it reduces channel activity, it impairs processing, and it reduces the protein's stability at the cell surface. The ΔF508 mutation inhibits gating of CFTR channels from three species (i.e., mouse, pig, and human) studied by the same mechanism, a reduced opening rate. In contrast, the characteristic processing defect observed in human CFTR-ΔF508 is less severe in pig and mouse proteins. This conclusion is supported by our finding that the mouse and pig proteins showed complex glycosylation, were readily excised for patch-clamp experiments at 37° C., immunocytochemistry localized some of the protein to the apical membrane of airway epithelia, and corrected the Cl⁻ transport defect in CF airway epithelia more than did human CFTR-ΔF508. This shows that there is a gradient in the severity of the ΔF508 processing defect, with human worse than pig, and pig somewhat worse than mouse. Additionally, this also shows that the processing defect and the functional defect in CFTR-ΔF508 arise from different causes.

Vectors and Expression

Human, pig, and mouse CFTR cDNA (SEQ ID NOs: 1, 3, and 5) were amplified from *Homo sapiens*, domestic pig (*Sus scrofa*), and domestic mouse (*mus musculus*). We subcloned all three CFTR cDNAs into pcDNA3.1 (Invitrogen) and recombinant adenoviruses. For recombinant adenovirus of mouse CFTR, we had to remove intron 11 which had been inserted previously to stabilize the vector.

For protein processing studies, COS7 cells were electroporated; 3T3 and LLC-PK1 cells were transfected with plasmid and Lipofectamine 2000. For deglycosylation studies, COS7 cells were electroporated with human CFTR or infected with adenovirus encoding pig or mouse CFTR. For patch-clamp studies, HeLa cells were infected with adenovirus encoding mouse CFTR or transfected using a hybrid vaccinia virus system encoding pig CFTR. Expression in human and mouse airway epithelia was with recombinant adenoviruses. Murine tracheal epithelia were cultured from ΔF508/ΔF508 transgenic mice (CFTR$^{tm1Kth}$) or CFTR null mice expressing the intestinal FABP-CFTR (CFTR$^{tm1UnC/FABP-CFTR}$). In the absence of gene transfer, there were no cAMP-stimulated Cl⁻ currents in either mouse genotype.

Biochemical Studies

COS7 cells were solubilized in lysis buffer with 1% TX-100 and proteinase inhibitors. CFTR was immunoprecipitated with M3A7 antibody (Upstate Technology) and then in vitro phosphorylated as described previously. Note that the consensus phosphorylation sites and N-glycosylation sites are conserved in all three species (FIG. 17). Processing studies in NIH-3T3 and LLC-PK1 cells were carried out similarly to those in COS7 cells. For deglycosylation studies, membranes were isolated from COS7 cells and solubilized in LB plus 1% NP40 (Pierce). Supernatants were divided, immunoprecipitated, and resuspended with or without endoglycosidase H. Following incubation, precipitates were in vitro phosphorylated.

Immunocytochemistry

Three days following gene transfer, epithelia were fixed, permeabilized, and incubated with a mixture of anti-CFTR antibodies (M3A7, MM13-4 (Upstate Biotechnology) and 13-1 (R&D Systems) and anti-ZO-1 (Zymed) primary antibodies, followed by Alexa Fluor-conjugated secondary antibodies (Molecular Probes) and examined by confocal laser scanning microscopy.

Electrophysiology

For Ussing chamber studies, transepithelial Cl⁻ current was measured 3 days following gene transfer using a Cl⁻ concentration gradient as previously described. For patch-clamp studies CFTR currents were studied in excised, inside-out membrane patches of HeLa cells as previously described. Channels were activated with the catalytic subunit of PKA and Mg-ATP; PKA was present in all cytosolic solutions that contained ATP. Holding voltage was −50 to −100 mV. Experiments were performed at 23-26° C. Data acquisition, processing, and analysis were performed as previously described. Data are mean±SEM unless otherwise stated. P<0.05 was considered statistically significant.

Sequence of Pig CFTR

We cloned the pig CFTR cDNA and used it to predict the amino acid sequence (FIG. 17). The pig CFTR amino acid sequence is nearly 93% identical to that of human CFTR. For comparison, mouse CFTR shows 78% identity to human CFTR. The region immediately surrounding F508 is highly conserved.

Glycosylation of Human, Pig, and Mouse CFTR-ΔF508

Figure 18:
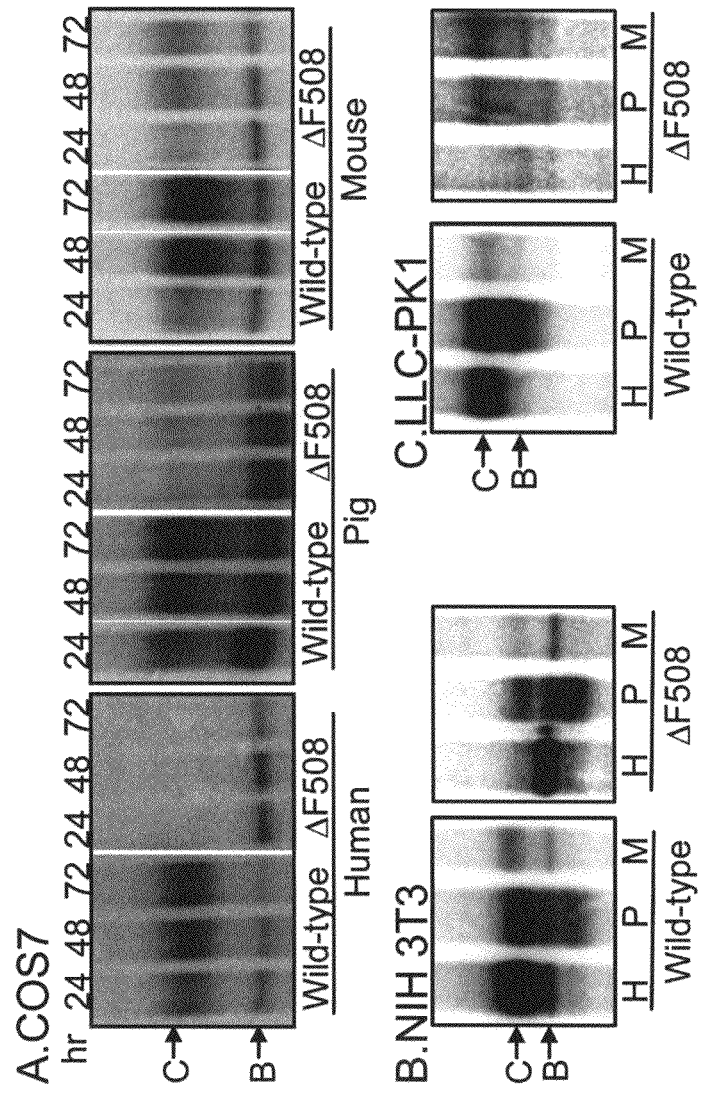
FIG. 18 shows that pig and mouse CFTR-ΔF508 produce some mature band C protein. The images show immunoprecipitated and in vitro phosphorylated wild-type and ΔF508 CFTR of human, pig, and mouse. A. Constructs were expressed for 24, 48, and 72 hours in COS7 cells. B and C. Constructs were expressed for 48 hours in NIH-3T3 (B) and LLC-PK1 (C) cell lines. H, human; P, pig; M, mouse. Bands B and C are indicated by arrows.

The pattern of human CFTR glycosylation changes as the protein migrates from the ER to the Golgi complex. The nascent protein lacking glycosylation is called "band A." In the ER, CFTR undergoes core glycosylation and migrates more slowly during electrophoresis as "band B." In the Golgi complex, more extensive glycosylation occurs, which further slows and broadens the electrophoretic migration of the "band C" form. Differences in glycosylation do not appear to affect function, but do provide a convenient way to assess the biosynthetic processing of CFTR. When we expressed wild-type human, pig, and mouse CFTR in the monkey kidney cell line COS7, we observed the typical appearance of bands B and C (FIG. 18A). Human CFTR-ΔF508 produced band B, but not band C, consistent with defective exit from the ER. This result agrees with many previous reports in several different cell lines. Surprisingly, in addition to band B, mouse CFTR-ΔF508 generated a significant proportion of band C protein. Pig CFTR-ΔF508 also produced a small amount of band C. These results suggested that some mouse and pig mutant protein may have trafficked to the Golgi complex.

To learn whether the differences between the three species of CFTR-ΔF508 depended on the primate COS7 cell line, we expressed the constructs in the mouse NIH-3T3 fibroblast line and the pig LLC-PK1 kidney cell line (FIGS. 18B and C), as well as human HEK-293T cells (not shown). In each of these cell lines, human CFTR-ΔF508 generated only the band B form, whereas pig and mouse CFTR-ΔF508 produced both band B and some fully glycosylated protein, consistent with our studies in COS7 cells. We also noted that some of the wild-type and ΔF508 pig CFTR migrated slightly more rapidly than band B of either human or mouse.

Figure 19:
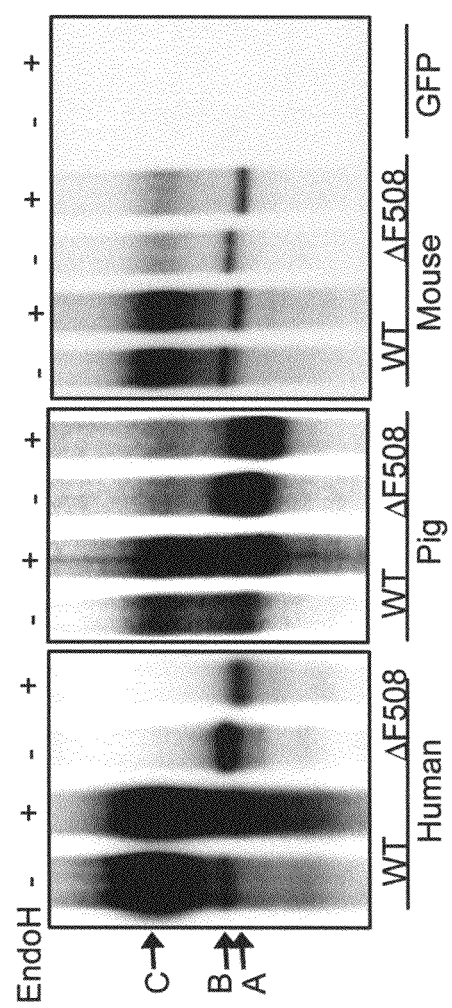
FIG. 19 shows that fully glycosylated pig and mouse ΔF508 are not endoglycosidase-H sensitive. The images show immunoprecipitated and in vitro phosphorylated human, pig, and mouse wild-type and ΔF508 CFTR incubated in the presence (+) or absence (−) of 10 mU of endoglycosidase H. Human CFTR was from electroporated COS7 cells; we expressed pig and mouse CFTR using adenoviral vectors. The last 2 lanes are COS7 cells infected with Ad-GFP. Bands A, B, and C are indicated by arrows.

To confirm that the high molecular mass C forms of pig and mouse CFTR-ΔF508 were due to complex glycosylation, we used endoglycosidase H digestion. Endoglycosidase H removes carbohydrate from proteins that contain only the sugar added in the ER, but it does not delete complex glycosylation added in the Golgi complex. Endoglycosidase H treatment shifted the migration of the band B form of all the proteins to the unglycosylated form (FIG. 19). However, like the band C form of the wild-type CFTRs, the fully glycosylated mouse and pig CFTR-ΔF508 were resistant to endoglycosidase H, confirming that these proteins were glycosylated in the Golgi complex.

Expression of Human, Pig, and Mouse CFTR-ΔF508 at the Cell Surface

Figure 20:
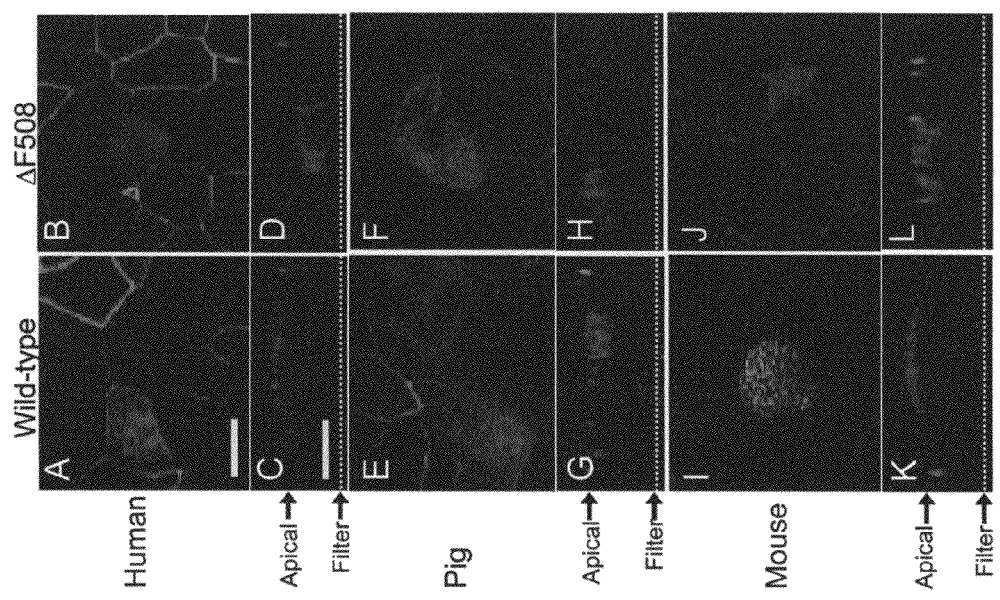
FIG. 20 shows that human, pig, and mouse wild-type CFTR and pig and mouse CFTR-ΔF508 are expressed on the apical surface of differentiated airway epithelia. Immunostaining of differentiated human CF airway epithelia expressing human, pig, and mouse wild-type and ΔF508 CFTR. Data are X-Y (A,B,E,F,I,J) and X-Z (C,D,G,H,K,L) confocal images. CFTR immunostaining is in green and ZO-1 (tight junction) in red. Apical membrane is shown by arrow and filter (at the basal membrane) is indicated by dotted line. In panel B, faint staining of CFTR-ΔF508 is visible beneath the apical surface. Bar indicates 10 µm.

To determine if the human, pig and mouse CFTR-ΔF508 were localized at the apical membrane of airway, we expressed the proteins in well-differentiated human CF airway epithelia and examined them with confocal immunocytochemistry. Consistent with earlier studies, wild-type human CFTR localized at the apical membrane and human CFTR-ΔF508 appeared to be expressed diffusely throughout the cell (FIG. 20). As expected from the biochemical studies, both pig and mouse wild-type were localized to the apical membrane. However, in contrast to human CFTR-ΔF508, both the pig and mouse mutants were also present in the apical portion of the airway cells.

Single Channel Gating of Human, Pig, and Mouse CFTR-ΔF508

Figure 21:
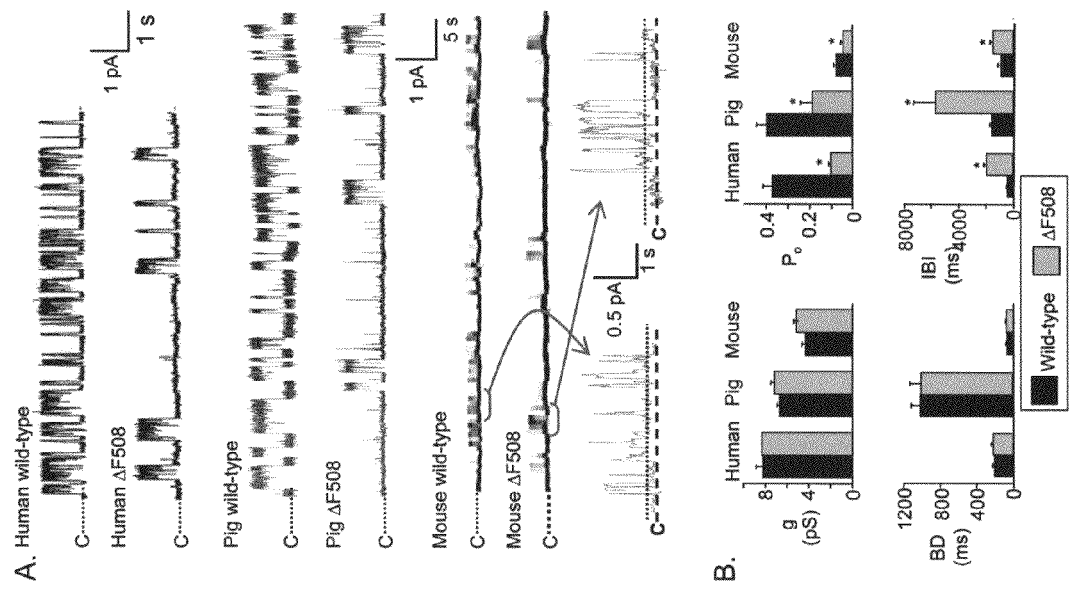
FIG. 21A shows single-channel currents from human, pig, and mouse wild-type and ΔF508 CFTR. Representative current traces from excised, inside-out patches of HeLa cells containing single channels of human, pig, and mouse wild-type and ΔF508 CFTR. Holding voltages were human at −80 mV, pig at −100 mV, mouse wild-type at −50 mV, and mouse ΔF508 at −80 mV. Human tracings were from cells incubated at reduced temperature and then studied at 37° C. and are taken from Teem et al. (Receptors Channels 4:63-72, 1996); pig and mouse channels were from cells incubated at 37° C. and studied at ~25° C. Expanded tracings on bottom show sub-conductance in mouse wild-type and ΔF508 CFTR.
FIG. 21B shows the properties of wild-type and ΔF508-CFTR. Data are mean±SEM for single-channel conductance (g), open state probability ($P_o$), burst duration (BD), and inter-burst interval (IBI). n=4-5 membrane patches for each. Asterisks indicate $p<0.05$ compared to wild-type CFTR using Mann-Whitney Rank Sum test. Note that values for human CFTR and CFTR-ΔF508 were taken from Teem et al. (Receptors Channels 4:63-72, 1996).

Most, although not all studies indicate that human CFTR-ΔF508 manifests a channel gating defect that reduces activity. To learn whether the ΔF508 mutation compromises the channel activity in pig and mouse CFTR, we studied excised, inside-out patches of membrane containing CFTR channels. We readily detected channels in patches taken from cells expressing pig and mouse CFTR-ΔF508 grown at 37° C., consistent with the conclusion that pig and mouse CFTR-ΔF508 are able to reach the cell membrane under physiological conditions. This contrasts with human CFTR-ΔF508, which must be incubated at lowered temperatures to produce significant amounts of cell surface protein. Phosphorylation by the catalytic domain of cAMP-dependent protein kinase (PKA) and cytosolic ATP were required for activity of all versions studied. The single channel conductances for the wild-type channels were human (8.3 pS)>pig (6.7 pS)>mouse (4.3 pS), and they were not significantly altered by the ΔF508 mutation (FIGS. 21A and 21B). Lansdell et al. (J. Physiol. 508:379-392, 1998) reported that heavily filtering currents recorded from mouse CFTR revealed a subconductance state that was ~10% the amplitude of the full conductance. With heavy filtering, we also observed the subconductance in both wild-type and ΔF508 channels (FIG. 21A).

In the presence of PKA and 1 mM ATP, the open state probability ($P_o$) of wild-type CFTR varied in the order, pig (0.39)≈human (0.37)>mouse (0.08) (FIG. 21B); the values for human were taken from our earlier study. In assessing mouse $P_o$, we did not take into account the subconductance state; as reported by Lansdell et al., it was very difficult to study due to its small single-channel conductance. The ΔF508 mutation reduced the $P_o$ of human CFTR to 27%, pig CFTR to 46%, and mouse CFTR to 50% of the corresponding wild-type channel (FIGS. 21A and 21B). The cause of the reduced $P_o$ was a decrease in the rate of channel opening without a significant alteration of burst duration (FIG. 21B). Thus, in all three species, the ΔF508 mutation altered gating by a similar mechanism.

Transepithelial Cl⁻ Current Generated by Human, Mouse, and Pig CFTR-ΔF508

Because both pig and mouse CFTR-ΔF508 were partially processed through the Golgi complex and likely targeted to the apical membrane, and because they both retained partial Cl⁻ channel activity, we predicted they would generate transepithelial Cl⁻ currents when expressed in well-differentiated CF airway epithelia. To assay transepithelial Cl⁻ transport, we mounted epithelia in modified Ussing chambers and measured transepithelial Cl⁻ current. We first inhibited Na⁺ current with amiloride, which hyperpolarizes the apical membrane voltage, increasing the driving force for Cl⁻ secretion through CFTR. Then, we increased CFTR activity by elevating cellular levels of cAMP with forskolin and IBMX. Finally, we reduced transepithelial Cl⁻ current by inhibiting the Na⁺—K⁺—Cl⁻ cotransporter with basolateral bumetanide; the resulting change in current provides a good measure of the Cl⁻ current. We chose bumetamide rather than CFTR inhibitors, because they can have different efficacy on CFTR from different species.

Figure 22:
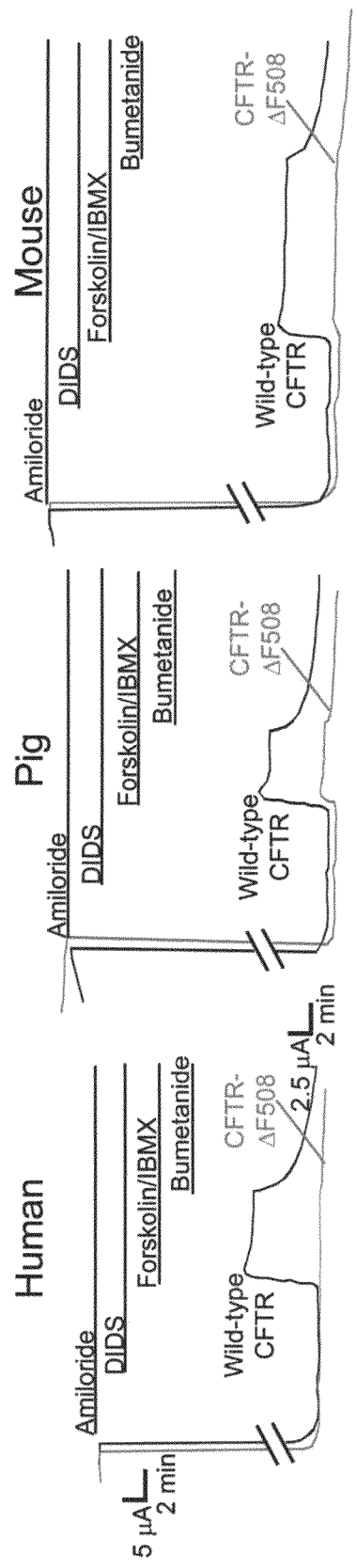
FIG. 22 shows transepithelial currents in human CF airway epithelia expressing human, pig, and mouse CFTR and CFTR-ΔF508. Examples of current traces of human, pig, and mouse wild-type CFTR and CFTR-ΔF508 expressed in differentiated human CF airway. Agents were present during times indicated by bars.
Figure 23:
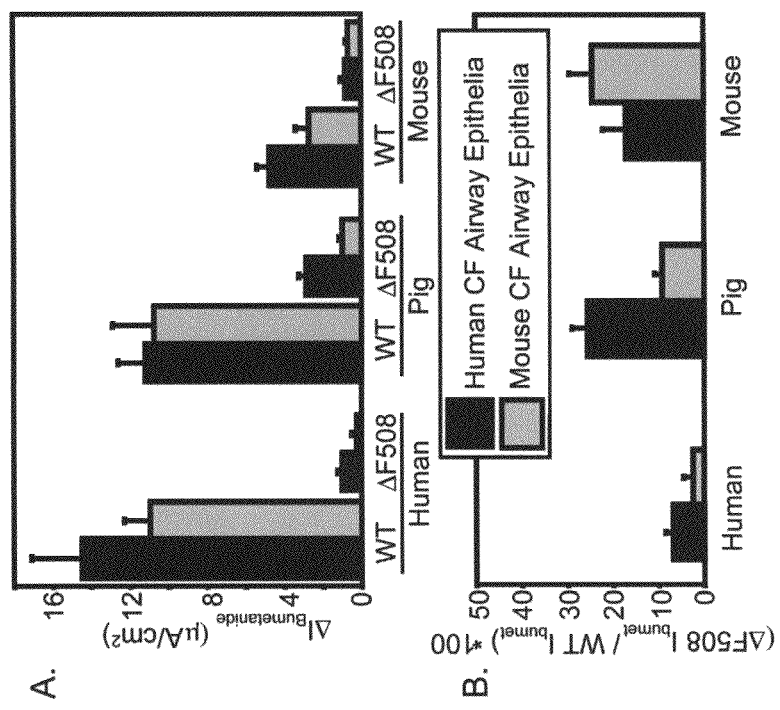
FIG. 23 shows the bumetanide-sensitive cAMP-stimulated current in differentiated CF airway epithelia. A. Currents in human and mouse airway epithelia expressing human, pig, and mouse wild-type CFTR and CFTR-ΔF508 CFTR after subtraction of currents from GFP-expressing control epithelia. B. Bumetanide-inhibited current in CF epithelia expressing CFTR-ΔF508 as a percentage of bumentanide-inhibited current in CF epithelia expressing wild-type CFTR of each species.

Expressing wild-type human CFTR produced significant transepithelial Cl⁻ current (FIGS. 22 and 23), as previously described. The same was true for wild-type pig and mouse CFTR. As expected, human CFTR-ΔF508 failed to generate much current. However, relative to the wild-type current of each species, both pig and mouse CFTR-ΔF508 produced substantial transepithelial Cl⁻ currents (FIG. 23B). To determine if these results were limited to expression in human epithelia, we repeated the study using airway epithelia derived from CF mice; the results were qualitatively similar (FIGS. 23A and 23B). Thus, pig and mouse CFTR-ΔF508 generated transepithelial Cl⁻ currents in CF airway epithelia from two different species. These results indicate that some pig and mouse CFTR-ΔF508 was present and active in the apical membrane of airway epithelia.

IV. A Transgenic, Non-Human Animal Model of Cystic Fibrosis Using Transgenic Human CFTR-ΔF508

The above-mentioned defects between mutant mouse, pig, and human CFTR illustrate the need for the generation of a transgenic non-human animal model of CF that contains a CFTR-ΔΔF508 mutation that closely mimics the functional and processing characteristics of the human CFTR-ΔF508. The generation of a large animal, such as a pig, in which the endogenous CFTR gene is knocked-out and a human CFTR-ΔF508 transgene is introduced allows for the study of the causative factor of human CF without suffering from experimental artifacts introduced by the different physical and functional characteristics of the endogenous CFTR of the animal. Such models also facilitate the identification, characterization, and development of approaches (e.g., small molecule-based drugs) that can be used in CF therapy.

Generation of a CFTR−/− Knock-Out, Human CFTR (hCFTR) Transgenic Pig

A yeast artificial chromosome (YAC) containing the entire ~230 kb human CFTR gene (wild-type or F508del) plus upstream and downstream sequences is introduced into pig CFTR−/− fetal fibroblasts. One specific example is YAC37AB12 (Anand et al., Genomics 9(1):124-130, 1991). This YAC has been used to complement null CF mice (Manson et al., EMBO 16(14):4238-4249, 1997) and to express human CFTR in Chinese hamster ovary cells (Mogayzel et al., Human Molecular Genetics 6(1):59-68, 1997). Any mutations, such as the CF F508del mutation, are introduced into the YAC by site-directed techniques that are well known in the art. YAC delivery is accomplished, for example, via nuclear microinjection, lipid-mediated transfection, or fusion of fibroblasts with yeast spheroplasts. Since the human CFTR-expressing YAC contains an antibiotic selection marker (different from the marker used to make the CFTR−/− cells), cells positive for YAC transgenesis are screened by antibiotic selection. Resistant cells are then screened by PCR, Southern blot, fluorescence in situ hybridization (FISH), and/or fiber-FISH to assess human CFTR integration, copy number, and integrity. These procedures are optimized to minimize the number of fibroblast doublings and time in culture. Cells deemed appropriate for nuclear transfer are then transferred to enucleated oocytes, fused, and electrically stimulated, and transferred to recipient females.

Alternatives to the YAC approach include the use of a minigene, which is a DNA sequence containing the human CFTR promoter and the entire cDNA (CDS and 5' and 3' UTRs) with the first one, two, or three introns still intact. This approach results in human CFTR that still has normal endogenous levels of expression without the large size of the entire gene (<40 kb vs. >300 kb). Additionally, human CFTR cDNA is introduced (i.e., no introns) with either a CFTR promoter, a promoter with CFTR-like tissue expression (e.g., cytokeratin 18 promoter), or a constitutive promoter such as the CMV promoter. In another alternative, the human CFTR and necessary regulation, selection, and tracking elements (e.g., promoter, antibiotic resistance gene, GFP, luciferase) are introduced into a pig fibroblast or fertilized embryo by means of a viral vector, such as a retrovirus or lentivirus. Each of these methods results in the random integration of the wild-type or mutated human CFTR gene in the pig genome, the exact location of which can be later identified.

OTHER EMBODIMENTS

All publications, patents, and other citations noted in this specification are incorporated herein by reference as if each individual publication, patent, or other citation were specifically and individually indicated to be incorporated by reference. Although the invention has been described above in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Use in the claims and elsewhere herein of singular forms, such as "a" and "the," does not exclude indication of the corresponding plural form, unless the context indicates to the contrary. Thus, for example, if a claim indicates the presence of "a" mutation in "a" gene, it can be interpreted as covering one or more mutations, in one or more genes, unless otherwise indicated. Further, the term "or" as used herein is intended to be interpreted as both optional (i.e., one or the other and not both of multiple options) and inclusive (i.e., and/or).

Other embodiments are within the following claims.

What is claimed is:

1. A transgenic pig whose genome comprises a homozygous disruption of a cystic fibrosis membrane transporter (CFTR) gene, wherein the pig does not express functional CFTR, and wherein the pig has a symptom of cystic fibrosis in its pancreas, intestine, liver, or gallbladder.

2. The transgenic pig of claim 1, wherein the disruption comprises an insertion of an exogenous nucleic acid molecule and/or a transcription termination sequence.

3. A cell isolated from the transgenic pig of claim 1.

4. A method of making the transgenic pig of claim 1 comprising:
   i) disrupting a CFTR gene in a fetal pig fibroblast;
   ii) introducing the nucleus of the fetal pig fibroblast into an enucleated pig oocyte to generate a pig embryo;
   iii) transferring the pig embryo into a recipient female such that a transgenic pig whose genome comprises a heterozygous disruption of the CFTR gene is obtained; and
   iv) breeding the pig obtained in iii) such that the transgenic pig of claim 1 is obtained.

5. The transgenic pig of claim 1, wherein the pig has a symptom of cystic fibrosis in its pancreas.

6. The transgenic pig of claim 5, wherein the pig has a symptom of cystic fibrosis in its pancreas comprising exocrine pancreatic insufficiency.

7. The transgenic pig of claim 1, wherein the pig has a symptom of cystic fibrosis in its intestine.

8. The transgenic pig of claim 7, wherein the pig has a symptom of cystic fibrosis in its intestine comprising meconium ileus or intestinal obstruction.

9. The transgenic pig of claim 1, wherein the pig has a symptom of cystic fibrosis in its liver.

10. The transgenic pig of claim 9, wherein the pig has a symptom of cystic fibrosis in its liver comprising focal biliary cirrhosis.

11. The transgenic pig of claim 1, wherein the pig has a symptom of cystic fibrosis in its gallbladder.

\* \* \* \* \*

UNITED STATES PATENT AND TRADEMARK OFFICE
CERTIFICATE OF CORRECTION

PATENT NO. : 8,618,352 B2  
APPLICATION NO. : 12/283980  
DATED : December 31, 2013  
INVENTOR(S) : Michael J. Welsh et al.

It is certified that error appears in the above-identified patent and that said Letters Patent is hereby corrected as shown below:

In the Specification

Please replace the paragraph under STATEMENT AS TO FEDERALLY SPONSORED RESEARCH, at column 1, lines 18-22, with the following:

--This invention was made with government support under grant number HL51670 and grant number DK547759 awarded by National Institutes of Health. The Government has certain rights in the invention.--

Signed and Sealed this  
Twenty-ninth Day of July, 2014

Michelle K. Lee  
*Deputy Director of the United States Patent and Trademark Office*

```
SEQUENCE LISTING

<160> NUMBER OF SEQ ID NOS: 42

<210> SEQ ID NO 1
<211> LENGTH: 6132
<212> TYPE: DNA
<213> ORGANISM: Homo sapiens

<400> SEQUENCE: 1
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga ccatgcagag gtcgcctctg gaaaaggcca gcgttgtctc caaacttttt     180
ttcagctgga ccagaccaat tttgaggaaa ggatacagac agcgcctgga attgtcagac     240 ataccaaa tcccttctgt tgattctgct gacaatctat ctgaaaaatt ggaaagagaa      300
tgggatagag agctggcttc aaagaaaaat cctaaactca ttaatgccct tcggcgatgt     360 ttttctgga gatttatgtt ctatggaatc tttttatatt tagggggaagt caccaaagca     420 gtacagcctc tcttactggg aagaatcata gcttcctatg acccggataa caaggaggaa     480
cgctctatcg cgatttatct aggcataggc ttatgccttc tctttattgt gaggacactg     540
ctcctacacc cagccatttt tggccttcat cacattggaa tgcagatgag aatagctatg     600
tttagtttga tttataagaa gactttaaag ctgtcaagcc gtgttctaga taaaataagt     660
attggacaac ttgttagtct cctttccaac aacctgaaca aatttgatga aggacttgca     720
ttggcacatt tcgtgtggat cgctcctttg caagtggcac tcctcatggg gctaatctgg     780
gagttgttac aggcgtctgc cttctgtgga cttggtttcc tgatagtcct tgcccttttt     840
caggctgggc tagggagaat gatgatgaag tacagagatc agagagctgg gaagatcagt     900
gaaagacttg tgattacctc agaaatgatt gaaaatatcc aatctgttaa ggcatactgc     960
tgggaagaag caatggaaaa aatgattgaa aacttaagac aaacagaact gaaactgact    1020
cggaaggcag cctatgtgag atacttcaat agctcagcct tcttcttctc agggttcttt    1080
gtggtgtttt tatctgtgct tcccctatgca ctaatcaaag gaatcatcct ccggaaaata    1140
ttcaccacca tctcattctg cattgttctg cgcatggcgg tcactcggca atttcccctgg    1200 gctgtacaaa catggtatga ctctcttgga gcaataaaca aaatacagga tttcttacaa    1260
aagcaagaat ataagacatt ggaatataac ttaacgacta cagaagtagt gatggagaat    1320
gtaacagcct tctgggagga gggatttggg gaattatttg agaaagcaaa acaaaacaat    1380
```

```
aacaatagaa aaacttctaa tggtgatgac agcctcttct tcagtaattt ctcacttctt    1440
ggtactcctg tcctgaaaga tattaatttc aagatagaaa gaggacagtt gttggcggtt    1500
gctggatcca ctggagcagg caagacttca cttctaatgg tgattatggg agaactggag    1560
ccttcagagg gtaaaattaa gcacagtgga agaatttcat tctgttctca gttttcctgg    1620
attatgcctg gcaccattaa agaaaatatc atctttggtg tttcctatga tgaatataga    1680
tacagaagcg tcatcaaagc atgccaacta gaagaggaca tctccaagtt tgcagagaaa    1740
gacaatatag ttcttggaga aggtggaatc acactgagtg gaggtcaacg agcaagaatt    1800
tctttagcaa gagcagtata caaagatgct gatttgtatt tattagactc ccttttggga    1860
tacctagatg ttttaacaga aaaagaaata tttgaaagct gtgtctgtaa actgatggct    1920
aacaaaacta ggattttggt cacttctaaa atggaacatt taaagaaagc tgacaaaata    1980
ttaattttgc atgaaggtag cagctatttt tatgggacat tttcagaact ccaaaatcta    2040
cagccagact ttagctcaaa actcatggga tgtgattctt tcgaccaatt tagtgcagaa    2100
agaagaaatt caatcctaac tgagacctta caccgtttct cattagaagg agatgctcct    2160
gtctcctgga cagaaacaaa aaacaatct tttaaacaga ctggagagtt tggggaaaaa    2220
aggaagaatt ctattctcaa tccaatcaac tctatacgaa aattttccat tgtgcaaaag    2280 actccttac aaatgaatgg catcgaagag gattctgatg agcctttaga gagaaggctg    2340
tccttagtac cagattctga gcagggagag gcgatactgc ctcgcatcag cgtgatcagc    2400
actggcccca cgcttcaggc acgaaggagg cagtctgtcc tgaacctgat gacacactca    2460
gttaaccaag gtcagaacat tcaccgaaag acaacagcat ccacacgaaa agtgtcactg    2520
gcccctcagg caaacttgac tgaactggat atatattcaa gaaggttatc tcaagaaact    2580
ggcttggaaa taagtgaaga aattaacgaa gaagacttaa aggagtgctt ttttgatgat    2640
atggagagca taccagcagt gactacatgg aacacatacc ttcgatatat tactgtccac    2700
aagagcttaa ttttttgtgct aatttggtgc ttagtaattt ttctggcaga ggtggctgct    2760
tctttggttg tgctgtggct ccttggaaac actcctcttc aagacaaagg gaatagtact    2820
catagtagaa ataacagcta tgcagtgatt atcaccagca ccagttcgta ttatgtgttt    2880
tacatttacg tgggagtagc cgacactttg cttgctatgg gattcttcag aggtctacca    2940
ctggtgcata ctctaatcac agtgtcgaaa atttttacacc acaaaatgtt acattctgtt    3000
cttcaagcac ctatgtcaac cctcaacacg ttgaaagcag gtgggattct taatagattc    3060
tccaaagata tagcaatttt ggatgacctt ctgcctctta ccatatttga cttcatccag    3120
ttgttattaa ttgtgattgg agctatagca gttgtcgcag ttttacaacc ctacatcttt    3180
gttgcaacag tgccagtgat agtggctttt attatgttga gcatatttt cctccaaacc    3240 tcacagcaac tcaaacaact ggaatctgaa ggcaggagtc aatttttcac tcatcttgtt    3300
acaagcttaa aaggactatg gacacttcgt gccttcggac ggcagcctta ctttgaaact    3360
ctgttccaca aagctctgaa tttacatact gccaactggt tcttgtacct gtcaacactg    3420
cgctggttcc aaatgagaat agaaatgatt tttgtcatct tcttcattgc tgttaccttc    3480
atttccattt taacaacagg agaaggagaa ggaagagttg gtattatcct gacttagcc    3540 atgaatatca tgagtacatt gcagtgggct gtaaactcca gcatagatgt ggatagcttg    3600
atgcgatctg tgagccgagt cttttaagttc attgacatgc aacagaagg taaacctacc    3660 aagtcaacca aaccatacaa gaatggccaa ctctcgaaag ttatgattat tgagaattca    3720
cacgtgaaga aagatgacat ctggcctca ggggggccaaa tgactgtcaa agatctcaca    3780
```

```
gcaaaataca cagaaggtgg aaatgccata ttagagaaca tttccttctc aataagtcct    3840
ggccagaggg tgggcctctt gggaagaact ggatcaggga agagtacttt gttatcagct    3900
tttttgagac tactgaacac tgaaggagaa atccagatcg atggtgtgtc ttgggattca    3960
ataactttgc aacagtggag gaaagccttt ggagtgatac cacagaaagt atttatttttt   4020 tctggaacat ttagaaaaaa cttggatccc tatgaacagt ggagtgatca agaaatatgg    4080
aaagttgcag atgaggttgg gctcagatct gtgatagaac agtttcctgg gaagcttgac    4140
tttgtccttg tggatggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctgaaat gccaacaatt tttggtcata    4380
gaagagaaca aagtgcggca gtacgattcc atccagaaac tgctgaacga gaggagcctc    4440
ttccggcaag ccatcagccc ctccgacagg gtgaagctct tcccaccg gaactcaagc      4500 aagtgcaagt ctaagcccca gattgctgct ctgaaagagg agacagaaga agaggtgcaa    4560
gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt ttttttttaa aaagaaaca tttggtaagg ggaattgagg     4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccctt   4860 gccatgtgct agtaattgga aaggcagctc taaatgtcaa tcagcctagt tgatcagctt    4920
attgtctagt gaaactcgtt aatttgtagt gttggagaag aactgaaatc atacttctta    4980
gggttatgat taagtaatga taactggaaa cttcagcggt ttatataagc ttgtattcct    5040 tttttctctcc tctccccatg atgtttagaa acacaactat attgtttgct aagcattcca   5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
aagaagttga tatgcctttt cccaactcca gaaagtgaca agctcacaga cctttgaact    5400
agagtttagc tggaaaagta tgttagtgca aattgtcaca ggacagccct tctttccaca    5460
gaagctccag gtagagggtg tgtaagtaga taggccatgg gcactgtggg tagacacaca    5520
tgaagtccaa gcatttagat gtataggttg atggtggtat gttttcaggc tagatgtatg    5580
tacttcatgc tgtctacact aagagagaat gagagacaca ctgaagaagc accaatcatg    5640
aattagtttt atatgcttct gttttataat tttgtgaagc aaaattttttt ctctaggaaa   5700 tatttattttt aataatgttt caaacatata taacaatgct gtattttaaa agaatgatta   5760
tgaattacat ttgtataaaa taattttttat atttgaaata ttgactttttt atggcactag  5820 tatttctatg aaatattatg ttaaaactgg gacaggggag aacctagggt gatattaacc    5880
aggggccatg aatcaccttt tggtctggag ggaagccttg gggctgatgc agttgttgcc    5940
cacagctgta tgattcccag ccagcacagc ctcttagatg cagttctgaa gaagatggta    6000
ccaccagtct gactgtttcc atcaagggta cactgccttc tcaactccaa actgactctt    6060
aagaagactg cattatattt attactgtaa gaaaatatca cttgtcaata aaatccatac    6120
atttgtgtga aa                                                       6132
```

```
<210> SEQ ID NO 2
<211> LENGTH: 1480
<212> TYPE: PRT
<213> ORGANISM: Homo sapiens

<400> SEQUENCE: 2

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380
```

```
Tyr Asn Leu Thr Thr Thr Glu Val Val Met Glu Asn Val Thr Ala Phe
385                 390                 395                 400

Trp Glu Glu Gly Phe Gly Leu Phe Glu Lys Ala Lys Gln Asn Asn
            405                 410                 415

Asn Asn Arg Lys Thr Ser Asn Gly Asp Asp Ser Leu Phe Phe Ser Asn
        420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
        450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
                515                 520                 525

Asp Ile Ser Lys Phe Ala Glu Lys Asp Asn Ile Val Leu Gly Glu Gly
        530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu Asn Glu Gly Ser Ser
        610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
            645                 650                 655

Arg Arg Asn Ser Ile Leu Thr Glu Thr Leu His Arg Phe Ser Leu Glu
        660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
        690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
            725                 730                 735

Ser Leu Val Pro Asp Ser Glu Gln Gly Glu Ala Ile Leu Pro Arg Ile
        740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
            805                 810                 815
```

```
Gly Leu Glu Ile Ser Glu Glu Ile Asn Glu Glu Asp Leu Lys Glu Cys
            820                 825                 830

Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
            850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile
        1010                1015                1020

Val Ala Phe Ile Met Leu Arg Ala Tyr Phe Leu Gln Thr Ser Gln
        1025                1030                1035

Gln Leu Lys Gln Leu Glu Ser Glu Gly Arg Ser Pro Ile Phe Thr
        1040                1045                1050

His Leu Val Thr Ser Leu Lys Gly Leu Trp Thr Leu Arg Ala Phe
        1055                1060                1065

Gly Arg Gln Pro Tyr Phe Glu Thr Leu Phe His Lys Ala Leu Asn
        1070                1075                1080

Leu His Thr Ala Asn Trp Phe Leu Tyr Leu Ser Thr Leu Arg Trp
        1085                1090                1095

Phe Gln Met Arg Ile Glu Met Ile Phe Val Ile Phe Phe Ile Ala
        1100                1105                1110

Val Thr Phe Ile Ser Ile Leu Thr Thr Gly Glu Gly Glu Gly Arg
        1115                1120                1125

Val Gly Ile Ile Leu Thr Leu Ala Met Asn Ile Met Ser Thr Leu
        1130                1135                1140

Gln Trp Ala Val Asn Ser Ser Ile Asp Val Asp Ser Leu Met Arg
        1145                1150                1155

Ser Val Ser Arg Val Phe Lys Phe Ile Asp Met Pro Thr Glu Gly
        1160                1165                1170

Lys Pro Thr Lys Ser Thr Lys Pro Tyr Lys Asn Gly Gln Leu Ser
        1175                1180                1185

Lys Val Met Ile Ile Glu Asn Ser His Val Lys Lys Asp Asp Ile
        1190                1195                1200

Trp Pro Ser Gly Gly Gln Met Thr Val Lys Asp Leu Thr Ala Lys
        1205                1210                1215

Tyr Thr Glu Gly Gly Asn Ala Ile Leu Glu Asn Ile Ser Phe Ser
```

```
              1220                 1225                 1230
Ile Ser  Pro Gly Gln Arg  Val Gly Leu Leu  Gly Arg Thr Gly  Ser
    1235                 1240                 1245

Gly Lys  Ser Thr Leu Leu  Ser Ala Phe Leu  Arg Leu Leu Asn  Thr
    1250                 1255                 1260

Glu Gly  Glu Ile Gln Ile  Asp Gly Val Ser  Trp Asp Ser Ile  Thr
    1265                 1270                 1275

Leu Gln  Gln Trp Arg Lys  Ala Phe Gly Val  Ile Pro Gln Lys  Val
    1280                 1285                 1290

Phe Ile  Phe Ser Gly Thr  Phe Arg Lys Asn  Leu Asp Pro Tyr  Glu
    1295                 1300                 1305

Gln Trp  Ser Asp Gln Glu  Ile Trp Lys Val  Ala Asp Glu Val  Gly
    1310                 1315                 1320

Leu Arg  Ser Val Ile Glu  Gln Phe Pro Gly  Lys Leu Asp Phe  Val
    1325                 1330                 1335

Leu Val  Asp Gly Gly Cys  Val Leu Ser His  Gly His Lys Gln  Leu
    1340                 1345                 1350

Met Cys  Leu Ala Arg Ser  Val Leu Ser Lys  Ala Lys Ile Leu  Leu
    1355                 1360                 1365

Leu Asp  Glu Pro Ser Ala  His Leu Asp Pro  Val Thr Tyr Gln  Ile
    1370                 1375                 1380

Ile Arg  Arg Thr Leu Lys  Gln Ala Phe Ala  Asp Cys Thr Val  Ile
    1385                 1390                 1395

Leu Cys  Glu His Arg Ile  Glu Ala Met Leu  Glu Cys Gln Gln  Phe
    1400                 1405                 1410

Leu Val  Ile Glu Glu Asn  Lys Val Arg Gln  Tyr Asp Ser Ile  Gln
    1415                 1420                 1425

Lys Leu  Leu Asn Glu Arg  Ser Leu Phe Arg  Gln Ala Ile Ser  Pro
    1430                 1435                 1440

Ser Asp  Arg Val Lys Leu  Phe Pro His Arg  Asn Ser Ser Lys  Cys
    1445                 1450                 1455

Lys Ser  Lys Pro Gln Ile  Ala Ala Leu Lys  Glu Glu Thr Glu  Glu
    1460                 1465                 1470

Glu Val  Gln Asp Thr Arg  Leu
    1475                 1480

<210> SEQ ID NO 3
<211> LENGTH: 6299
<212> TYPE: DNA
<213> ORGANISM: Mus musculus

<400> SEQUENCE: 3
aattggaagc aaatgacatc acctcaggtc tgagtaaaag ggacgagcca aaagcattga      60
cctggtcctg gatatccaga tgtcgagtcc aacctgaatt tagccgaaca cagacctcat     120
tgctcacgga gacatcatgc agaagtcgcc tttggagaaa gccagcttta tctccaaact     180
cttcttcagc tggaccacac caattttgag gaaagggtac agacaccact tggagttgtc     240
agacatatac caagccccct tctgctgatt cagctgacca cttgtctgaa aactagaaag     300
agaatgggac agagaacaag cttcaaaaaa gaatccccag cttatccacg cccttcggcg     360
atgctttttc tggagattcc tcttctatgg aattttgcta tacctagggg aagtcaccaa     420
ggctgtccag cctgtcttgc taggaagaat catagcatcc tatgatccag aaaacaaggt     480
ggaacgttcc attgccattt accttggcat aggcttatgc cttctcttca ttgtcaggac     540
actgcttctt cacccagcta ttttttggcct tcatcgcatt ggaatgcaga tgagaacagc     600
```

```
tatgtttagc ttgatttata agaagacttt aaagttgtca agccgcgttc ttgataaaat    660
aagtattgga caacttgtta gtcttctttc caacaacctg aacaaatttg atgaaggact    720
tgccttggca cattttatat ggattgctcc tttacaagtg actcttctga tggggcttct    780
ctgggacttg ttacagttct cagccttctg tggccttggt ttactgataa tcctggttat    840
ttttcaagct atcctaggga agatgatggt gaagtacaga gatcaaagag ctgcaaagat    900
caatgaaaga ctcgtgatca catcagaaat tattgataat atctattctg ttaaggcata    960 ttgtgggaa tcagcgatgg agaaaatgat tgaaaacttg agagaggtgg agctgaaaat     1020
gacccggaag gcggcctata tgaggttctt cactagctct gccttcttct tttcagggtt    1080
ctttgtagtc tttctatctg tgcttcccta cacagtcatc aacggaatcg tcctacgaaa    1140
aatattcaca accatttcat tctgcattgt cctacgtatg tcagtcacgc ggcagttccc    1200
cactgccgta cagatatggt atgattcttt tggaatgata agaaaaatac aggatttcct    1260
gcagaaacaa gagtataaag tactggagta taacttaatg accacaggca taatcatgga    1320
aaatgtaaca gcattttggg aggagggatt tggggaatta ctgcagaaag cacaacaaag    1380
caatggtgac agaaaacatt ccagtgatga gaacaatgtc agtttcagtc atctctgcct    1440
tgtgggaaat cctgtgctga aaaacatcaa tttgaatata gagaaggag atgttggc      1500 tattactgga tctactggac taggaaagac atcactcctg atgttgattt gggagaact    1560 ggaagcttca gagggaatta ttaagcacag tggaagagtt tcattctgct ctcaattttc    1620
ttggattatg ccgggtacta tcaaagaaaa tatcatcttt ggtgtttcct atgatgagta    1680
cagatataag agtgttgtca aagcttgcca actacagcag gacatcacca gtttgcaga    1740 acaagacaac acagttcttg gagaaggtgg agtcacactg agtggaggtc agcgtgcaag    1800 gatttctta gcaagagcag tatataaaga tgctgatttg tacctattag attccccttt    1860
tggatatcta gatgttttta ctgaagaaca agtatttgaa agctgtgttt gtaaattgat    1920
ggccaacaaa actaggattt tggttacatc taaaatggaa cacttaagga aagctgacaa    1980
aatactaatt ttgcatcagg ggactagcta tttttatggg acatttctg agctacaaag    2040 tctacgtccg agcttcagtt cgaaactcat ggggtatgat actttgacc agtttactga    2100 ggaaagaaga agttcaattc taactgagac cttacgcagg ttctcagtag acgattcctc    2160
tgccccgtgg agcaaaccca acagtcgtt tagacagact ggagaggtgg gagaaaaag    2220 gaagaactct attctaaatt cattcagctc tgtaaggaaa atttccattg tgcaaaagac    2280
tccattatgt atcgatggag agtctgatga tctccaagaa aagagactgt ccctagttcc    2340
ggattctgaa caggggagg ctgctctgcc gcgcagcaac atgatcgcca ccggccccac    2400
atttccaggc agaagaagac agtctgtttt ggatctgatg acgttcacac ccaactcagg    2460
ctccagcaat cttcagagga ccagaacttc tattcgaaaa atctccttag tccctcagat    2520
aagcttaaat gaagtggatg tatattcaag gagattatcg caagatagca cactgaacat    2580
cactgaagaa attaacgaag aagatttaaa ggagtgtttt cttgatgatg tgatcaagat    2640 accccggtg acaacatgga acacatacct acgatatttt actctccata aaggcttact    2700
gctagtgctg atttggtgcg tactggtttt tctggttgag gtggctgctt ctttatttgt    2760
gttatggttg cttaaaaaca accctgttaa cagtggaaac aatggtacta aaatttccaa    2820
tagctcctac gttgtgatca tcaccagtac cagtttctat tatatttttt acatttacgt    2880
gggagtggct gacactttgc ttgccctgag cctcttcaga ggtttgccgc tggtgcatac    2940
gttaatcaca gcatcaaaaa ttttgcacag gaaaatgtta cactccattc ttcacgcccc    3000
```

```
tatgtcgacc atcagcaagc tgaaagcagg tgggattctt aacagattct ccaaagatat    3060
agcaattttg gatgactttc tgcctcttac catttttgac ttcattcagt tggtgttcat    3120
tgtgattgga gctataatag tcgtctcggc attacaaccc tacatcttcc tagcaacggt    3180
gccagggcta gtagtcttta ttttactgag ggcctacttc cttcatacag cacagcagct    3240
caaacaactg gaatctgaag gcaggagtcc aattttcacc caccttgtga caagcttaaa    3300
aggactctgg acacttcgag ccttccgacg ccagacttac tttgaaactc tgttccacaa    3360
agctctgaat ttgcacactg ccaactggtt tatgtatctg caaccttgc gctggttcca    3420 aatgagaata gacatgatat ttgtcctctt cttcattgtt gttaccttca tctccatttt    3480
aacaacaggt gaaggagaag gaacagctgg tattattcta actttagcta tgaatatcat    3540
gagtactttg cagtgggctg tgaactcaag cattgataca gatagcttga tgcgatctgt    3600
gagcagagtg tttaagttta ttgatataca aacagaagaa agtatgtaca cacagataat    3660
taaagaacta cctagagaag gatcatctga cgttttagtc attaagaatg agcatgtgaa    3720
gaaaagtgat atctggccct ctggaggcga atggttgtc aaagaccttga ctgtgaaata    3780 catggatgat ggaaatgccg tattagagaa catttctttt tcaataagtc ctggacagag    3840
ggtggggctc ttaggaagaa ctggatcagg aaaaagtact ttgctttcag cattttttacg    3900 aatgttgaac attaaaggtg atatagagat tgatggtgtc tcatggaatt cagtgacctt    3960
acaagaatgg aggaaagctt tcggagtgat aacacagaaa gtatttatct tttctggaac    4020
attcagacaa aacctggatc ccaatggaaa atggaaagat gaagaaatat ggaaagttgc    4080
agatgaggtt ggactcaagt ctgtaataga gcagtttcct ggacagctca actttaccct    4140
tgtggatggg ggttatgtgc taagccatgg ccataagcaa ttaatgtgct ggcccgatc    4200 agttctcagt aaggccaaga tcatactgct tgatgagccc agtgcccatc tagaccccat    4260
aacataccaa gtcattcgac gagttctaaa acaagcctttc gctggttgca cagtcatcct    4320
ctgtgaacac aggatagaag cgatgttgga ttgccagcga ttttttggtca tagaagagag    4380 caatgtctgg cagtacgact ccccttcaggc acttctgagt gagaagagta tcttccagca    4440
ggccattagc tcctcggaaa agatgaggtt cttccagggc cgccactcca gcaagcacaa    4500
gcctcggacg caaattactg ctctgaaaga ggagacagaa gaagaagttc aagaaacccg    4560
tctctagtgc tgggatgctg aggaagcaac tcagtgcgca ctgagtccat tcccagaacc    4620
catgcagaat gaaaaaagcc aggcatttcc catgcttcta acccagtgc tgggacacag    4680 agacaggtgg atccctgggg ctctgtggca agtgatccta gcccacaaag agagttccag    4740
gctgggcacc tgagggacaa tacctgtgga tatactcttg cttccacatg caagtacata    4800
tacacatgca tgcacattag tggacataca cacagaaaag caaagaagaa ggaaagaggg    4860
aagaaaatag tgcaaataat tgcaaaacga tcatgtatgg agtctgctca tggacttaga    4920
ggaggtgaac tctactacct gtgcctttga agggtgaagc ctgcgacttg ctctttaaga    4980
gactgttttg gaagagagtt caaaaacgtt catatgggta tgggtaactg actttccagc    5040
agtagtcaaa ttgtttgaac ttcagatagt tgataatgac cacttgtgta ttgcaaggca    5100 gattttttctg aaaacatttg cccccctaata gtagctgaaa aagcagctat aaatgccaac    5160
caggttagtc attcggctta ttgttcagta cagctggtta atttgcatta ttgaagaact    5220
gaaattatag tgcttagata tagaacaaag taaagagaac taaaaacagt gtcttatata    5280
actcaaagcc caacttactt tcctctaaga tatgtattgc cttctataca ttttctgccc    5340
cattccaagc aaatgttaga atattataca aaatactggg tggtattgat tgaaagatgc    5400
```

-continued

```
ccgacatctg gtgatctagt aacccatcag gattaaggat atccaggtct tggaaattaa    5460
ggttaagacc atctagcctt actaccgtac agctaaacat tcttattacc agaataagac    5520
ctaggaaaaa gaactgtttc agtcccataa agtggcctgg ataatttcct tgatatggaa    5580
atcgacacac ttatgttccc agaaagcaac agatctttaa gacttctgaa gtgaaggaag    5640
gttgtgttag tgcaaactag tgcagcccag tgccaggtcc aggagttaac atgtagacag    5700
gccatggact gtgtgggtag atgctcatgg aaatgtgcag tagtatgttc atgtgctctc    5760
agctagctgt gtgtacttca aactgtctcc acagagttgt tggggagaca ctctgaaaaa    5820
gaattaattg tgaattagtt ttatatactt tgttttataa tttgtgatgc aaatgaaaat    5880
ttctctggga aatatttatt ttagtaataa tgtttcaaac tatatataac aatgctgtat    5940
tttaagaatg attacataat gacttatatt tgtataaaat aatttttata tttgaaatgt    6000
taacttttta tagcactagc tattttaaaa caggggagtg aggaggacag ggatgataag    6060
gatcattcaa cttcatgttg tgaagacgag ctgatgtaaa tcttgtaccc atctgtgtgg    6120
ttctcagaca acacatgctc tcttttaatg cagctttgaa gaagatggta ccaaaggtta    6180
agacggcccc ctgatgggca catcaacttc tgaactgcaa actaagcttt agaggaatgt    6240
attatattta ttactgtaat agaatatcat gtgtcaataa aatccttta tttgtgtga     6299
```

<210> SEQ ID NO 4
<211> LENGTH: 1476
<212> TYPE: PRT
<213> ORGANISM: Mus musculus

<400> SEQUENCE: 4

```
Met Gln Lys Ser Pro Leu Glu Lys Ala Ser Phe Ile Ser Lys Leu Phe
1               5                   10                  15

Phe Ser Trp Thr Thr Pro Ile Leu Arg Lys Gly Tyr Arg His His Leu
            20                  25                  30

Glu Leu Ser Asp Ile Tyr Gln Ala Pro Ser Ala Asp Ser Ala Asp His
        35                  40                  45

Leu Ser Glu Lys Leu Glu Arg Glu Trp Asp Arg Glu Gln Ala Ser Lys
    50                  55                  60

Lys Asn Pro Gln Leu Ile His Ala Leu Arg Arg Cys Phe Phe Trp Arg
65                  70                  75                  80

Phe Leu Phe Tyr Gly Ile Leu Leu Tyr Leu Gly Glu Val Thr Lys Ala
                85                  90                  95

Val Gln Pro Val Leu Leu Gly Arg Ile Ile Ala Ser Tyr Asp Pro Glu
            100                 105                 110

Asn Lys Val Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His Arg Ile Gly Met Gln Met Arg Thr Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Ile Trp Ile Ala Pro Leu Gln Val
        195                 200                 205

Thr Leu Leu Met Gly Leu Leu Trp Asp Leu Leu Gln Phe Ser Ala Phe
    210                 215                 220
```

```
Cys Gly Leu Gly Leu Leu Ile Ile Leu Val Ile Phe Gln Ala Ile Leu
225                 230                 235                 240

Gly Lys Met Met Val Lys Tyr Arg Asp Gln Arg Ala Ala Lys Ile Asn
            245                 250                 255

Glu Arg Leu Val Ile Thr Ser Glu Ile Ile Asp Asn Ile Tyr Ser Val
                260                 265                 270

Lys Ala Tyr Cys Trp Glu Ser Ala Met Glu Lys Met Ile Glu Asn Leu
            275                 280                 285

Arg Glu Val Glu Leu Lys Met Thr Arg Lys Ala Ala Tyr Met Arg Phe
        290                 295                 300

Phe Thr Ser Ser Ala Phe Phe Ser Gly Phe Val Val Phe Leu
305                 310                 315                 320

Ser Val Leu Pro Tyr Thr Val Ile Asn Gly Ile Val Leu Arg Lys Ile
                325                 330                 335

Phe Thr Thr Ile Ser Phe Cys Ile Val Leu Arg Met Ser Val Thr Arg
                340                 345                 350

Gln Phe Pro Thr Ala Val Gln Ile Trp Tyr Asp Ser Phe Gly Met Ile
            355                 360                 365

Arg Lys Ile Gln Asp Phe Leu Gln Lys Gln Glu Tyr Lys Val Leu Glu
        370                 375                 380

Tyr Asn Leu Met Thr Thr Gly Ile Ile Met Glu Asn Val Thr Ala Phe
385                 390                 395                 400

Trp Glu Glu Gly Phe Gly Glu Leu Leu Gln Lys Ala Gln Gln Ser Asn
                405                 410                 415

Gly Asp Arg Lys His Ser Ser Asp Glu Asn Asn Val Ser Phe Ser His
            420                 425                 430

Leu Cys Leu Val Gly Asn Pro Val Leu Lys Asn Ile Asn Leu Asn Ile
        435                 440                 445

Glu Lys Gly Glu Met Leu Ala Ile Thr Gly Ser Thr Gly Leu Gly Lys
450                 455                 460

Thr Ser Leu Leu Met Leu Ile Leu Gly Glu Leu Glu Ala Ser Glu Gly
465                 470                 475                 480

Ile Ile Lys His Ser Gly Arg Val Ser Phe Cys Ser Gln Phe Ser Trp
            485                 490                 495

Ile Met Pro Gly Thr Ile Lys Glu Asn Ile Ile Phe Gly Val Ser Tyr
                500                 505                 510

Asp Glu Tyr Arg Tyr Lys Ser Val Val Lys Ala Cys Gln Leu Gln Gln
            515                 520                 525

Asp Ile Thr Lys Phe Ala Glu Gln Asp Asn Thr Val Leu Gly Glu Gly
        530                 535                 540

Gly Val Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
            565                 570                 575

Tyr Leu Asp Val Phe Thr Glu Glu Gln Val Phe Glu Ser Cys Val Cys
                580                 585                 590

Lys Leu Met Ala Asn Lys Thr Arg Ile Leu Val Thr Ser Lys Met Glu
            595                 600                 605

His Leu Arg Lys Ala Asp Lys Ile Leu Ile Leu His Gln Gly Thr Ser
        610                 615                 620

Tyr Phe Tyr Gly Thr Phe Ser Glu Leu Gln Ser Leu Arg Pro Ser Phe
625                 630                 635                 640

Ser Ser Lys Leu Met Gly Tyr Asp Thr Phe Asp Gln Phe Thr Glu Glu
```

-continued

```
                645                 650                 655
Arg Arg Ser Ser Ile Leu Thr Glu Thr Leu Arg Arg Phe Ser Val Asp
            660                 665                 670

Asp Ser Ser Ala Pro Trp Ser Lys Pro Lys Gln Ser Phe Arg Gln Thr
            675                 680                 685

Gly Glu Val Gly Glu Lys Arg Lys Asn Ser Ile Leu Asn Ser Phe Ser
            690                 695                 700

Ser Val Arg Lys Ile Ser Ile Val Gln Lys Thr Pro Leu Cys Ile Asp
705                 710                 715                 720

Gly Glu Ser Asp Asp Leu Gln Glu Lys Arg Leu Ser Leu Val Pro Asp
                725                 730                 735

Ser Glu Gln Gly Glu Ala Ala Leu Pro Arg Ser Asn Met Ile Ala Thr
                740                 745                 750

Gly Pro Thr Phe Pro Gly Arg Arg Gln Ser Val Leu Asp Leu Met
                755                 760                 765

Thr Phe Thr Pro Asn Ser Gly Ser Ser Asn Leu Gln Arg Thr Arg Thr
            770                 775                 780

Ser Ile Arg Lys Ile Ser Leu Val Pro Gln Ile Ser Leu Asn Glu Val
785                 790                 795                 800

Asp Val Tyr Ser Arg Arg Leu Ser Gln Asp Ser Thr Leu Asn Ile Thr
                805                 810                 815

Glu Glu Ile Asn Glu Glu Asp Leu Lys Glu Cys Phe Leu Asp Asp Val
                820                 825                 830

Ile Lys Ile Pro Pro Val Thr Thr Trp Asn Thr Tyr Leu Arg Tyr Phe
            835                 840                 845

Thr Leu His Lys Gly Leu Leu Leu Val Leu Ile Trp Cys Val Leu Val
            850                 855                 860

Phe Leu Val Glu Val Ala Ala Ser Leu Phe Val Leu Trp Leu Leu Lys
865                 870                 875                 880

Asn Asn Pro Val Asn Ser Gly Asn Asn Gly Thr Lys Ile Ser Asn Ser
                885                 890                 895

Ser Tyr Val Val Ile Ile Thr Ser Thr Ser Phe Tyr Tyr Ile Phe Tyr
            900                 905                 910

Ile Tyr Val Gly Val Ala Asp Thr Leu Leu Ala Leu Ser Leu Phe Arg
            915                 920                 925

Gly Leu Pro Leu Val His Thr Leu Ile Thr Ala Ser Lys Ile Leu His
            930                 935                 940

Arg Lys Met Leu His Ser Ile Leu His Ala Pro Met Ser Thr Ile Ser
945                 950                 955                 960

Lys Leu Lys Ala Gly Gly Ile Leu Asn Arg Phe Ser Lys Asp Ile Ala
                965                 970                 975

Ile Leu Asp Asp Phe Leu Pro Leu Thr Ile Phe Asp Phe Ile Gln Leu
            980                 985                 990

Val Phe Ile Val Ile Gly Ala Ile  Ile Val Val Ser Ala  Leu Gln Pro
            995                 1000                1005

Tyr Ile  Phe Leu Ala Thr Val  Pro Gly Leu Val Val  Phe Ile Leu
    1010                1015                1020

Leu Arg  Ala Tyr Phe Leu His  Thr Ala Gln Gln Leu  Lys Gln Leu
    1025                1030                1035

Glu Ser  Glu Gly Arg Ser Pro  Ile Phe Thr His Leu  Val Thr Ser
    1040                1045                1050

Leu Lys  Gly Leu Trp Thr Leu  Arg Ala Phe Arg Arg  Gln Thr Tyr
    1055                1060                1065
```

-continued

Phe Glu Thr Leu Phe His Lys Ala Leu Asn Leu His Thr Ala Asn
1070              1075                  1080

Trp Phe Met Tyr Leu Ala Thr Leu Arg Trp Phe Gln Met Arg Ile
1085              1090                  1095

Asp Met Ile Phe Val Leu Phe Phe Ile Val Val Thr Phe Ile Ser
1100              1105                  1110

Ile Leu Thr Thr Gly Glu Gly Glu Gly Thr Ala Gly Ile Ile Leu
1115              1120                  1125

Thr Leu Ala Met Asn Ile Met Ser Thr Leu Gln Trp Ala Val Asn
1130              1135                  1140

Ser Ser Ile Asp Thr Asp Ser Leu Met Arg Ser Val Ser Arg Val
1145              1150                  1155

Phe Lys Phe Ile Asp Ile Gln Thr Glu Glu Ser Met Tyr Thr Gln
1160              1165                  1170

Ile Ile Lys Glu Leu Pro Arg Glu Gly Ser Ser Asp Val Leu Val
1175              1180                  1185

Ile Lys Asn Glu His Val Lys Lys Ser Asp Ile Trp Pro Ser Gly
1190              1195                  1200

Gly Glu Met Val Val Lys Asp Leu Thr Val Lys Tyr Met Asp Asp
1205              1210                  1215

Gly Asn Ala Val Leu Glu Asn Ile Ser Phe Ser Ile Ser Pro Gly
1220              1225                  1230

Gln Arg Val Gly Leu Leu Gly Arg Thr Gly Ser Gly Lys Ser Thr
1235              1240                  1245

Leu Leu Ser Ala Phe Leu Arg Met Leu Asn Ile Lys Gly Asp Ile
1250              1255                  1260

Glu Ile Asp Gly Val Ser Trp Asn Ser Val Thr Leu Gln Glu Trp
1265              1270                  1275

Arg Lys Ala Phe Gly Val Ile Thr Gln Lys Val Phe Ile Phe Ser
1280              1285                  1290

Gly Thr Phe Arg Gln Asn Leu Asp Pro Asn Gly Lys Trp Lys Asp
1295              1300                  1305

Glu Glu Ile Trp Lys Val Ala Asp Glu Val Gly Leu Lys Ser Val
1310              1315                  1320

Ile Glu Gln Phe Pro Gly Gln Leu Asn Phe Thr Leu Val Asp Gly
1325              1330                  1335

Gly Tyr Val Leu Ser His Gly His Lys Gln Leu Met Cys Leu Ala
1340              1345                  1350

Arg Ser Val Leu Ser Lys Ala Lys Ile Ile Leu Leu Asp Glu Pro
1355              1360                  1365

Ser Ala His Leu Asp Pro Ile Thr Tyr Gln Val Ile Arg Arg Val
1370              1375                  1380

Leu Lys Gln Ala Phe Ala Gly Cys Thr Val Ile Leu Cys Glu His
1385              1390                  1395

Arg Ile Glu Ala Met Leu Asp Cys Gln Arg Phe Leu Val Ile Glu
1400              1405                  1410

Glu Ser Asn Val Trp Gln Tyr Asp Ser Leu Gln Ala Leu Leu Ser
1415              1420                  1425

Glu Lys Ser Ile Phe Gln Gln Ala Ile Ser Ser Ser Glu Lys Met
1430              1435                  1440

Arg Phe Phe Gln Gly Arg His Ser Ser Lys His Lys Pro Arg Thr
1445              1450                  1455

Gln Ile Thr Ala Leu Lys Glu Glu Thr Glu Glu Glu Val Gln Glu
1460              1465                  1470

Thr Arg Leu
   1475

<210> SEQ ID NO 5
<211> LENGTH: 4449
<212> TYPE: DNA
<213> ORGANISM: Sus scrofa

<400> SEQUENCE: 5

| | | | | | |
|---|---|---|---|---|---|
| atgcagaggt | cgcctctgga | aaaggccagc | atcttctcca | aacttttttt | cagctggacc | 60 |
| agaccaattt | tgagaaaagg | atatagacag | cgcctggaat | tgtcagacat | ataccatatc | 120 |
| tcttcttctg | actctgctga | caatctgtct | gaaaaattgg | aaagagaatg | ggacagagaa | 180 |
| ctggcttcaa | agaagaatcc | caaactcatt | aatgcccttc | ggcgatgttt | ttttggaga | 240 |
| tttatgttct | atggaatcat | attatattta | ggggaagtca | ccaaagcagt | ccagcctctc | 300 |
| ttactgggaa | gaatcatagc | ttcctatgat | ccagataaca | aggcggaacg | ctccattgcg | 360 |
| atttacctag | gcgtaggctt | atgtcttctc | ttcatcgtga | ggactctgct | cctgcaccca | 420 |
| gccattttg | ccccccatca | cattggcatg | cagatgagaa | tagctatgtt | tagtttgatt | 480 |
| tacaaaaaga | ctttgaagct | gtcaagccgt | gttctagata | aaataagtat | tggacaactt | 540 |
| gttagtctcc | tttccaacaa | cctgaacaag | tttgatgaag | acttgccctt | ggcgcacttc | 600 |
| gtgtggatcg | ctcctctgca | agtgacgctg | ctgatggggc | tgctgtggga | gttgttgcag | 660 |
| gcctccgcct | tctgtggact | tgccttcctc | gtagtcctcg | ccctctttca | agctgggttg | 720 |
| gggaaaatga | tgatgaagta | cagagatcag | agagctggaa | agatcaatga | aagactggtg | 780 |
| attacctcag | agatgattga | aaatatccaa | tcagttaaag | catactgctg | ggaagaagcg | 840 |
| atggaaaaaa | tgattgaaaa | acctaagaca | acggaactga | aactgacccg | gaaggcagcc | 900 |
| tatgtgagat | acttcaatag | ctcagccttc | ttcttctctg | ggctctttgt | ggtgtttta | 960 |
| tctgtgcttc | cctacgcact | gctcaaagga | atcatgcttc | gaaaaatctt | cacaaccatc | 1020 |
| tcattctgca | ttgttctgcg | catggcagtc | acccggcaat | tccctgggc | tgtacaaact | 1080 |
| tggtatgatt | ctcttggagc | aataaacaaa | atacaggatt | tcttacagaa | gcaagaatat | 1140 |
| aagacactgg | aatacaactt | aacaactaca | gaagtagtga | tggagaatgt | aacagccttc | 1200 |
| tgggaagagg | gatttgggaa | attatttgag | aaagcaaaac | aaaataataa | cagtcgaaaa | 1260 |
| atttccaatg | gtgataacag | cctcttcttc | agtaactttt | cacttctcgg | tactcctgtc | 1320 |
| ctgaaagata | tcagttttca | gatagaaaga | ggacaattgt | tggcagttgc | tggatctact | 1380 |
| ggagcaggca | agacatcact | tctgatgatg | attatgggag | aactggagcc | ttcagagggt | 1440 |
| aaaattaagc | acagtggaag | aatttcattc | tgctctcagt | tttcctggat | catgccgggc | 1500 |
| accattaaag | aaaacatcat | ctttggtgtt | tcctatgatg | agtatagata | caggagtgtc | 1560 |
| atcaaagcgt | gccaactaga | agaggacatc | tccaagtttg | cagagaaaga | caacatagtt | 1620 |
| ctgggagaag | gtggaatcac | actgagtgga | ggtcagcgag | caagaatttc | tttagcaaga | 1680 |
| gcagtatata | agatgctga | tttgtaccta | ttagactctc | cttttggata | cctagatgtt | 1740 |
| ttaacagaga | agaaatatt | tgaaagctgt | gtctgtaaat | tgatggctaa | caaaactagg | 1800 |
| attttggtca | cttctaaaat | ggaacattta | agaaagctg | acaaaatact | aattttacat | 1860 |
| gaaggtagca | gctatttta | tgggacattt | tctgaattac | aaagtcagcg | gcccgacttc | 1920 |
| agttcaaagc | ttatgggata | tgatactttt | gaccaattta | ctgcagaacg | gagaaattca | 1980 |
| atcataactg | agactttacg | gcgtttctca | ttagaaggag | atgcctctgt | gtcctggaac | 2040 |

-continued

```
gaaacaaaaa aacaatcctt taaacagact ggagagtttg gtgaaaaaag gaagaattcc    2100
attctcaatt caatcaactc tataaggaaa ttttcaattg tacaaaagac tcccttacaa    2160
atgaatggct ttgaagaaga ttctggcgag cctttagaga aaggctgtc cttagttcct     2220 gattctgagc atggggaggc aattctacct cggagcaacg tgatcaacgc tggcccacg     2280 tttcagggac gacggaggca gtctgttctg aacctcatga cccgctcctc agtgaaccaa    2340
ggtcaaagca ttcaccgaaa gacagcgacg tccacacgga aaatgtcact ggtccctcaa    2400
gcaaacttaa ctgaaataga tatatattcc agacgattat cgcaagatac tggcttggaa    2460
ataagtgaag aaattaatga agaagattta agggagtgct tttttgatga cgtggagagc    2520
ataccaaccg tgactacctg gaacacatac ctccgatatg ttactgttca caagagctta    2580 attttttgtgc tgatttggtg cttagttgtt tttctggctg aggtggctgc ttgtttggtt   2640
gtgttgtgtt tgcttaaaaa aacatctcct caagacaaag ggaatagcac taagggtgca    2700
aataacagct atgcagtaat catcaccagc accagcgcat actatgtttt ttacatttac    2760
gtgggagtag ccgacggttt gcttgctctg ggactcttca gaggtttacc actggtgcat    2820
actctaatca cagtgtcgaa aattttacat cgcaaaatgt tacactctgt tcttcaagcc    2880
cctatgtcaa ccctcaacac attgaaagca ggtgggattc ttaatagatt ctccaaagat    2940
atagcagttt tggatgatct cctgcctctt actatatttg atttcatcca gttactatta    3000
attgtgattg gagctgtggc agttgtctca gtttttaaaac cttacatctt cctggcaaca    3060
gtgccagtga tagtggcttt tattctactg agagcctact tcctccacac ttcacagcag    3120
ctcaaacagc tggaatctga aggcaggagt ccaatttttca ctcatctcat tacaagctta   3180
aaaggactat ggacccttcg agcctttgga cgtcagcctt actttgaaac tttgttccac    3240
aaagctctta atttacatac tgccaactgg ttcttgtatc tgtcaacact acgctggttc    3300
caaatgcgaa tagaaatgat ttttgtcatc tttttcattg ccgttacctt catttccatt    3360
ttaacaacag gggaaggaga aggaacagtt gggattattc taacattagc catgaatatc    3420
atgagtacat tgcagtgggc tgtaaactcc agtatagatg tggatagctt gatgcgatct    3480
gtgagccgag tctttaagtt tattgatatg ccggcagaag gagatcaacc taacaggtcg    3540
ttcaaaccat ccaaggatgg ccagcttttca aggttatga ttattgagaa tcaacatgtg     3600
aagaaagatg acatctggcc ttcagggggc caaatgactg tcaaagacct cactgcgaaa    3660
tatgtagatg gtgggaacgc cgtattagag aacatttcct tctcaataag tcctggccag    3720
agggtgggcc tcttgggaag aactggatca gggaagagca ctttattatt ggcttttttg     3780
agactgctga acacagaagg agaaatacaa gtagatggtg tgtcttggga ttcaataact    3840
ttgcaacagt ggaggaaagc ttttggagtc atacccaga aagtattcat cttttctgga     3900
acatttagaa aaaacctgga tccctatgga cagtggaatg atcaagaaat atggaaagtt    3960
gcagaggagg ttggactcag atctgtgata gagcagtttc ctgggaagct tgattttgtc    4020
cttgtagatg ggggttgtgt tctaagccac ggccacaagc agttgatgtg cttggccaga    4080
tctgttcttg gtaaagcaaa gatcttgctg ctggatgaac ccagtgctca tttgatccc     4140 ataacgtacc aaatcattcg aagaaccctg aaacaagcat tgctgattg cacagtaatc    4200 ctctctgaac acaggataga agcaatgttg gaatgtcaac gattttttggt catagaggag   4260 aacaaagtgc ggcagtatga ttccatccag aggctgctga gcgagaagag cctcttcagg    4320
caggcgatca gccccttgga ccgcctgaag ctcctcccac accggaactc tagcaagcag    4380
aggtctcggt ccaaaatcgc agctctgaag gaggaaacag aagaagaggt gcaagaaaca    4440
```

-continued

```
agactttag                                                        4449
```

<210> SEQ ID NO 6
<211> LENGTH: 1482
<212> TYPE: PRT
<213> ORGANISM: Sus scrofa

<400> SEQUENCE: 6

```
Met Gln Arg Ser Pro Leu Glu Lys Ala Ser Ile Phe Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr His Ile Ser Ser Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Ile Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Ala Glu Arg Ser Ile Ala Ile Tyr Leu Gly Val Gly Leu Cys
        115                 120                 125

Leu Leu Phe Ile Val Arg Thr Leu Leu Leu His Pro Ala Ile Phe Gly
    130                 135                 140

Pro His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Thr Leu Leu Met Gly Leu Leu Trp Glu Leu Leu Gln Ala Ser Ala Phe
    210                 215                 220

Cys Gly Leu Ala Phe Leu Val Val Leu Ala Leu Phe Gln Ala Gly Leu
225                 230                 235                 240

Gly Lys Met Met Met Lys Tyr Arg Asp Gln Arg Ala Gly Lys Ile Asn
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Leu Phe Val Val Phe Leu
305                 310                 315                 320

Ser Val Leu Pro Tyr Ala Leu Leu Lys Gly Ile Met Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
```

```
            370                 375                 380
Tyr Asn Leu Thr Thr Thr Glu Val Val Met Glu Asn Val Thr Ala Phe
385                 390                 395                 400

Trp Glu Glu Gly Phe Gly Lys Leu Phe Glu Lys Ala Lys Gln Asn Asn
                405                 410                 415

Asn Ser Arg Lys Ile Ser Asn Gly Asp Asn Ser Leu Phe Phe Ser Asn
                420                 425                 430

Phe Ser Leu Leu Gly Thr Pro Val Leu Lys Asp Ile Ser Phe Lys Ile
                435                 440                 445

Glu Arg Gly Gln Leu Leu Ala Val Ala Gly Ser Thr Gly Ala Gly Lys
                450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
                515                 520                 525

Asp Ile Ser Lys Phe Ala Glu Lys Asp Asn Ile Val Leu Gly Glu Gly
                530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
                580                 585                 590

Lys Leu Met Ala Asn Lys Thr Arg Ile Leu Val Thr Ser Lys Met Glu
                595                 600                 605

His Leu Lys Lys Ala Asp Lys Ile Leu Ile Leu His Glu Gly Ser Ser
                610                 615                 620

Tyr Phe Tyr Gly Thr Phe Ser Glu Leu Gln Ser Gln Arg Pro Asp Phe
625                 630                 635                 640

Ser Ser Lys Leu Met Gly Tyr Asp Thr Phe Asp Gln Phe Thr Ala Glu
                645                 650                 655

Arg Arg Asn Ser Ile Ile Thr Glu Thr Leu Arg Arg Phe Ser Leu Glu
                660                 665                 670

Gly Asp Ala Ser Val Ser Trp Asn Glu Thr Lys Lys Gln Ser Phe Lys
                675                 680                 685

Gln Thr Gly Glu Phe Gly Glu Lys Arg Lys Asn Ser Ile Leu Asn Ser
690                 695                 700

Ile Asn Ser Ile Arg Lys Phe Ser Ile Val Gln Lys Thr Pro Leu Gln
705                 710                 715                 720

Met Asn Gly Phe Glu Glu Asp Ser Gly Glu Pro Leu Glu Arg Arg Leu
                725                 730                 735

Ser Leu Val Pro Asp Ser Glu His Gly Glu Ala Ile Leu Pro Arg Ser
                740                 745                 750

Asn Val Ile Asn Ala Gly Pro Thr Phe Gln Gly Arg Arg Arg Gln Ser
                755                 760                 765

Val Leu Asn Leu Met Thr Arg Ser Ser Val Asn Gln Gly Gln Ser Ile
                770                 775                 780

His Arg Lys Thr Ala Thr Ser Thr Arg Lys Met Ser Leu Val Pro Gln
785                 790                 795                 800
```

-continued

```
Ala Asn Leu Thr Glu Ile Asp Ile Tyr Ser Arg Arg Leu Ser Gln Asp
                805                 810                 815

Thr Gly Leu Glu Ile Ser Glu Glu Ile Asn Glu Glu Asp Leu Arg Glu
            820                 825                 830

Cys Phe Phe Asp Asp Val Glu Ser Ile Pro Thr Val Thr Thr Trp Asn
            835                 840                 845

Thr Tyr Leu Arg Tyr Val Thr Val His Lys Ser Leu Ile Phe Val Leu
        850                 855                 860

Ile Trp Cys Leu Val Val Phe Leu Ala Glu Val Ala Ala Cys Leu Val
865                 870                 875                 880

Val Leu Cys Leu Leu Lys Lys Thr Ser Pro Gln Asp Lys Gly Asn Ser
                885                 890                 895

Thr Lys Gly Ala Asn Asn Ser Tyr Ala Val Ile Ile Thr Ser Thr Ser
            900                 905                 910

Ala Tyr Tyr Val Phe Tyr Ile Tyr Val Gly Val Ala Asp Gly Leu Leu
        915                 920                 925

Ala Leu Gly Leu Phe Arg Gly Leu Pro Leu Val His Thr Leu Ile Thr
        930                 935                 940

Val Ser Lys Ile Leu His Arg Lys Met Leu His Ser Val Leu Gln Ala
945                 950                 955                 960

Pro Met Ser Thr Leu Asn Thr Leu Lys Ala Gly Gly Ile Leu Asn Arg
                965                 970                 975

Phe Ser Lys Asp Ile Ala Val Leu Asp Asp Leu Leu Pro Leu Thr Ile
            980                 985                 990

Phe Asp Phe Ile Gln Leu Leu Leu  Ile Val Ile Gly Ala  Val Ala Val
            995                 1000                1005

Val Ser Val Leu Lys Pro Tyr  Ile Phe Leu Ala Thr  Val Pro Val
    1010                1015                1020

Ile Val Ala Phe Ile Leu Leu  Arg Ala Tyr Phe Leu  His Thr Ser
    1025                1030                1035

Gln Gln Leu Lys Gln Leu Glu  Ser Glu Gly Arg Ser  Pro Ile Phe
    1040                1045                1050

Thr His Leu Ile Thr Ser Leu  Lys Gly Leu Trp Thr  Leu Arg Ala
    1055                1060                1065

Phe Gly Arg Gln Pro Tyr Phe  Glu Thr Leu Phe His  Lys Ala Leu
    1070                1075                1080

Asn Leu His Thr Ala Asn Trp  Phe Leu Tyr Leu Ser  Thr Leu Arg
    1085                1090                1095

Trp Phe Gln Met Arg Ile Glu  Met Ile Phe Val Ile  Phe Phe Ile
    1100                1105                1110

Ala Val Thr Phe Ile Ser Ile  Leu Thr Thr Gly Glu  Gly Glu Gly
    1115                1120                1125

Thr Val Gly Ile Ile Leu Thr  Leu Ala Met Asn Ile  Met Ser Thr
    1130                1135                1140

Leu Gln Trp Ala Val Asn Ser  Ser Ile Asp Val Asp  Ser Leu Met
    1145                1150                1155

Arg Ser Val Ser Arg Val Phe  Lys Phe Ile Asp Met  Pro Ala Glu
    1160                1165                1170

Gly Asp Gln Pro Asn Arg Ser  Phe Lys Pro Ser Lys  Asp Gly Gln
    1175                1180                1185

Leu Ser Lys Val Met Ile Ile  Glu Asn Gln His Val  Lys Lys Asp
    1190                1195                1200

Asp Ile Trp Pro Ser Gly Gly  Gln Met Thr Val Lys  Asp Leu Thr
    1205                1210                1215
```

```
Ala Lys Tyr Val Asp Gly Gly Asn Ala Val Leu Glu Asn Ile Ser
    1220            1225                1230
Phe Ser Ile Ser Pro Gly Gln Arg Val Gly Leu Leu Gly Arg Thr
    1235            1240                1245
Gly Ser Gly Lys Ser Thr Leu Leu Leu Ala Phe Leu Arg Leu Leu
    1250            1255                1260
Asn Thr Glu Gly Glu Ile Gln Val Asp Gly Val Ser Trp Asp Ser
    1265            1270                1275
Ile Thr Leu Gln Gln Trp Arg Lys Ala Phe Gly Val Ile Pro Gln
    1280            1285                1290
Lys Val Phe Ile Phe Ser Gly Thr Phe Arg Lys Asn Leu Asp Pro
    1295            1300                1305
Tyr Gly Gln Trp Asn Asp Gln Glu Ile Trp Lys Val Ala Glu Glu
    1310            1315                1320
Val Gly Leu Arg Ser Val Ile Glu Gln Phe Pro Gly Lys Leu Asp
    1325            1330                1335
Phe Val Leu Val Asp Gly Gly Cys Val Leu Ser His Gly His Lys
    1340            1345                1350
Gln Leu Met Cys Leu Ala Arg Ser Val Leu Gly Lys Ala Lys Ile
    1355            1360                1365
Leu Leu Leu Asp Glu Pro Ser Ala His Leu Asp Pro Ile Thr Tyr
    1370            1375                1380
Gln Ile Ile Arg Arg Thr Leu Lys Gln Ala Phe Ala Asp Cys Thr
    1385            1390                1395
Val Ile Leu Ser Glu His Arg Ile Glu Ala Met Leu Glu Cys Gln
    1400            1405                1410
Arg Phe Leu Val Ile Glu Glu Asn Lys Val Arg Gln Tyr Asp Ser
    1415            1420                1425
Ile Gln Arg Leu Leu Ser Glu Lys Ser Leu Phe Arg Gln Ala Ile
    1430            1435                1440
Ser Pro Leu Asp Arg Leu Lys Leu Leu Pro His Arg Asn Ser Ser
    1445            1450                1455
Lys Gln Arg Ser Arg Ser Lys Ile Ala Ala Leu Lys Glu Glu Thr
    1460            1465                1470
Glu Glu Glu Val Gln Glu Thr Arg Leu
    1475            1480

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
tttctcttct gcctatttcc c                                         21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
agaaaacact gaaggatgcc t                                         21
```

```
<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
gtttcaaata gttactcagt ttga                                    24

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
cctccaactg acactaatct tctca                                   25

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gtagagctgt cagagaagta a                                       21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
aagccacaga agcatatgca t                                       21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
aatcactctc aggatgcaca t                                       21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
atactcagaa caggaagtgc t                                       21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
```

```
atagcataag cttcactgtg c                                              21

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
tgtcagtaga gaattagaga tta                                            23

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gcactactca cctacatcca                                                20

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
acctggaagt tggaacactc a                                              21

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
gaagaccctt taccttcttc ta                                             22

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
catccagctg caaacaacat t                                              21

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
aattatgcca aactccatct tat                                            23

<210> SEQ ID NO 22
<211> LENGTH: 22
<212> TYPE: DNA
<213> ORGANISM: Artificial Sequence
```

-continued

```
<220> FEATURE:
<223> OTHER INFORMATION: Primer

<400> SEQUENCE: 22
agaatttcat tctgctctca gt                                              22

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
agtgggctgt aaactccagt ataga                                           25

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
ccttctgccg gcatatcaat aaact                                           25

<210> SEQ ID NO 25
<211> LENGTH: 17
<212> TYPE: DNA
<213> ORGANISM: Artificial Sequence
<220> FEATURE:
<223> OTHER INFORMATION: Primer

<400> SEQUENCE: 25
atcgcatcaa gctatcc                                                    17

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
aagctcattt cctcgtacga caat                                            24

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
ggaggccatg tggaccat                                                   18

<210> SEQ ID NO 28
<211> LENGTH: 17
<212> TYPE: DNA
<213> ORGANISM: Artificial Sequence
<220> FEATURE:
<223> OTHER INFORMATION: Primer

<400> SEQUENCE: 28
tccaccaccc tgttgct                                                    17
```

```
<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tcatgccggg caccattaaa                                               20

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
cgctttgatg acactcctgt atcta                                         25

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
acaccaaaga tgatgttttc                                               20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
tcatgccggg caccattaaa                                               20

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
cgctttgatg acactcctgt atcta                                         25

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gaaacaccaa tgatgttttc                                               20

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
```
agaatttcat tctgctctca gt                                              22

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36 gaagacccttt taccttcttc ta                                             22

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
tcatgccggg caccattaaa                                                 20

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
cgctttgatg acactcctgt atcta                                           25

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
acaccaaaga tgatgttttc                                                 20

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
aagctcattt cctcgtacga caat                                            24

<210> SEQ ID NO 41
<211> LENGTH: 18
<212> TYPE: DNA
<213> ORGANISM: Artificial Sequence
<220> FEATURE:
<223> OTHER INFORMATION: Primer

<400> SEQUENCE: 41
ggaggccatg tggaccat                                                   18

<210> SEQ ID NO 42
<211> LENGTH: 17
<212> TYPE: DNA
<213> ORGANISM: Artificial Sequence

```
<220> FEATURE:
<223> OTHER INFORMATION: Primer

<400> SEQUENCE: 42
tccaccaccc tgttgct                                                    17
```